US008026247B2

(12) United States Patent
Bold et al.

(10) Patent No.: US 8,026,247 B2
(45) Date of Patent: Sep. 27, 2011

(54) BICYCLIC AMIDES AS KINASE INHIBITORS

(75) Inventors: Guido Bold, Gipf-Oberfrick (CH);
Hans-Georg Capraro, Rheinfelden (CH); Giorgio Caravatti, Bottmingen (CH); Andreas Floersheimer, Dornach (CH); Pascal Furet, Thann (FR); Paul W. Manley, Arlesheim (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 611 days.

(21) Appl. No.: 11/575,025

(22) PCT Filed: Sep. 14, 2005

(86) PCT No.: PCT/IB2005/004030
§ 371 (c)(1),
(2), (4) Date: Feb. 11, 2008

(87) PCT Pub. No.: WO2006/059234
PCT Pub. Date: Jun. 8, 2006

(65) Prior Publication Data
US 2008/0287427 A1    Nov. 20, 2008

(30) Foreign Application Priority Data

Sep. 15, 2004  (GB) .................................. 0420520.9
Jun. 8, 2005   (GB) .................................. 0511687.6

(51) Int. Cl.
*C07D 239/46* (2006.01)
*C07D 403/12* (2006.01)
*C07D 413/12* (2006.01)
*A61K 31/505* (2006.01)

(52) U.S. Cl. ........ 514/269; 514/272; 514/256; 514/105; 544/105; 544/321; 546/297

(58) Field of Classification Search ................ 544/105, 544/321; 514/272, 105, 256, 269; 546/297
See application file for complete search history.

(56) References Cited

U.S. PATENT DOCUMENTS

| 7,253,286 | B2 | 8/2007 | Funahashi et al. | |
| 7,435,823 | B2 * | 10/2008 | Potashman et al. | 546/153 |
| 2004/0053908 | A1 | 3/2004 | Funahashi et al. | |
| 2005/0070508 | A1 * | 3/2005 | Lou et al. | 514/130 |
| 2008/0039440 | A1 | 2/2008 | Bold et al. | |

FOREIGN PATENT DOCUMENTS

| EP | 1506962 | 2/2005 |
| WO | 01/16130 | 3/2001 |
| WO | 01/60816 | 8/2001 |
| WO | 02/00647 | 1/2002 |
| WO | 03/068228 | 8/2003 |
| WO | 03/099771 | 12/2003 |
| WO | 2004/020434 | 3/2004 |
| WO | 2004/043379 | 5/2004 |
| WO | 2005/021553 | 3/2005 |
| WO | 2005/023761 | 3/2005 |
| WO | 2005/070891 | 8/2005 |
| WO | 2005/108387 | 11/2005 |
| WO | WO 2006/059234 A2 | 6/2006 |

OTHER PUBLICATIONS

Guido Bold, et al., U.S. Appl. No. 12/446,955, entitled "Cyclic sulfones useful as mitochondrial sodium-calcium exchangers", filed Apr. 23, 2009.
Paul W. Manley, et al., U.S. Appl. No. 12/596,193, entitled "Organic Compounds", filed Oct. 16, 2009.
Joerg Berghausen, et al., U.S. Appl. No. 12/827,218, entitled "Pharmaceutical Compositions and Solid Forms", filed Jun. 30, 2010.
No Author, Search Results National Phase Entries WO 2006/059234, WIPO IP Services, Retrieved 2001, 1 page.
Baron, Mark, Transmittal Letter to the United States Desginated/ Elected Office (DO/EO/US) Concerning a Filing Under 35 U.S.C. 371 for International Application PCT/IB2005/004030, Mar. 9, 2007, 2 pages.
Marti, Christiane, Correspondence to Deutsches Patent- und Markenamt Requesting File Inspection of PCT/DE2005/001813, Dated Feb. 1, 2011, 2 pages.
Paech, Correspondence from Deutsches Patent- und Markenamt to Novartis Pharma AG Regarding File Inspection Request, Dated Feb. 2, 2011, 1 page.
Marti, Christiane, Correspondence to World Intellectual Property Organization Regarding Request for File Inspection of PCT/ DE2005/001813 / PCT/IB2005/004030 Forwarded by the German Patent and Trademark Office, Dated Feb. 16, 2011, 2 pages.
Marti, Christiane, Email Exchange with Ingrid Aulich at the World Intellectual Property Organization, Dated Feb. 18, 2011 and Feb. 21, 2011, 2 pages.
Aulich, Ingrid, Letter Forwarding and Copy of Documents Contained in the World Intellectual Property Organization File for International Application No. PCT/IB2005/004030 (filed on Sep. 14, 2005) Published Under No. WO 2006/059234, Dated Mar. 1, 2011, 152 pages.
No Author, "Information About Mail Received Erroneously at EPO or German Patent and Trademark Office," PCT Newsletter, Aug. 2005, 1 page, No. 08/2005.

* cited by examiner

*Primary Examiner* — Kahsay T Habte
(74) *Attorney, Agent, or Firm* — Paul D. Strain; Strain & Strain PLLC

(57) ABSTRACT

The invention relates to compounds of formula (I) and their use in the treatment of the animal or human body, to pharmaceutical compositions comprising a compound of formula I and to the use of a compound of formula I for the preparation of pharmaceutical compositions for use in the treatment of protein kinase dependent diseases, especially of proliferative diseases, such as in particular tumour diseases.

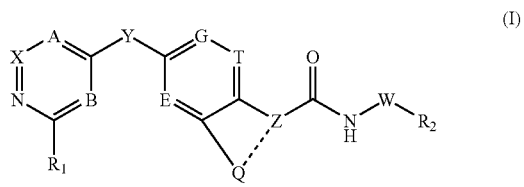

3 Claims, No Drawings

BICYCLIC AMIDES AS KINASE INHIBITORS

This application is the National Stage of Application No. MT/IB2005/004030, filed on Sep. 14, 2005. The contents of both are incorporated herein by reference in their entirety.

The invention relates to compounds of formula I and their use in the treatment of the animal or human body, to pharmaceutical compositions comprising a compound of formula I and to the use of a compound of formula I for the preparation of pharmaceutical compositions for use in the treatment of protein kinase dependent diseases, especially of proliferative diseases, such as in particular tumour diseases.

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive wild-type or mutated PK activity has been observed in many disease states including benign and malignant proliferative disorders. In many cases, it has been possible to treat diseases, such as proliferative disorders, by making use of PK inhibitors.

In view of the large number of protein kinases and the multitude of proliferative and other PK-related diseases, there is an ever-existing need to provide compounds that are useful as PK inhibitors and thus in the treatment of these PK related diseases.

It has now been found that the compounds of formula I show inhibition of a number of protein kinases. The compounds of formula I, described below in more detail, especially show inhibition of one or more of the following protein kinases: EphB4, c-Abl, Bcr-Abl, c-Kit, Raf kinases such as especially B-Raf, the rearranged during transfection (RET) proto-oncogene, Platelet-derived Growth Factor Receptors (PDGF-Rs) and most especially the Vascular Endothelial Growth Factor Receptors (VEGF-Rs) such as in particular VEGF-R2. The compounds of formula I further also inhibit mutants of said kinases. In view of these activities, the compounds of formula I can be used for the treatment of diseases related to especially aberrant or excessive activity of such types of kinases, especially those mentioned.

The invention especially relates to compounds of the formula I

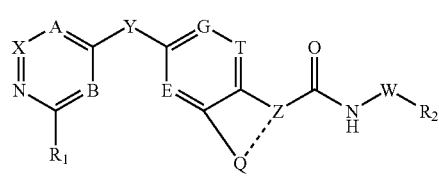

(I)

wherein
$R_1$ is H; halo; cyano; —$C_0$-$C_7$—O—$R_3$; —$C_0$-$C_7$—$NR_4R_5$; or —C(=O)—$R_6$;
$R_2$ is substituted $C_3$-$C_8$-cycloalkyl; substituted aryl; or substituted heterocyclyl;
$R_3$ is H or unsubstituted or substituted lower alkyl;
$R_4$ and $R_5$ are independently selected from the group consisting of H; unsubstituted or substituted lower alkyl; lower alkyl-carbonyl, wherein the lower alkyl moiety is optionally substituted; and lower alkoxy-carbonyl, wherein the lower alkyl moiety is optionally substituted;
$R_6$ is H; unsubstituted or substituted lower alkyl; lower alkoxy, wherein the lower alkyl moiety is optionally substituted; or unsubstituted, mono- or di-substituted amino;
A, B and X are independently selected from =C($R_7$)— or N;
E, G and T are independently selected from =C($R_8$)— or N;
$R_7$ and $R_8$ are independently selected from the group consisting of H, halo and unsubstituted or substituted lower alkyl;
Y is —O—, —S—, —S(O)—, —S(O)$_2$—, —CH$_2$—, —CH$_2$—CH$_2$—, —CH=CH— or —C≡C—;
Z is CH or N and Q is $C_1$-$C_4$-alkylene or $C_2$-$C_4$-alkenylene, wherein $C_1$-$C_4$-alkylene or $C_2$-$C_4$-alkenylene optionally may be substituted and wherein one or more of the carbon atoms of said $C_1$-$C_4$-alkylene or $C_2$-$C_4$-alkenylene chain optionally may be replaced by a heteroatom independently selected from nitrogen, oxygen and sulfur; and the bond between Q and Z characterized by a dotted line is a single bond; with the proviso that if Z is N, Q is not unsubstituted unbranched $C_1$-$C_4$-alkylene;
or
Z is C and Q is as defined above wherein the bond between Q and Z characterized by a dotted line is a double bond; and W is either not present or $C_1$-$C_3$-alkylene;
or a tautomer thereof, or a salt thereof.

The present invention also relates to a method of treating a kinase dependent and/or proliferative disease comprising administering a compound of the formula I to a warm-blooded animal, especially a human, and the use of a compound of the formula I, especially for treating a kinase dependent disease or disorder. The present invention also relates to pharmaceutical preparations comprising a compound of the formula I, especially for the treatment of a kinase dependent disease or disorder, a process for the manufacture of a compound of the formula I, and novel starting materials and intermediates for their manufacture. The present invention also relates to the use of a compound of formula I in the manufacture of a pharmaceutical preparation for the treatment of a kinase dependent disease.

The general terms used hereinbefore and hereinafter preferably have, within this disclosure, the following meanings, unless otherwise indicated:

The term "lower" defines a moiety with up to and including maximally 7, especially up to and including maximally 4, carbon atoms, said moiety being branched or straight-chained. Lower alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

The term "$C_0$-$C_7$-" is as defined above for "lower" with the difference that in case of "$C_0$-" no carbon atom is present.

Substituted lower alkyl or a substituted lower alkyl moiety is a lower alkyl radical/moiety substituted by one or more, preferably one, substituent, selected independently from e.g. amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, halo, or unsubstituted or substituted heterocyclyl.

$C_1$-$C_4$-alkylene and $C_2$-$C_4$-alkenylene may be branched or unbranched and are in particular $C_2$-$C_3$-alkylene and $C_2$-$C_3$-alkenylene, respectively. In optionally substituted $C_1$-$C_4$-alkylene or $C_2$-$C_4$-alkenylene, the substituents are e.g. selected from amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio and halo, or lower alkyl substituted by one or more, preferably one, of said substituents.

Mono- or di-substituted amino is amino substituted by one or two radicals selected independently of one another from e.g. substituted and especially unsubstituted lower alkyl.

Substituted $C_3$-$C_8$-cycloalkyl is especially cyclopropyl or cyclohexyl and is preferably substituted as described for substituted aryl.

Substituted aryl is preferably an aromatic radical with 4 to 8 carbon atoms, especially phenyl, wherein said radical is substituted by one or more, preferably by one or two, radicals such as e.g. unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkanoyl, lower alkanoyloxy, cyano, nitro, carboxy, lower alkoxycarbonyl, carbamoyl, N-lower alkyl-carbamoyl, N,N-di-lower alkyl-carbamoyl, amidino, guanidino, ureido, mercapto, lower alkylthio, halo, or unsubstituted or substituted heterocyclyl.

Unsubstituted or substituted heterocyclyl is preferably a saturated, partially saturated or unsaturated mono- or bicyclic radical having from 4 to 8 ring members and from 1 to 3 heteroatoms which are preferably selected from nitrogen, oxygen and sulfur, said radical being unsubstituted or substituted preferably as described for substituted aryl.

Halo(geno) is preferably iodo, bromo, chloro or fluoro, especially fluoro, chloro or bromo.

$R_1$ is preferably amino; halo, such as especially chloro; cyano; lower alkyl-amino, such as especially methylamino; amino-lower alkyl, such as especially amino-methyl; mono- or di-lower alkyl-amino-lower alkyl, such as especially methylamino-methyl or dimethylamino-methyl; lower alkoxy-carbonyl, such as especially methoxy-carbonyl, ethoxy-carbonyl or butoxy-carbonyl; mono- or di-lower alkyl-amino-carbonyl, such as especially methylamino-carbonyl, dimethylamino-carbonyl or isopropylamino-carbonyl; (2)-dimethylamino-ethyl-(1)-amino-carbonyl; lower alkyl-carbonyl-amino such as especially methylcarbonyl-amino; lower alkoxy-carbonyl-amino, such as especially methoxycarbonyl-amino or butoxycarbonyl-amino; carboxyl; hydroxy-methyl; chloro-methyl or methoxy-carbonyl-amino-methyl.

$R_1$ is most preferably amino; or methylcarbonyl-amino.

$R_2$ is preferably a cyclohexyl, phenyl or pyridyl, especially a phenyl, radical wherein said radical is substituted by one or more, especially 1 or 2, substituents independently selected from the group consisting of lower alkyl; cyclopropyl; methoxy; halo; halo-lower alkyl, such as especially trifluoromethyl or difluoroethyl; trifluoromethoxy; morpholinyl, such as especially morpholin-4-yl; morpholinyl-lower alkyl, such as especially morpholin-4-ylmethyl; piperazinyl-lower alkyl and lower alkyl-piperazinyl-lower alkyl, such as especially 4-methylpiperazin-1-ylmethyl.

$R_2$ is most preferably phenyl, substituted by one or two radicals independently selected from the group consisting of fluoro, trifluoromethyl and 4-methylpiperazin-1-ylmethyl.

Preferably X is $=C(R_7)$— and one of A and B is N while the other is $=C(R_7)$—; most preferably X and A are both $=CH$— and B is N.

Preferably E, G and T are $=C(R_7)$—; most preferably E, G and T are all $=CH$—.

$R_7$ and $R_8$ are preferably H or halo; most preferably $R_7$ and $R_8$ are H.

Y is preferably —O—.

Z is preferably N or C, most preferably C.

Q is preferably $C_2$-$C_4$-alkenylene, or $C_1$-$C_4$-alkylene wherein one or more, especially one, of the carbon atoms of $C_1$-$C_4$-alkylene is replaced by a heteroatom independently selected from nitrogen, oxygen and sulfur, especially from oxygen. Q is especially selected from —O—$CH_2$—[Z], —O—$CH_2$—$CH_2$—[Z], —CH=CH— and —CH=CH—CH=, wherein "—[Z]" indicates where the bivalent radical is bound to Z in formula I if there are two possibilities; most preferably Q is —CH=CH—CH=.

W is preferably not present.

Where the plural form is used for compounds, salts, pharmaceutical compositions, diseases and the like, this is intended to mean also a single compound, salt, or the like.

In view of the close relationship between the compounds of formula I in free form and in the form of their salts, including those salts that can be used as intermediates, for example in the purification or identification of the compounds of formula I, tautomers or tautomeric mixtures and their salts, any reference hereinbefore and hereinafter to these compounds is to be understood as referring also to the corresponding tautomers of these compounds, tautomeric mixtures of these compounds, N-oxides of these compounds, or salts of any of these, as appropriate and expedient and if not mentioned otherwise. Tautomers can, e.g., be present in cases where amino or hydroxy are bound to carbon atoms that are bound to adjacent atoms by double bonds (e.g. keto-enol or imine-enamine tautoemerism).

Where "a compound . . . , a tautomer thereof; or a salt thereof" or the like is mentioned, this means "a compound . . . , a tautomer thereof, or a salt of the compound or the tautomer".

Asymmetric carbon atoms of a compound of formula I that are optionally present may exist in the (R), (S) or (R,S) configuration, preferably in the (R) or (S) configuration. Substituents at a double bond or a ring may be present in cis- (=Z-) or trans (=E-) form. The compounds may thus be present as mixtures of isomers or preferably as pure isomers.

Salts are preferably the pharmaceutically acceptable salts of the compounds of formula I.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, hetero-aromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The terms "treatment" or "therapy" refer to the prophylactic or preferably therapeutic (including but not limited to palliative, curing, symptom-alleviating, symptom-reducing, kinase-regulating and/or kinase-inhibiting) treatment of said diseases, especially of the diseases mentioned below.

Where subsequently or above the term "use" is mentioned (as verb or noun) (relating to the use of a compound of the formula I or a pharmaceutically acceptable salt thereof), this includes any one or more of the following embodiments of the invention, respectively: the use in the treatment of a protein kinase dependent disease, the use for the manufacture of pharmaceutical compositions for use in the treatment of a protein kinase dependent disease, methods of use of one or more compounds of the formula I in the treatment of a protein kinase dependent disease, the use of pharmaceutical preparations comprising one or more compounds of the formula I for the treatment of a protein kinase dependent disease, and one or more compounds of the formula I for use in the treatment of a protein kinase dependent disease, as appropriate and expedient and if not stated otherwise. In particular, diseases to be treated and are thus preferred for "use" of a compound of formula I are selected from protein kinase dependent ("dependent" meaning also "supported", not only "solely dependent") diseases mentioned herein, especially proliferative diseases mentioned herein, more especially any one or more of these or other diseases that depend on one or more of c-Abl, Bcr-Abl, c-Kit, Raf kinases such as especially B-Raf, the rearranged during transfection (RET) proto-oncogene, Platelet-derived Growth Factor Receptors (PDGF-Rs) and most especially the Vascular Endothelial Growth Factor Receptors (VEGF-Rs) such as in particular VEGF-R2, or a mutant of any one or more of these, and a compound of the formula I can therefore be used in the treatment of a kinase dependent disease, especially a disease depending on one or more of the kinases mentioned above and below, where (especially in the case of aberrantly highly-expressed, constitutively activated and/or mutated kinases) said kinase-dependent disease is dependent on the activity of one or more of the said kinases or the pathways they are involved.

The compounds of formula I have valuable pharmacological properties and are useful in the treatment of protein kinase dependent diseases, for example as drugs to treat proliferative diseases.

The efficacy of the compounds of formula I as inhibitors of c-Abl protein tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 µL): c-Abl kinase (50 ng), 20 mM Tris-HCl, pH 7.5, 10 mM $MgCl_2$, 10 M $Na_3VO_4$, 1 mM DTT and 0.06 µCi/assay $[\gamma^{33}P]$-ATP (5 µM ATP using 30 µg/ml poly-Ala,Glu,Lys,Tyr-6:2:5:1 (Poly-AEKY, Sigma P1152) in the presence of 1% DMSO. Reactions are terminated by adding 10 µL of 250 mM EDTA and 30 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). Using this test system, the compounds of formula I show $IC_{50}$ values of inhibition in the range of 0.001 to 100 µM, usually between 0.05 and 5 µM.

Bcr-Abl inhibition can be determined by a capture ELISA as follows: The murine myeloid progenitor cell line 32Dcl3 transfected with the p210 Bcr-Abl expression vector pGDp210Bcr/Abl (32D-bcr/abl) is obtained from J Griffin (Bazoni et al., J. Clin Invest. 98, 521-8 (1996); Zhao et al., Blood 90, 4687-9 (1997)). The cells express the fusion bcr-abl protein with a constitutively active abl kinase and proliferate growth factor-independent. The cells are expanded in RPMI 1640 (AMIMED; cat #1-41 F01), 10% fetal calf serum, 2 mM glutamine (Gibco) ("complete medium"), and a working stock is prepared by freezing aliquots of $2 \times 10^6$ cells per vial in freezing medium (95% fetal calf serum, 5% dimethylsulfoxide (SIGMA, D-2650). After thawing, the cells are used during maximally 10-12 passages for the experiments. The antibody anti-abl SH3 domain cat. #06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. #03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (ST1571) (marketed as Gleevec® or Glivec®, Novartis), is used. A stock solution of 10 mM is prepared in DMSO and stored at −20° C. For the cellular assays, the stock solution is diluted in complete medium in two steps (1:100 and 1:10) to yield a starting concentration of 10 µM followed by preparation of serial three-fold dilutions in complete medium. No solubility problems are encountered using this procedure. The test compounds of formula I are treated analogously. For the assay, 200,000 32D-bcr/abl cells in 50 µl are seeded per well in 96 well round bottom tissue culture plates. 50 µl per well of serial threefold dilutions of the test compound are added to the cells in triplicates. The final concentration of the test compound range e.g. from 5 µM down to 0.01 µM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 µg/ml aprotinin and 80 µg/ml leupeptin) and either used immediately for the ELISA or stored frozen at −20® C. until usage. The anti-abl SH3 domain antibody is coated at 200 ng in 50 µl PBS per well to black ELISA plates (Packard HTRF-96 black plates; 6005207) overnight at 4° C. After washing 3× with 200 μl/well PBS containing 0.05% Tween 20 (PBST) and 0.5% TopBlock (Juro, Cat. #TB 232010), residual protein binding sites are blocked with 200 μl/well PBST, 3% TopBlock for 4 h at room temperature, followed by incubation with 50 μl lysates of untreated or test compound-treated cells (20 μg total protein per well) for 3-4 h at 4° C. After 3× washing, 50 μl/well PY20(AP) (Zymed) diluted to 0.5 μg/ml in blocking buffer is added and incubated overnight (4° C.). For all incubation steps, the plates are covered with plate sealers (Costar, cat. #3095). Finally, the plates are washed another three times with washing buffer and once with deionized water before addition of 90 μl/well of the AP substrate CPDStar RTU with Emerald II. The plates now sealed with Packard Top Seal™-A plate sealers (cat. #6005185) are incubated for 45 min at room temperature in the dark and luminescence is quantified by measuring counts per second (CPS) with a Packard Top Count Microplate Scintillation Counter (Top Count). For the final optimized version of the ELISA, 50 μl of the lysates of the cells grown, treated and lysed in 96 well tissue culture plates, are transferred directly from these plates to the ELISA plates that are precoated with 50 ng/well of the rabbit poylclonal ant-abl-SH3 domain AB 06-466 from Upstate. The concentration of the anti-phosphotyrosine AB PY20 (AP) can be reduced to 0.2 μg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the $IC_{50}$ are determined from the dose response curves by graphical inter- or extrapolation. The compounds of formula I here show $IC_{50}$ values in the range from 20 nM to 20 μM.

The efficacy of the compounds of formula I as inhibitors of c-Kit and PDGF-R tyrosine kinase activity can be demonstrated as follows:

BaF3-Tel-PDGFRbeta and BaF3-KitD816V are BaF3 murine proB-cell lymphoma cell derivatives [the BaF3 cell line is available from the German Collection of Microorganisms and Cell Cultures (DSMZ), Braunschweig, Germany] that have been rendered IL-3-independent by stable transduction with Tel-fusion-activated PDGFβ-R wild-type (Golub T. R. et al., Cell 77(2): 307-316, 1994) or D816V-mutation-activated c-kit, respectively. Cells are cultured in RPMI-1640 (Animed #1-14F01-I) supplemented with 2% L-glutamine (Animed #5-10K50-H) and 10% fetal calf serum (FCS, Animed #2-01 F16-I). Wild-type, untransfected BaF3 cells are maintained in above medium plus 10 U/ml IL-3 (mouse Interleukin-3, Roche #1380745).

Cells are diluted in fresh medium to a final density of $3 \times 10^5$ cells per ml and 50 μl aliquots seeded into 96-well plates ($1.5 \times 10^4$ cells per well). 50 μl 2× compound solutions are added. As internal control, the kinase inhibitor PKC412 is routinely used. Control cells treated with DMSO (0.1% final concentration) serve as growth reference (set as 100% growth). In addition, a plate blank value is routinely determined in a well containing only 100 μl of medium and no cells. $IC_{50}$ determinations are performed based on eight 3-fold serial dilutions of the test compound, starting at 10 μM. Following incubation of the cells for 48 h at 37° C. and 5% $CO_2$, the effect of inhibitors on cell viability is assessed by the resazurin sodium salt dye reduction assay (commercially known as AlamarBlue assay) basically as previously described (O'Brien J. et al., Eur. J. Biochem. 267: 5421-5426, 2000). 10 μl of AlamarBlue is added per well and the plates incubated for 6 h at 37° C. and 5% $CO_2$. Thereafter, fluorescence is measured using a Gemini 96-well plate reader (Molecular Devices) with the following settings: Excitation 544 nm and Emission 590 nm.

Acquired raw data are exported to Excel-file format. For data analysis, the plate blank value is subtracted from all data points. The anti-proliferative effect of a compound by the AlamarBlue read-out was then calculated as percentage of the value of the control cells set as 100%. $IC_{50}$ values are determined using XLfit software program. The compounds of formula I show an $IC_{50}$ for c-Kit and PDGFβ-R in the range of 0.0003 to 20 μM, especially between 0.001 and 0.1 μM.

Active Raf kinases, such as active B-Raf protein, of human sequence are purified from insect cells using the baculoviral expression system. Raf inhibition is tested in 96-well microplates coated with IκB-α and blocked with Superblock. The phosphorylation of IκB-α at Serine 36 is detected using a phospho-IκB-α specific antibody (Cell Signaling #9246), an anti-mouse IgG alkaline phosphatase conjugated secondary antibody (Pierce #31320), and an alkaline phosphatase substrate, ATTOPHOS (Promega, #S101).

RET kinase inhibition is determined as follows:

Cloning and expression: The baculovirus donor vector pFB-GSTX3 is used to generate a recombinant baculovirus that expresses the amino acid region 658-1072 (Swiss prot No. Q9BTB0) of the cytoplasmic kinase domain of human RET-Men2A which corresponds to the wild-type kinase domain of RET (wtRET) and RET-Men2B, which differs from the wtRET by the activating mutation in the activation loop M918T. The coding sequence for the cytoplasmic domain of wtRET is amplified by PCR from a cDNA library using specific primers. RET-Men2B is generated through site-directed mutagenesis resulting in the M918T mutation. The amplified DNA fragments and the pFB-GSTX3 vector are made compatible for ligation by digestion with SalI and KpnI. Ligation of these DNA fragments results in the baculovirus donor plasmids pFB-GX3-RET-Men2A and pFB-GX3-RET-Men2B, respectively.

Production of virus: The baculovirus donor plasmids containing the kinase domains are transfected into the DH10Bac cell line (GIBCO) and the transfected cells are plated on selective agar plates. Colonies without insertion of the fusion sequence into the viral genome (carried by the bacteria) are blue. Single, white colonies are picked and viral DNA (bacmid) is isolated from the bacteria by standard plasmid purification procedures. Sf9 cells or Sf21 cells (American Type Culture Collection) are then transfected in 25 cm² flasks with the viral DNA using Cellfectin reagent.

Protein expression in Sf9 cells: Virus-containing media is collected from the transfected cell culture and used for infection to increase its titer. Virus-containing media obtained after two rounds of infection is used for large-scale protein expression. For large-scale protein expression 100 cm² round tissue culture plates are seeded with $5 \times 10^7$ cells/plate and infected with 1 ml of virus-containing media (approximately 5 MOIs). After 3 days, the cells are scraped off the plate and centrifuged at 500 rpm for 5 minutes. Cell pellets from 10-20, 100 cm² plates are re-suspended in 50 ml of ice-cold lysis buffer (25 mM Tris-HCl, pH 7.5, 2 mM EDTA, 1% NP-40, 1 mM DTT, 1 mM PMSF). The cells are stirred on ice for 15 minutes and then centrifuged at 5,000 rpms for 20 minutes.

Purification of GST-tagged proteins: The centrifuged cell lysate is loaded onto a 2 ml glutathione-sepharose column (Pharmacia) and washed 3× with 10 ml of 25 mM Tris-HCl, pH 7.5, 2 mM EDTA, 1 mM DTT, 200 mM NaCl. The GST-tagged proteins are then eluted by 10 applications (1 ml each) of 25 mM Tris-HCl, pH 7.5, 10 mM reduced-glutathione, 100 mM NaCl, 1 mM DTT, 10% glycerol and stored at −70° C.

Measure of enzyme activity: Tyrosine protein kinase assays with either purified GST-wtRET or GST-RET-Men2B protein are carried out in a final volume of 30 μL containing 15 ng of either GST-wtRET or GST-RET-Men2B protein, 20 mM Tris-HCl, pH 7.5, 1 mM $MnCl_2$, 10 mM $MgCl_2$, 1 mM DTT, 3 μg/ml poly(Glu,Tyr) 4:1, 1% DMSO, 2.0 μM ATP (γ-[$^{33}$P]-ATP 0.1 μCi). The activity is assayed in the presence or absence of inhibitors, by measuring the incorporation of $^{33}$P from [$γ^{33}$P] ATP into poly(Glu,Tyr) 4:1. The assay is carried out in 96-well plates at ambient temperature for 15 minutes under conditions described above and terminated by the addition of 20 μL of 125 mM EDTA. Subsequently, 40 μL of the reaction mixture are transferred onto Immobilon-PVDF membrane (Millipore) previously soaked for 5 minutes with methanol, rinsed with water, then soaked for 5 minutes with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed 4× on a shaker with 1.0% $H_3PO_4$, once with ethanol. Membranes are counted after drying at ambient temperature, mounting in Packard TopCount 96-well frame, and addition of 10 μL/well of Microscint™ (Packard). $IC_{50}$ values are calculated by linear regression analysis of the percentage inhibition of each compound in duplicate, at 4 concentrations (usually 0.01, 0.1, 1 and 10 μM). One unit of protein kinase activity is defined as 1 nmole of $^{33}$P transferred from [$γ^{33}$P] ATP to the substrate protein/minute/mg of protein at 37° C. The compounds of formula I here show $IC_{50}$ values in the range between 0.005 and 20 μM, especially between 0.01 and 1 μM.

VEGF-R1 inhibition can be shown as follows: the test is conducted using Flt-1 VEGF-receptor tyrosine kinase. The detailed procedure is as follows: 30 μl kinase solution (kinase domain of Flt-1, Shibuya et al., Oncogene 5, 519-24 [1990], according to the specific activity, in order to achieve an activity of 4000-6000 counts per minute [cpm] in the sample without inhibitor) in 20 mM Tris-HCl pH 7.5, 3 mM manganese dichloride ($MnCl_2$), 3 mM magnesium chloride ($MgCl_2$) and 3 μg/ml poly(Glu,Tyr) 4:1 (Sigma, Buchs, Switzerland), 8 μM [$^{33}$P]-ATP (0.2 μCi/batch), 1% dimethyl sulfoxide, and 0 to 50 μM of the compound to be tested are incubated together for 10 minutes at room temperature. The reaction is then ended by the addition of 10 μl 0.25 M ethylenediaminetetraacetate (EDTA) pH 7. Using a multichannel dispenser (LAB SYSTEMS, USA), an aliquot of 20 μl is applied to a PVDF (=polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid ($H_3PO_4$), incubated for 10 minutes each time while shaking, then mounted in a Hewlett Packard TopCount Manifold and the radioactivity measured after the addition of 10 μl Microscint® (β-scintillation counter liquid; Packard USA). $IC_{50}$-values are determined by linear regression analysis of the percentages for the inhibition of each compound in three concentrations (as a rule 0.01, 0.1, and 1 μM). The $IC_{50}$ values that can be found with the compounds of formula I are in the range of 0.01 to 100 μM, especially in the range from 0.01 to 20 μM.

Analogously to the above test, the efficacy of the compounds according to the invention as inhibitors of VEGF-R2 tyrosine kinase activity can be tested using the VEGF receptor tyrosine kinase KDR. In this test, instead of the Flt-1 kinase domain, the KDR kinase domain (Parast et al., Biochemistry 37 (47), 16788-801 (1998)) is used. The only difference in carrying out this test from the above test lies in the concentration of poly(Glu,Tyr) 4:1 (8 μg/ml), $MnCl_2$ (1 mM) and $MgCl_2$ (10 mM). Compounds of formula I in this instance have $IC_{50}$ values in the range of 0.0003 μM to 20 μM, especially in the range of 10 nM to 500 nM.

The inhibition of VEGF-induced receptor autophosphorylation can be confirmed with an in vitro experiments in cells such as transfected CHO cells, which permanently express human VEGF-R2 (KDR), are seeded in complete culture medium (with 10% fetal calf serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. #TB232010) in phosphate buffered saline with Tween 20® (polyoxyethylen(20)sorbitane monolaurate, ICI/Uniquema) (PBST). The cell lysates (20 μg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the $IC_{50}$ (inhibitory dose for 50% inhibition). The compounds of formula I here show an $IC_{50}$ in the range of 0.0003 to 20 μM, especially between 0.001 and 0.1 μM.

Based on the property of the compounds of formula I as potent VEGF receptor inhibitors, the compounds of formula I are especially suitable for the treatment of diseases associated with deregulated angiogenesis, especially diseases caused by ocular neovascularisation, especially retinopathies such as diabetic retinopathy or age-related macula degeneration, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, endometriosis, chronic asthma, arterial or post-transplantational atherosclerosis, neurodegenerative disorders, and especially neoplastic diseases (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AML (acute myeloid leukemia), AMM (agnogenic myeloid metaplasia), mesothelioma, glioma and glioblastoma. A compound of formula I is especially suited also to preventing the metastatic spread of tumours and the growth of micrometastases.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

In another aspect the present invention relates to compounds of the formula I wherein
$R_1$ is H; halo; —$C_0$-$C_7$—O—$R_3$; —$C_0$-$C_7$—$NR_4R_5$; or —C(=O)—$R_6$;
$R_2$ is substituted $C_3$-$C_8$-cycloalkyl; substituted aryl; or substituted heterocyclyl;
$R_3$ is H or unsubstituted or substituted lower alkyl;
$R_4$ and $R_5$ are independently selected from the group consisting of H; unsubstituted or substituted lower alkyl; lower alkyl-carbonyl, wherein the lower alkyl moiety is optionally substituted; and lower alkoxy-carbonyl, wherein the lower alkyl moiety is optionally substituted;
$R_6$ is H; unsubstituted or substituted lower alkyl; lower alkoxy, wherein the lower alkyl moiety is optionally substituted; or unsubstituted, mono- or di-substituted amino;
A, B and X are independently selected from =C($R_7$)— or N;
E, G and T are independently selected from =C($R_8$)— or N;
$R_7$ and $R_8$ are independently selected from the group consisting of H, halo and unsubstituted or substituted lower alkyl;
Y is —O—, —S—, —S(O)—, —S(O)$_2$—, —$CH_2$— or —$CH_2$—$CH_2$—;
Z is CH or N and Q is $C_1C_4$-alkylene or $C_2$-$C_4$-alkenylene, wherein $C_1$-$C_4$-alkylene or $C_2$-$C_4$-alkenylene optionally may be substituted and wherein one or more of the carbon atoms of said $C_1$-$C_4$-alkylene or $C_2$-$C_4$-alkenylene chain optionally may be replaced by a heteroatom independently selected from nitrogen, oxygen and sulfur; and the bond between Q and Z characterized by a dotted line is a single bond; with the proviso that if Z is N, Q is not unsubstituted unbranched $C_1$-$C_4$-alkylene;
or
Z is C and Q is as defined above wherein the bond between Q and Z characterized by a dotted line is a double bond; and
W is either not present or $C_1$-$C_3$-alkylene;
or a tautomer thereof, or a salt thereof.

Preference is given to a compound of formula I, wherein
$R_1$ is halo; —CO—$C_7$—$NR_4R_5$; or —C(=O)—$R_6$;
$R_2$ is substituted $C_3$-$C_8$-cycloalkyl; substituted aryl; or substituted heterocyclyl;
$R_4$ and $R_5$ are independently selected from the group consisting of H; lower alkyl; lower alkyl-carbonyl; and lower alkoxy-carbonyl;
$R_6$ is lower alkyl, lower alkoxy, lower alkyl-amino, di-lower alkyl-amino-lower alkyl-amino or di-lower alkyl-amino;
A, B and X are independently selected from =C($R_7$)— or N;
E, G and T are =C($R_8$)—;
$R_7$ and $R_8$ are independently selected from H and halo;
Y is —O—, —S— or —$CH_2$—, especially —O—;
Z is N and Q is $C_1$-$C_4$-alkylene or $C_2$-$C_4$-alkenylene, wherein one or more, especially one, of the carbon atoms of said $C_1$-$C_4$-alkylene or $C_2$-$C_4$-alkenylene chain optionally may be replaced by a heteroatom independently selected from nitrogen, oxygen and sulfur, especially from oxygen, the Nitrogen optionally substituted by lower alkyl; and the bond between Q and Z characterized by a dotted line in formula I is a single bond; with the proviso that Q is not unsubstituted unbranched $C_1$-$C_4$-alkylene;
or
Z is C and Q is as defined above wherein the bond between Q and Z characterized by a dotted line in formula I is a double bond; and
W is $C_1$-$C_3$-alkylene or especially not present;
or a tautomer thereof, or a salt thereof.

Special preference is given to a compound of formula I, wherein
Z is N and Q is $C_2$-$C_4$-alkenylene, or $C_1$-$C_4$-alkylene wherein one or more, especially one, of the carbon atoms of $C_1$-$C_4$-alkylene is replaced by a heteroatom independently selected from nitrogen, oxygen and sulfur, especially from oxygen; and the bond between Q and Z characterized by a dotted line in formula I is a single bond;
or
Z is C and Q is as defined above wherein the bond between Q and Z characterized by a dotted line in formula I is a double bond;
and wherein the other substituents and symbols have the meanings as described herein,
especially the meanings described as being preferred;
or a tautomer thereof, or a salt thereof.

Especially preferred is further a compound of formula I, wherein
$R_1$ is halo; —CO—$C_7$—$NR_4R_5$; or —C(=O)—$R_6$;
$R_2$ is a cyclohexyl, phenyl, pyridyl, 2H-indazolyl, 1,3-dihydro-2-benzofuranyl or pyrazole radical wherein said radical is substituted by one or more substituents independently selected from the group consisting of lower alkyl; $C_3$-$C_8$-cycloalkyl, optionally substituted by morpholinyl; lower alkoxy; halo; halo-lower alkyl; halo-lower alkoxy; $SF_5$; morpholinyl; morpholinyl-lower alkyl; piperazinyl-lower alkyl; lower alkyl-piperazinyl-lower alkyl and phenyl, wherein said phenyl is optionally substituted by lower alkyl, halo, di-lower alkyl-amino-lower alkyl, lower alkyl-piperazinyl-lower alkyl or morpholinyl-lower alkyl;
$R_4$ and $R_5$ are independently selected from the group consisting of H; lower alkyl; lower alkyl-carbonyl; and lower alkoxy-carbonyl;
$R_6$ is lower alkoxy, lower alkyl-amino or di-lower alkyl-amino;
X is =C($R_7$)— and one of A and B is N while the other is =C($R_7$)—;
E, G and T are =C($R_8$)—;
$R_7$ and $R_8$ are independently selected from the group consisting of H and halo;
Y is —O—;
Z is N and Q is $C_2$-$C_3$-alkylene or $C_2$-$C_3$-alkenylene, wherein one of the carbon atoms of said $C_2$-$C_3$-alkylene chain optionally may be replaced by oxygen; and the bond between Q and Z characterized by a dotted line in formula I is a single bond; with the proviso that Q is not unsubstituted unbranched C₂-C₃-alkylene;
or
Z is C and Q is —CH═CH—CH═; and
W is not present;
or a tautomer thereof, or a salt thereof.

Especially preferred is further a compound of formula I, wherein
R₁ is chloro; cyano; methylamino; amino-methyl; methylamino-methyl; dimethylamino-methyl; methoxy-carbonyl, ethoxy-carbonyl; butoxy-carbonyl; methylamino-carbonyl, dimethylamino-carbonyl; isopropylamino-carbonyl; (2)-dimethylamino-ethyl-(1)-amino-carbonyl; methylcarbonyl-amino; methoxycarbonyl-amino; butoxycarbonyl-amino; carboxyl; hydroxy-methyl; chloro-methyl or methoxy-carbonyl-amino-methyl;
R₂ is a cyclohexyl, phenyl, pyridyl, 2H-indazolyl, 1,3-dihydro-2-benzofuranyl or pyrazole radical wherein said radical is substituted by one or more substituents independently selected from the group consisting of methyl; ethyl; propyl; butyl; cyclopropyl; morpholin-4-ylcyclohexyl; methoxy; fluoro; chloro; bromo; trifluoromethyl; difluoroethyl; trifluoromethoxy; SF₅; morpholinyl; morpholin-4-ylmethyl; piperazinyl-methyl; 4-methylpiperazin-1-ylmethyl; 4-ethylpiperazin-1-ylmethyl; 4-propylpiperazin-1-ylmethyl and phenyl, wherein said phenyl is optionally substituted by methyl, fluoro, dimethylamino-methyl, morpholin-4-ylmethyl, 4-methylpiperazin-1-ylmethyl or dimethylaminocarbonyl;

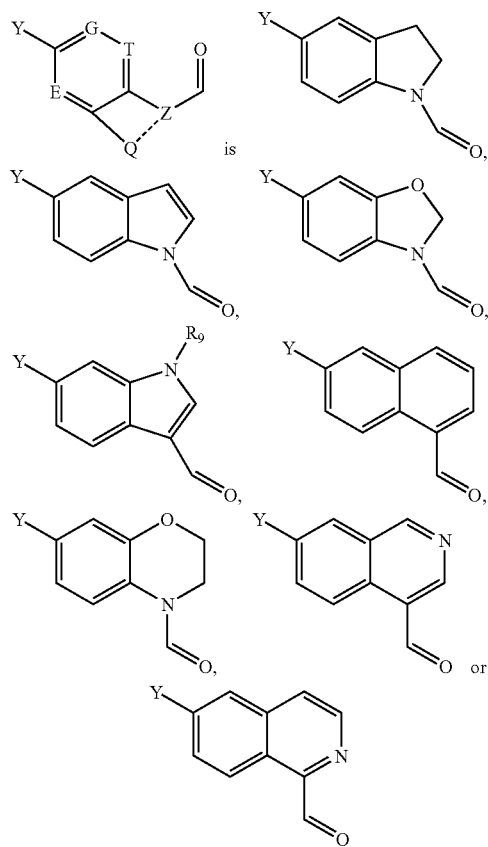

R₉ is H, methyl, ethyl or propyl;
one of A and B is N while the other is ═CH—;

Y is —O—; —S—; —CH₂—CH₂—; —CH═CH— or —C≡C—;
W is CH₂ or not present;
or a tautomer thereof, or a salt thereof.

Even more especially preferred is a compound of formula I, wherein
Z is C and Q is —CH═CH—CH═;
and wherein the other substituents and symbols have the meanings as described herein, especially the meanings described as being preferred;
or a tautomer thereof, or a salt thereof.

Even more especially preferred is further a compound of formula I, wherein

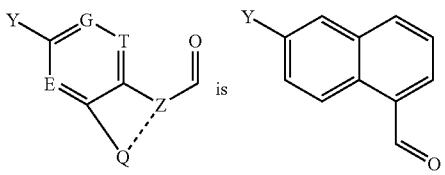

and wherein the other substituents and symbols have the meanings as described herein, especially the meanings described as being preferred;
or a tautomer thereof, or a salt thereof.

Even more especially preferred is further a compound of formula I, wherein
R₂ is phenyl which is substituted by one or more substituents independently selected from the group consisting of fluoro; trifluoromethyl and 4-methylpiperazin-1-ylmethyl;
and wherein the other substituents and symbols have the meanings as described herein, especially the meanings described as being preferred;
or a tautomer thereof, or a salt thereof.

Most preferred is a compound of the formula I, or a tautomer thereof or a (preferably pharmaceutically acceptable) salt thereof, as exemplified hereinbelow under 'Examples', or its use as defined herein.

Preference is furthermore given to a compound of formula I, wherein
R₁ is H; halo; —CO—C₇-Q-R₃; —CO—C₇—NR₄R₅; or —C(═O)—R₆;
R₂ is substituted C₃-C₈-cycloalkyl; substituted aryl; or substituted heterocyclyl;
R₃ is H or unsubstituted or substituted lower alkyl;
R₄ and R₅ are independently selected from the group consisting of H; unsubstituted or substituted lower alkyl; lower alkyl-carbonyl, wherein the lower alkyl moiety is optionally substituted; and lower alkoxy-carbonyl, wherein the lower alkyl moiety is optionally substituted;
R₆ is H; unsubstituted or substituted lower alkyl; lower alkoxy, wherein the lower alkyl moiety is optionally substituted; or unsubstituted, mono- or di-substituted amino;
A, B and X are independently selected from ═C(R₇)— or N;
E, G and T are independently selected from ═C(R₈)— or N;
R₇ and R₈ are independently selected from the group consisting of H, halo and unsubstituted or substituted lower alkyl;
Y is —O—, —S— or —CH₂—;
Z is CH or N and Q is C₁-C₄-alkylene or C₂-C₄-alkenylene, wherein C₁-C₄-alkylene or C₂-C₄-alkenylene optionally may be substituted and wherein one or more of the carbon atoms of said C₁-C₄-alkylene or C₂-C₄-alkenylene chain optionally may be replaced by a heteroatom independently selected from nitrogen, oxygen and sulfur; and the bond between Q and Z characterized by a dotted line is a single bond; with the proviso that if Z is N, Q is not unsubstituted unbranched $C_1$-$C_4$-alkylene;
or
Z is C and Q is as defined above wherein the bond between Q and Z characterized by a dotted line is a double bond; and
W is either not present or $C_1$-$C_3$-alkylene;
or a tautomer thereof, or a salt thereof.

Special preference is furthermore given to a compound of formula I, wherein
$R_1$ is halo; —CO—$C_7$—$NR_4R_5$; or —C(=O)—$R_6$;
$R_2$ is a cyclohexyl, phenyl or pyridyl radical wherein said radical is substituted by one or more substituents independently selected from the group consisting of lower alkyl; halo; halo-lower alkyl; morpholinyl; morpholinyl-lower alkyl; and lower alkyl-piperazinyl-lower alkyl;
$R_4$ and $R_5$ are independently selected from the group consisting of H; lower alkyl; lower alkyl-carbonyl; and lower alkoxy-carbonyl;
$R_6$ is lower alkoxy, lower alkyl-amino or di-lower alkyl-amino;
X is =C($R_7$)— and one of A and B is N while the other is =C($R_7$)—;
E, G and T are =C($R_8$)—;
$R_7$ and $R_8$ are independently selected from the group consisting of H and halo;
Y is —O—;
Z is N and Q is $C_2$-$C_3$-alkylene or $C_2$-$C_3$-alkenylene, wherein one of the carbon atoms of said $C_2$-$C_3$-alkylene chain optionally may be replaced by oxygen; and the bond between Q and Z characterized by a dotted line in formula I is a single bond; with the proviso that Q is not unsubstituted unbranched $C_2$-$C_3$-alkylene;
or
Z is C and Q is —CH=CH—CH=; and
W is not present;
or a tautomer thereof, or a salt thereof.

Compounds of formula I are prepared analogously to methods that, for other compounds, are in principle known in the art, and are especially prepared according to the methods described hereinbelow under 'Examples'.

The starting materials used in the preparation of the compounds of formula I are known, capable of being prepared according to known processes, or commercially obtainable. In particular, the anilines to be used as starting material in the preparation of the compounds of formula I can be prepared as described in WO 03/099771 or analogously thereto, are commercially available or can be prepared according to known processes.

The invention relates also to pharmaceutical compositions comprising a compound of formula I, to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The pharmacologically acceptable compounds of the present invention may be present in or employed, for example, for the preparation of pharmaceutical compositions that comprise an effective amount of a compound of the formula I, or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment of (this, in a broader aspect of the invention, also includes the prevention of (=prophylaxis against)) a disease that responds to inhibition of protein kinase activity, comprising an amount of a compound of formula I or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, or topical, such as a gel, paste, ointment, cream or foam, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase and/or a proliferative disease, which comprises administering a (against the mentioned diseases) prophylactically or especially therapeutically effective amount of a compound of formula I according to the invention, or a tautomer thereof or a pharmaceutically acceptable salt thereof, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

The pharmaceutical compositions of the present invention are prepared in a manner known per se, for example by means of conventional dissolving, lyophilizing, mixing, granulating or confectioning processes.

A compound of the formula I may also be used to advantage in combination with other antiproliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R. P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists such as pemetrexed. Capecitabine can be administered, e.g., in the form as it is marketed, e.g. under the trademark XELODA. Gemcita-bine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, erg.:

a) compounds targeting, decreasing or inhibiting the activity of the fibroblast growth factor-receptors (FGF-Rs);
b) compounds targeting, decreasing or inhibiting the activity of the insulin-like growth factor I receptor (IGF-IR), especially compounds which inhibit the IGF-IR, such as those compounds disclosed in WO 02/092599;
c) compounds targeting, decreasing or inhibiting the activity of the Trk receptor tyrosine kinase family;
d) compounds targeting, decreasing or inhibiting the activity of the Axl receptor tyrosine kinase family;
e) compounds targeting, decreasing or inhibiting the activity of the c-Met receptor;
f) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; llmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor);

g) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); and h) compounds targeting, decreasing or inhibiting the activity of the epidermal growth factor family of receptor tyrosine kinases (EGF-R, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HERCEPTIN), cetuximab, Iressa, erlotinib (Tarceva™), Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TN P-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or any combination thereof.

EXAMPLES

The following Examples serve to illustrate the invention without limiting the scope thereof.

Temperatures are measured in degrees Celsius. Unless otherwise indicated, the reactions take place at room temperature under $N_2$-atmosphere.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

ABBREVIATIONS

Anal. elemental analysis (for indicated atoms, difference between calculated and measured value $\leq 0.4\%$)
aq. aqueous
brine saturated solution of NaCl in water
conc. concentrated
DEPC diethyl-cyanophosphonate
DIPE diisopropyl-ether
DMAP dimethylaminopyridine
DMEU 1,3-dimethyl-2-imidazolidinone
DMF dimethyl formamide
DMSO dimethyl sulfoxide
ether diethylether
$Et_3N$ triethylamine
EtOAc ethyl acetate
EtOH ethanol
eq. equivalent
Ex. Example
h hour(s)
HATU O-(7-azabenzotriazol-1-yl)-N,N,N',N'-tetramethyluronium-hexafluorophosphate
HPLC high pressure liquid chromatography
HV high vacuum
l litre(s)
Me methyl
MeOH methanol
min minute(s)
m.p. melting point
MPLC medium pressure liquid chromatography
    Combi Flash system: normal phase $SiO_2$
    Gilson system: reversed phase Nucleosil C18 ($H_2O$/$CH_3CN$+TFA), generally product obtained as free base after neutralization with $NaHCO_3$
MS mass spectrum
NMM N-methyl-morpholine
NMP N-methyl-pyrrolidone
prep-HPLC preparative high pressure liquid chromatography; Waters system; column: reversed phase Atlantis™ (100×19 mm), dC18 OBD ($H_2O$/$CH_3CN$+0.1% TFA), 5 µM, generally product obtained as a TFA salt after lyophilization.
propylphosphonic anhydride
    N-propylphosphonic acid anhydride, cyclic trimer [68957-94-8]; 50% in DMF
$R_f$ ratio of fronts (TLC)
rt room temperature
sat. saturated
THF tetrahydrofuran (distilled from Na/benzophenone)
TFA trifluoroacetic acid
TLC thin layer chromatography
$t_{Ret}$ retention time (HPLC)
triphosgene bis(trichloromethyl) carbonate
sat. saturated HPLC Conditions:

$^A t_{Ret}$: retention time [min] for System A: Linear gradient 20-100% CH$_3$CN (0.1% TFA) and H$_2$O (0.1% TFA) in 13 min+5 min 100% CH$_3$CN (0.1% TFA); detection at 215 nm, flow rate 1 ml/min at 25 or 30° C. Column: Nucleosil 120-3 C18 (125×3.0 mm).

$^B t_{Ret}$: retention time [min] for System B: Linear gradient 5-40% CH$_3$CN (0.1% TFA) and H$_2$O (0.1% TFA) in 9 min+7 min 40% CH$_3$CN (0.1% TFA); detection at 215 nm, flow rate 1 ml/min at 25 or 30° C. Column: Nucleosil 120-3 C18 (125×3.0 mm).

$^C t_{Ret}$: retention time [min] for System C: Linear gradient 15-100% CH$_3$CN (0.1% TFA) and H$_2$O (0.1% TFA) in 2.25 min+1.25 min 100% CH$_3$CN (0.1% TFA); detection at 215 nm, flow rate 2 ml/min at 25 or 30° C. Column: CC (50×4.6 mm) Uptisphere UP3ODB-5QS.

$^D t_{Ret}$: retention time [min] for System D: Linear gradient 20-100% CH$_3$CN (0.1% TFA) and H$_2$O (0.1% TFA) in 5 min+1 min 100% CH$_3$CN (0.1% TFA); detection at 215 nm, flow rate 1 ml/min at 25 or 30° C. Column: CC (250×4.6 mm) Nucleosil 100-5 C18.

$^E t_{Ret}$: retention time [min] for System E: Linear gradient 20-100% CH$_3$CN (0.1% TFA) and H$_2$O (0.1% TFA) in 14 min+5 min 100% CH$_3$CN (0.1% TFA); detection at 215 nm, flow rate 1 ml/min at 25 or 30° C. Column: CC 70/4 (70×4.0 mm) Nucleosil 100-3 C18.

$^F t_{Ret}$: retention time [min] for System F: Linear gradient 5-100% CH$_3$CN and H$_2$O (0.1% TFA) in 4 min+0.5 min 100% CH$_3$CN; PDA MaxPlot detection (210.0 nm to 400.0 nm), flow rate 3 ml/min at 35° C. Column: Sunfire (4.6×20 mm) C18, 3.5 µm.

$^G t_{Ret}$: retention time [min] for System G: Linear gradient 5-100% CH$_3$CN (0.07% formic acid) and H$_2$O (0.1% formic acid) in 4 min+0.5 min 100% CH$_3$CN (0.07% formic acid); PDA MaxPlot detection (210.0 nm to 400.0 nm), flow rate 1.8 ml/min at 40° C. Column: X-Terra™ (4.6×50 mm) MSC18, 5 µm.

Anilines used as educts: Most respective anilines are either commercially available or described in WO 03/099771 or WO 05/051366 or can be prepared analogously to the therein exemplified derivatives.

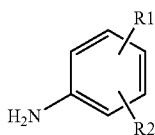

Example 1 rac-5-(2-Amino-6-chloro-pyrimidin-4-yloxy)-4-fluoro-2-methyl-2,3-dihydro-indole-1-carboxylic acid (3-trifluoromethyl-phenyl)-amide 0.68 mMol rac-5-(2-Amino-6-chloro-pyrimidin-4-yloxy)-4-fluoro-2-methyl-2,3-dihydro-indole (Step 1.2) are dissolved in 5 ml THF. Then 106 µl (0.77 mMol) 3-trifluoromethyl-phenylisocyanat are added and the solution is stirred for 1 h at rt. Concentration and chromatography (Combi Flash; EtOAc/hexane 1:9→1:1) gives the title compound: MS: [M+1]$^+$=482/484; HPLC: $^A t_{Ret}$=16.4; Anal.: C,H,N,Cl,F.

The starting material is prepared as follows:

Step 1.1: 5-(2-Amino-6-chloro-pyrimidin-4-yloxy)-4-fluoro-2-methyl-1H-indole 1.00 g (6.05 mMol) 2-amino-4,6-dichloro-pyrimidine and 993 mg (6.05 mMol) 4-fluoro-5-hydroxy-2-methylindole [preparation see: WO 00/47212 Ex. 237] are suspended in 25 ml acetone. Then 12 ml 1 N NaOH in water are added and the mixture is stirred at an oilbath temperature of 70° C. for 5 h. Then additional 210 mg 2-amino-4,6-dichloro-pyrimidine are added portionwise and stirring continued for another 4.5 h. The reaction mixture is partially concentrated and the crystallized title compound filtered off and washed with water: m.p.: 255-258° C.; MS: [M+1]$^+$=293/295; HPLC: $^A t_{Ret}$=13.7.

Step 1.2: rac-5-(2-Amino-6-chloro-pyrimidin-4-yloxy)-4-fluoro-2-methyl-2,3-dihydro-1H-indole A solution of 200 mg (0.68 mMol) of 5-(2-amino-6-chloro-pyrimidin-4-yloxy)-4-fluoro-2-methyl-1H-indole in 4 ml acetic acid is cooled to 10-15° C. Then 214 mg (3.4 mMol) NaBH$_3$CN are added. After 3 h stirring at rt, 8 g of ice are added, then the mixture is made basic by addition of 1 N NaOH and extracted three times with EtOAc. The organic layers are washed with water and brine, dried (Na$_2$SO$_4$) and concentrated at rt in vacuo: HPLC: $^A t_{Ret}$=9.9.

Example 2 rac-5-(2-Amino-pyrimidin-4-yloxy)-4-fluoro-2-methyl-2,3-dihydro-indole-1-carboxylic acid (3-trifluoromethyl-phenyl)-amide A solution of 230 mg (0.48 mMol) rac-5-(2-amino-6-chloro-pyrimidin-4-yloxy)-4-fluoro-2-methyl-2,3-dihydro-indole-1-carboxylic acid (3-trifluoromethyl-phenyl)-amide and 75 µl (0.54 mMol) Et$_3$N in 12 ml THF is hydrogenated in the presence of 63 mg Pd/C (10%; Engelhard 4505). The catalyst is filtered off, the filtrate concentrated and the residue dissolved in EtOAc and H$_2$O. The aqueous layer is extracted twice with EtOAc. The organic layers are washed with water and brine, dried (Na$_2$SO$_4$) and concentrated. Crystallization from EtOAc/DIPE gives the title compound: MS: [M+1]$^+$= 448; HPLC: $^A t_{Ret}$=12.7.

Example 3

5-(6-Chloro-pyrimidin-4-yloxy)-indole-1-carboxylic acid (3-trifluoromethyl-phenyl)-amide A solution of 492 mg (2.00 mMol) of 5-(6-chloro-pyrimidin-4-yloxy)-1H-indole (WO 03/099771; Stage 163.1), 344 mg (2.12 mMol) of 1,1'-carbonyl-diimidazol and 6 mg DMAP in 7 ml CH$_3$CN is stirred at 80° C. for 8 h. After cooling to rt, 356 µl (2.86 mMol) 3-trifluoromethyl-aniline are added to the suspension, which then is stirred again for 9 h at 80° C. The reaction mixture is filtered and the filtrate diluted with EtOAc and H$_2$O. The aqueous layer is extracted twice with EtOAc. The organic layers are washed with water and brine, dried (Na$_2$SO$_4$) and concentrated. Reversed phase MPLC (Gilson system) gives the title compound: MS: [M+1]+=433/435; TLC(EtOAc/CH$_2$Cl$_2$ 3:97): R$_f$=0.15; HPLC: $^A t_{Ret}$=16.8.

Example 4

5-(6-Amino-pyrimidin-4-yloxy)-indole-1-carboxylic acid (3-trifluoromethyl-phenyl)-amide To a solution of 150 mg (0.35 mMol) 5-(6-chloro-pyrimidin-4-yloxy)-indole-1-carboxylic acid (3-trifluoromethyl-phenyl)-amide in 2 ml DMF, 45 mg (0.69 mMol) NaN$_3$ are added at rt. After 2 h at 65° C., the solution containing 5-(6-azido-pyrimidin-4-yloxy)-indole-1-carboxylic acid (3-trifluoromethyl-phenyl)-amide is cooled to rt. Then 12 mg Pd/C (10%; Engelhard 4505) are added and the mixture is hydrogenated for 1 h. The catalyst is filtered off and the filtrate concentrated in vacuo. Reversed phase MPLC (Gilson system) gives the title compound: MS: [M+1]$^+$=414; HPLC: $^A t_{Ret}$=12.6.

Example 5

7-(6-Amino-pyrimidin-4-yloxy)-2,3-dihydro-benzo[1,4]oxazine-4-carboxylic acid (4-methyl-3-trifluoromethyl-phenyl)-amide 104 mg (0.35 mMol) triphosgene are dissolved in 13 ml ice cooled $CH_2Cl_2$. Then a solution of 183 mg (1.05 mMol) 5-amino-2-methylbenzotrifluoride and 209 µl (1.5 mMol) $Et_3N$ in 6 ml $CH_2Cl_2$ is added during 8 min. After 3 minutes, the mixture is warmed up to rt by a water bath and then a solution of 244 mg (1.00 mMol) 6-(3,4-dihydro-2H-benzo[1,4]oxazin-7-yloxy)-pyrimidin-4-ylamine (Step 5.6) and 139 µl (1.0 mMol) $Et_3N$ in 6 ml $CH_2Cl_2$ is added during 10 min. After 2.5 h at rt, the mixture is diluted with sat. $Na_2CO_3/H_2O$ 1:1 and EtOAc, the aqueous phase separated off and extracted twice with EtOAc. The organic layers are washed with water and brine, dried ($Na_2SO_4$) and concentrated partially. Addition of ether and hexane gives the crystalline title compound: MS: [M+1]$^+$=446; TLC(EtOAc): $R_f$=0.30; HPLC: $^A t_{Ret}$=12.3.

The starting material is prepared as follows:

Step 5.1: 2-(2,4-Dimethoxy-phenylamino)-ethanol 30.6 g (0.20 Mol) 2,4-dimethoxy-aniline are dissolved in 200 ml EtOAc. Then 14.8 ml (95%; 0.20 Mol) of 2-bromethanol and 33.6 g (0.40 Mol) $NaHCO_3$ are added and the suspension is heated to 77° C. for 20 h. The mixture is cooled to rt and filtered. Concentration of the filtrate and column chromatography ($SiO_2$; hexane/EtOAc 3:1-2:1-1:1) gives the title compound as an oil: MS: [M+1]$^+$=198; TLC(EtOAc): $R_f$=0.50; HPLC: $^B t_{Ret}$=9.2.

Step 5.2: (2-Bromo-ethyl)-(2,4-dihydroxy-phenyl)-carbamic acid benzyl ester 22 g (0.11 Mol) 2-(2,4-dimethoxy-phenylamino)-ethanol and 125 ml HBr (62% in $H_2O$) are heated to 140° C. for 15 h. The resulting dark solution is concentrated in vacuo. The residue is diluted with 60 ml water and 120 ml EtOAc and cooled in an ice bath. Then 30 ml (95%; 0.20 Mol) benzyl chloroformate are added. Under vigorous stirring, 90 ml $Na_2CO_3$ 2 M are added dropwise during 20 min. After 90 min stirring at rt, the reaction mixture is filtered, the aqueous phase of the filtrate separated off and extracted twice with 30 ml EtOAc. The organic layers are washed with 30 ml brine, dried ($Na_2SO_4$) and concentrated. Column chromatography ($SiO_2$; hexane/EtOAc 4:1-7:3-3:2) gives the title compound as an oil: MS: [M+1]$^+$=366/368; TLC(EtOAc/hexane 1:1): $R_f$=0.34; HPLC: $^A t_{Ret}$=12.6.

Step 5.3: 7-Hydroxy-2,3-dihydro-benzo[1,4]oxazine-4-carboxylic acid benzyl ester To a solution of 32 g (87.4 mMol) (2-bromo-ethyl)-(2,4-dihydroxy-phenyl)-carbamic acid benzyl ester in 100 ml DMF, 16 g (116 mMol) $K_2CO_3$ are added. After 1 h stirring at rt, the reaction mixture is filtered and the filtrate concentrated in vacuo. The resulting brown oil is diluted with 120 ml EtOAc and 50 ml citric acid (5% in $H_2O$). The aqueous phase is separated off and extracted twice with EtOAc. The organic layers are washed with water and brine, dried ($Na_2SO_4$) and concentrated, giving the oily title compound: MS: [M+1]$^+$=286; TLC(EtOAc/hexane 1:1): $R_f$=0.61; HPLC: $^A t_{Ret}$=13.0.

Step 5.4: 7-(6-Chloro-pyrimidin-4-yloxy)-2,3-dihydro-benzo[1,4]oxazine-4-carboxylic acid benzyl ester To a solution of 9.73 g (95%; 32.5 mMol) 7-hydroxy-2,3-dihydro-benzo[1,4]oxazine-4-carboxylic acid benzyl ester in 96 ml of acetone, 4.84 g (32.5 mMol) 4,6-dichloropyrimidine are added. Then a solution of 1.3 g (32.5 mMol) NaOH in 48 ml of water is added and the mixture stirred for 2 h at rt. Addition of some seeding crystals leads to the crystallization of the title compound, which is filtered off and washed with acetone/$H_2O$ 1:1: m.p.: 110° C.; MS: [M+1]$^+$=398/400; HPLC: $^A t_{Ret}$=16.4. More product can be isolated from the filtrate by extraction (EtOAc; $NaHCO_3$, water and brine) and column chromatography ($SiO_2$; hexane/EtOAc 9:1-4:1→3:1).

Step 5.5: 7-(6-Azido-pyrimidin-4-yloxy)-2,3-dihydro-benzo[1,4]oxazine-4-carboxylic acid benzyl ester To a solution of 8.0 g (20.1 mMol) 7-(6-chloro-pyrimidin-4-yloxy)-2,3-dihydro-benzo[1,4]oxazine-4-carboxylic acid benzyl ester in 35 ml DMF, 2.61 g (40.2 mMol) $NaN_3$ are added. After heating at 70° C. for 90 min, the resulting mixture is diluted with EtOAc and water, the aqueous phase separated off and extracted twice with EtOAc. The organic layers are washed with water and brine, dried ($Na_2SO_4$) and concentrated, giving the title compound: MS: [M+1]$^+$=405; HPLC: $^A t_{Ret}$=16.6.

Step 5.6: 6-(3,4-Dihydro-2H-benzo[1,4]oxazin-7-yloxy)-pyrimidin-4-ylamine

A solution of 20.1 mMol 7-(6-azido-pyrimidin-4-yloxy)-2,3-dihydro-benzo[1,4]oxazine-4-carboxylic acid benzyl ester in 500 ml THF is hydrogenated in the presence of 3.5 g Pd/C (10%; Engelhard 4505). The catalyst is filtered off, the filtrate concentrated and crystallized from DIPE, giving the title compound: m.p.: 140-141° C.; MS: [M+1]$^+$=245; TLC (EtOAc): $R_f$=0.11.

Example 6

7-(6-Amino-pyrimidin-4-yloxy)-2,3-dihydro-benzo[1,4]oxazine-4-carboxylic acid (4-fluoro-3-trifluoromethyl-phenyl)-amide Prepared analogously to Ex. 5: MS: [M+1]$^+$=450; TLC (EtOAc): $R_f$=0.23; HPLC: $^A t_{Ret}$=11.9.

Example 7

7-(6-Amino-pyrimidin-4-yloxy)-2,3-dihydro-benzo[1,4]oxazine-4-carboxylic acid (3-trifluoromethyl-phenyl)-amide A solution of 120 µl (0.87 mMol) 3-trifluoromethyl-phenyl-isocyanate in 9 ml ether is added dropwise to 0.20 g (0.82 mMol) 6-(3,4-dihydro-2H-benzo[1,4]oxazin-7-yloxy)-pyrimidin-4-ylamine in 4.5 ml THF. After 45 min at rt, 10 ml hexane are added. Then the crystallized title compound is

Example 8

7-(6-Methylamino-pyrimidin-4-yloxy)-2,3-dihydro-benzo[1,4]oxazine-4-carboxylic acid (4-methyl-3-trifluoromethyl-phenyl)-amide 73 mg (0.25 mMol) triphosgene are dissolved in 9 ml ice cooled $CH_2Cl_2$. Then a solution of 134 mg (97%; 0.74 mMol) 5-amino-2-methylbenzotrifluoride and 146 μl (1.05 mMol) $Et_3N$ in 4 ml $CH_2Cl_2$ is added during 5 min. After 3 minutes, the mixture is warmed up to rt by a water bath and then a solution of 180 mg (0.70 mMol) [6-(3,4-dihydro-2H-benzo[1,4]oxazin-7-yloxy)-pyrimidin-4-yl]-methyl-amine (Step 8.2) and 98 μl (0.70 mMol) $Et_3N$ in 4 ml $CH_2Cl_2$ is added during 5 min. After 2.5 h at rt, the mixture is diluted with sat. $Na_2CO3/H_2O$ 1:1 and EtOAc, the aqueous phase separated off and extracted twice with EtOAc. The organic layers are washed with water and brine, dried ($Na_2SO_4$) and concentrated. Crystallization from THF and hexane gives the title compound: m.p.: 180-182° C.; MS: [M+1]$^+$=460; TLC (EtOAc): $R_f$=0.38; HPLC: $^B t_{Ret}$=12.7.

The starting material is prepared as follows:

Step 8.1: 7-(6-Methylamino-pyrimidin-4-yloxy)-2,3-dihydro-benzo[1,4]oxazine-4-carboxylic acid benzyl ester To a suspension of 1.39 g (3.49 mMol) 7-(6-chloro-pyrimidin-4-yloxy)-2,3-dihydro-benzo[1,4]oxazine-4-carboxylic acid benzyl ester (Step 5.4) in 8 ml THF, 8.7 ml (2 M in THF; 17.5 mMol) methylamine are added. After stirring in a sealed vessel for 16 h at rt, the resulting mixture is dissolved with EtOAc and MeOH. Then 6 g of $SiO_2$ are added and the mixture is concentrated in vacuo. The resulting powder is put on top of a $SiO_2$ column (EtOAc/hexane 1:3) and the title compound eluted with EtOAc/hexane 1:3-1:1-2:1: MS: [M+1]$^+$=393; TLC(EtOAc/hexane 1:1): $R_f$=0.08; HPLC: $^A t_{Ret}$=12.1.

Step 8.2: [6-(3,4-Dihydro-2H-benzo[1,4]oxazin-7-yloxy)-pyrimidin-4-yl]-methyl-amine A solution of 0.79 g (2.0 mMol) 7-(6-methylamino-pyrimidin-4-yloxy)-2,3-dihydro-benzo[1,4]oxazine-4-carboxylic acid benzyl ester in 50 ml THF is hydrogenated in the presence of 0.35 g Pd/C (10%; Engelhard 4505). The catalyst is filtered off, the filtrate concentrated partially and the title compound crystallized by addition of hexane: m.p.: 153° C.; MS: [M+1]$^+$=259; TLC(EtOAc): $R_f$=0.16; HPLC: $^B t_{Ret}$=10.6.

Example 9

7-(6-Methylamino-pyrimidin-4-yloxy)-2,3-dihydro-benzo[1,4]oxazine-4-carboxylic acid (3-trifluoromethyl-phenyl)-amide Prepared analogously to Ex. 7: m.p.: 180° C.; MS: [M+1]$^+$=446; TLC(EtOAc): $R_f$=0.47; HPLC: $^A t_{Ret}$=12.3; Anal.: C,H,N,F.

Example 10

7-(2-Amino-pyrimidin-4-yloxy)-2,3-dihydro-benzo[1,4]oxazine-4-carboxylic acid (3-trifluoromethyl-phenyl)-amide A solution of 0.183 g (0.75 mMol) 4-(3,4-dihydro-2H-benzo[1,4]oxazin-7-yloxy)-pyrimidin-2-ylamine (Step 10.2) in 3 ml of acetonitrile is treated at rt with 0.114 ml (0.825 mMol) 1-isocyanato-3-trifluoromethyl-benzene and stirred for 2 h at rt. The solvent is evaporated and the residue chromatographed on a 40 g silica gel column on a Combi-Flash Companion™ (Isco Inc.) apparatus using EtOAc as solvent. The title compound is obtained as a colorless foam: MS: [M+1]$^+$=432; TLC(EtOAc): $R_f$=0.31; HPLC: $^C t_{Ret}$=1.88 min.

The starting material is prepared as follows:

Step 10.1: 7-(2-amino-6-chloro-pyrimidin-4-yloxy)-2,3-dihydro-benzo[1,4]oxazine-4-carboxylic acid benzyl ester To a solution of 5.8 g (0.0203 Mol) crude 7-hydroxy-2,3-dihydro-benzo[1,4]oxazine-4-carboxylic acid benzyl ester (Step 5.3) in 30 ml of DMF are added 2.0 g anhydrous potassium carbonate and 3.3 g (0.0201 Mol) 2-amino-4,6-dichloropyrimidine and the resulting mixture is heated to 80° C. for 16 h. After cooling to rt the mixture is filtered and the DMF evaporated to leave a dark brown oil. This material is purified by flash-chromatography on a 240 g silica gel column using $CH_2Cl_2$/MeOH 100:0.5→100:2.5 as eluent. Pure fractions are evaporated to leave a yellow oil. On addition of 15 ml of EtOAc the product crystallizes. It is filtered off, washed with EtOAc/hexane 1:1 and dried. The title compound is obtained as colorless crystals: m.p.: 161-163° C.; MS: [M+1]$^+$=412.9; TLC ($CH_2Cl_2$/MeOH/$NH_3^{aq}$ 350:50:1): $R_f$=0.76; HPLC: $^C t_{Ret}$=2.57 min.

Step 10.2: 4-(3,4-dihydro-2H-benzo[1,4]oxazin-7-yloxy)-pyrimidin-2-ylamine 2.0 g (4.8 mMol) 7-(2-amino-6-chloro-pyrimidin-4-yloxy)-2,3-dihydro-benzo[1,4]oxazine-4-carboxylic acid benzyl ester are dissolved in 100 ml of a 1:1 mixture of THF and methanol and hydrogenated at rt in the presence of 0.5 g Pd/C (10%; Engelhard 4505). The catalyst is filtered off, the filtrate concentrated and partitioned between 40 ml conc. sodium bicarbonate and 50 ml of EtOAc. The organic layer is washed with brine, dried with sodium sulfate and evaporated. The crude title compound is obtained as an amorphous material: MS: [M+1]$^+$=245; TLC($CH_2Cl_2$/MeOH/$NH_3^{aq}$ 350:50:1): $R_f$=0.47; HPLC: $^C t_{Ret}$=0.86

Example 11

7-(2-Amino-pyrimidin-4-yloxy)-2,3-dihydro-benzo[1,4]oxazine-4-carboxylic acid (4-morpholin-4-ylmethyl-3-trifluoromethyl-phenyl)-amide A solution of 0.86 ml (7.13 mMol) trichloromethyl chloroformate in 4 ml of dry THF is treated at 40° C. with a solution of 0.51 g (2.09 mMol) 4-(3,4-dihydro-2H-benzo[1,4]oxazin-7-yloxy)-pyrimidin-2-ylamine. The mixture is stirred under reflux for 2 h, cooled to rt and evaporated to leave a tan foam. This is added to a solution of 4-morpholin-4-ylmethyl-3-trifluoromethyl-phenylamine (0.362 g, 1.4 mMol) in 4 ml of ethanol. The mixture is heated to 80° C. and stirred at that temperature for 3 h. After cooling to rt the solvent is evaporated and the residue partitioned between $CH_2Cl_2$ and sat. sodium bicarbonate solution. The organic phase is dried with sodium sulfate and evaporated. The residue is purified on a 40 g silica gel column on a Combi-Flash Companion™ (Isco Inc.) apparatus using EtOAc for 10 min, then a gradient of 1 to 30% acetone in EtOAc. The title compound is obtained as a slightly reddish foam: MS: [M+1]$^+$=531; TLC (EtOAc): $R_f$=0.10; HPLC: $^C t_{Ret}$=1.32 min.

Example 12

The following compounds can be obtained analogously to Ex. 10 or 11.

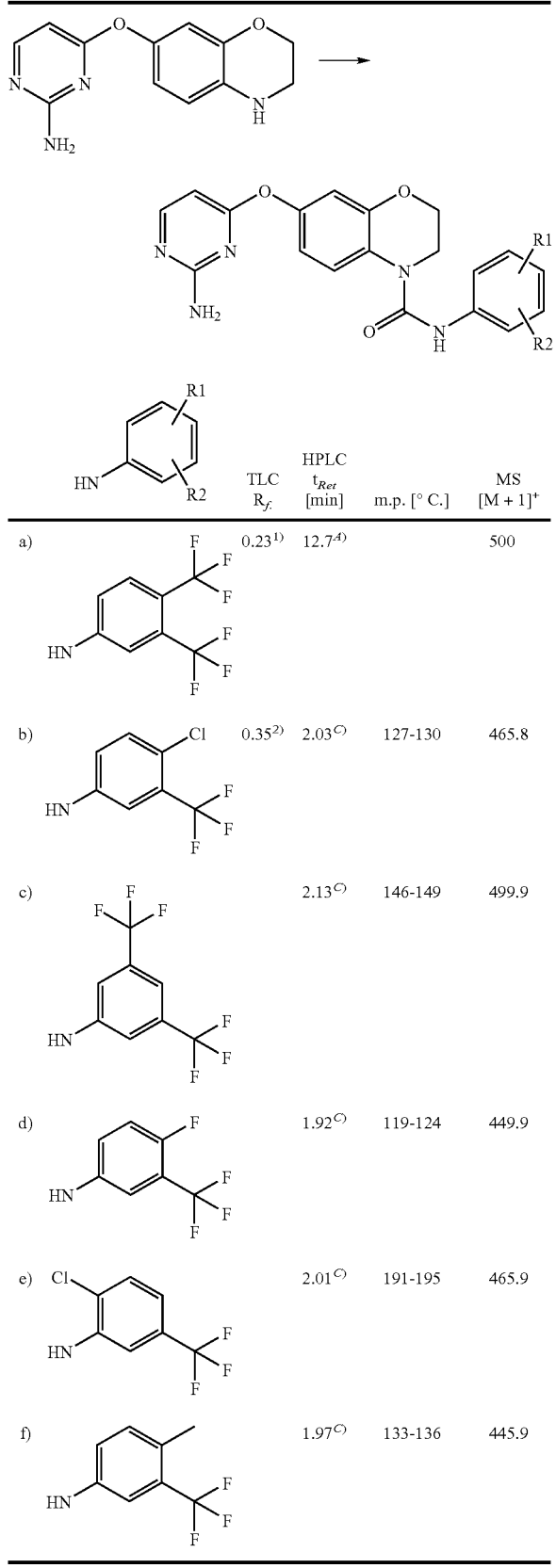

| | R1/R2 aryl | TLC $R_f$ | HPLC $t_{Ret}$ [min] | m.p. [°C.] | MS [M+1]+ |
|---|---|---|---|---|---|
| a) | 3-amino-4,α,α,α-trifluoromethyl (2 CF3) | 0.23[1] | 12.7[4] | | 500 |
| b) | 4-Cl, 3-CF3 | 0.35[2] | 2.03[C] | 127-130 | 465.8 |
| c) | 3,5-bis-CF3 | | 2.13[C] | 146-149 | 499.9 |
| d) | 4-F, 3-CF3 | | 1.92[C] | 119-124 | 449.9 |
| e) | 4-Cl, 3-CF3 | | 2.01[C] | 191-195 | 465.9 |
| f) | 4-Me, 3-CF3 | | 1.97[C] | 133-136 | 445.9 |

[1])TLC(EtOAc/hexane 2:1);
[2])TLC(EtOAc)

Example 13

6-(2-Amino-6-chloro-pyrimidin-4-yloxy)-naphthalene-1-carboxylic acid (3-trifluoromethyl-phenyl)-amide To an ice cooled solution of 3.5 g (11 mMol) 6-(2-amino-6-chloro-pyrimidin-4-yloxy)-naphthalene-1-carboxylic acid in 60 ml DMF, 1.8 ml (16 mMol) NMM and 3.1 ml (20 mMol) DEPC are added, followed by 1.5 ml (12 mMol) of 3-amino-benzotrifluoride. After 2 h stirring at 0° C. and 16 h at rt, the solution is concentrated in vacuo. The residue is re-dissolved in water and EtOAc, the aqueous phase separated off and extracted twice with EtOAc. The organic layers are washed twice with water and brine, dried (Na$_2$SO$_4$) and after addition of SiO$_2$ concentrated. The resulting powder is put on top of a SiO$_2$ column (EtOAc/hexane 1:9) and eluted with EtOAc/hexane 1:9-1:1. Partial concentration of the product containing fractions leads to crystallization. Filtration and washing with hexane gives the title compound: m.p.: 234-236° C.; MS: [M+1]+=459; TLC(EtOAc/hexane 1:2): R$_f$=0.24; HPLC: $^A$t$_{Ret}$=16.2.

The starting material is prepared as follows:

Step 13.1: 6-(2-Amino-6-chloro-pyrimidin-4-yloxy)-naphthalene-1-carboxylic acid A suspension of 6.56 g (40 mMol) 2-amino-4,6-dichloro-pyrimidine and 7.52 g (40 mMol) 6-hydroxy-1-naphthoic acid in 160 ml acetone and 80 ml 1 N NaOH$^{aq}$ is heated to 62° C. for 36 h. The mixture is cooled to rt, partially concentrated in vacuo and the residue poured into 1.6 l icewater. Under vigorous stirring, 20 ml 2 N HCl are added dropwise (pH≈4). After stirring the suspension for 30 min, the title compound is filtered off and washed with water: MS: [M+1]+=316/318; HPLC: $^A$t$_{Ret}$=12.8.

Example 14

6-(2-Amino-pyrimidin-4-yloxy)-naphthalene-1-carboxylic acid (3-trifluoromethyl-phenyl)-amide A solution of 660 mg (1.44 mMol) 6-(2-amino-6-chloro-pyrimidin-4-yloxy)-naphthalene-1-carboxylic acid (3-trifluoromethyl-phenyl)-amide in 70 ml THF and 0.22 ml (1.58 mMol) Et$_3$N is hydrogenated in the presence of 0.4 g Pd/C (10%; Engelhard 4505). The catalyst is filtered off, the filtrate concentrated and the residue diluted with EtOAc and H$_2$O. The aqueous layer is extracted twice with EtOAc. The organic layers are washed with water and brine, dried (Na$_2$SO$_4$) and concentrated. Chromatography (Combi Flash; hexane/EtOAc 1:1→EtOAc) gives the title compound: m.p.: 218° C.; MS: [M+1]+=425; TLC(EtOAc/hexane 1:1): R$_f$=0.07.

Example 15

6-(2-Amino-pyrimidin-4-yloxy)-naphthalene-1-carboxylic acid (4-methyl-3-trifluoromethyl-phenyl)-amide To an ice cooled solution of 140 mg (0.50 mMol) 6-(2-amino-pyrimidin-4-yloxy)-naphthalene-1-carboxylic acid in 3 ml DMF, 78 µl (97%; 0.53 mMol) 4-methyl-3-trifluoromethyl-aniline, 74 µl (0.67 mMol) NMM and 124 µl (0.83 mMol) DEPC are added. After overnight stirring, the mixture is poured into water and EtOAc, the aqueous phase separated off and extracted twice with EtOAc. The organic layers are washed with water and brine, dried (Na$_2$SO$_4$) and concentrated. Chromatography (Combi Flash; hexane/EtOAc 4:1→1:9) and crystallization from hexane gives the title compound: MS: [M+1]$^+$=439; TLC(EtOAc): R$_f$=0.49; HPLC: $^A$t$_{Ret}$=12.7.

The starting material is prepared as follows:

Step 15.1: 6-(2-Amino-pyrimidin-4-yloxy)-naphthalene-1-carboxylic acid

A solution of 230 mg (0.73 mMol) 6-(2-amino-6-chloro-pyrimidin-4-yloxy)-naphthalene-1-carboxylic acid (Step 13.1) in 41 ml THF and 1 ml Et$_3$N is hydrogenated in the presence of 0.17 g Pd/C (10%; Engelhard 4505). The catalyst is filtered off and the filtrate concentrated. The residue is dissolved in EtOAc and H$_2$O and the aqueous layer extracted twice with EtOAc. Acidification of the aqueous phase with 2 N HCl (→pH 3-4) leads to the crystallization of the title compound, which is filtered off and washed with water: MS: [M+1]$^+$=282; HPLC: $^B$t$_{Ret}$=13.6.

Example 16

6-(2-Amino-pyrimidin-4-yloxy)-naphthalene-1-carboxylic acid (2-trifluoromethyl-Pyridin-4-yl)-amide 0.24 mMol 6-(2-Amino-pyrimidin-4-yloxy)-naphthalene-1-carboxylic acid, 43 mg (0.26 mMol) 4-amino-2-(trifluoromethyl)pyridine [*J. Med. Chem.* 36 (1993), 733-746], 20 mg (0.16 mMol) DMAP and 0.8 ml (5.7 mMol) Et$_3$N are dissolved in 4 ml DMF. Then 0.6 ml (1 mMol) propylphosphonic anhydride are added and the mixture is stirred for 3 days at rt. The mixture is poured into water and EtOAc, the aqueous phase separated off and extracted twice with EtOAc. The organic layers are washed with water and brine, dried (Na$_2$SO$_4$) and concentrated. Reversed phase chromatography gives the title compound: MS: [M+1]$^+$=426; HPLC: $^A$t$_{Ret}$=11.9.

Example 17

The following compounds can be obtained analogously to Ex. 15.

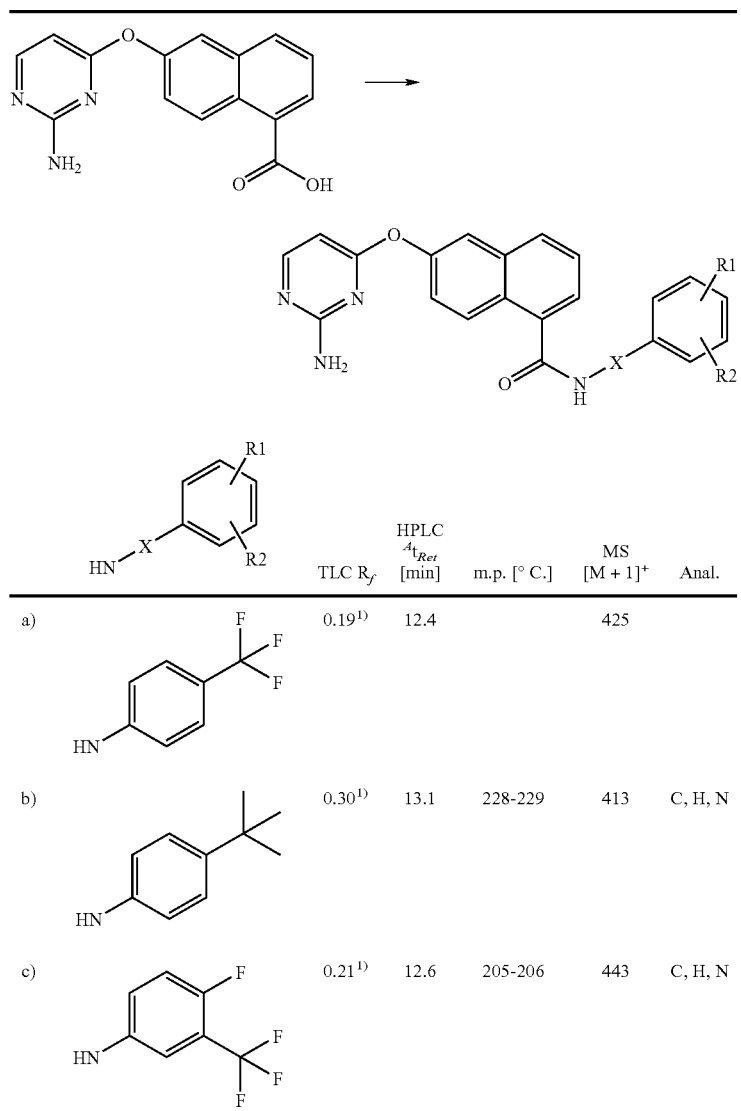

| | | TLC R$_f$ | HPLC $^A$t$_{Ret}$ [min] | m.p. [° C.] | MS [M + 1]$^+$ | Anal. |
|---|---|---|---|---|---|---|
| a) | | 0.19[1)] | 12.4 | | 425 | |
| b) | | 0.30[1)] | 13.1 | 228-229 | 413 | C, H, N |
| c) | | 0.21[1)] | 12.6 | 205-206 | 443 | C, H, N |

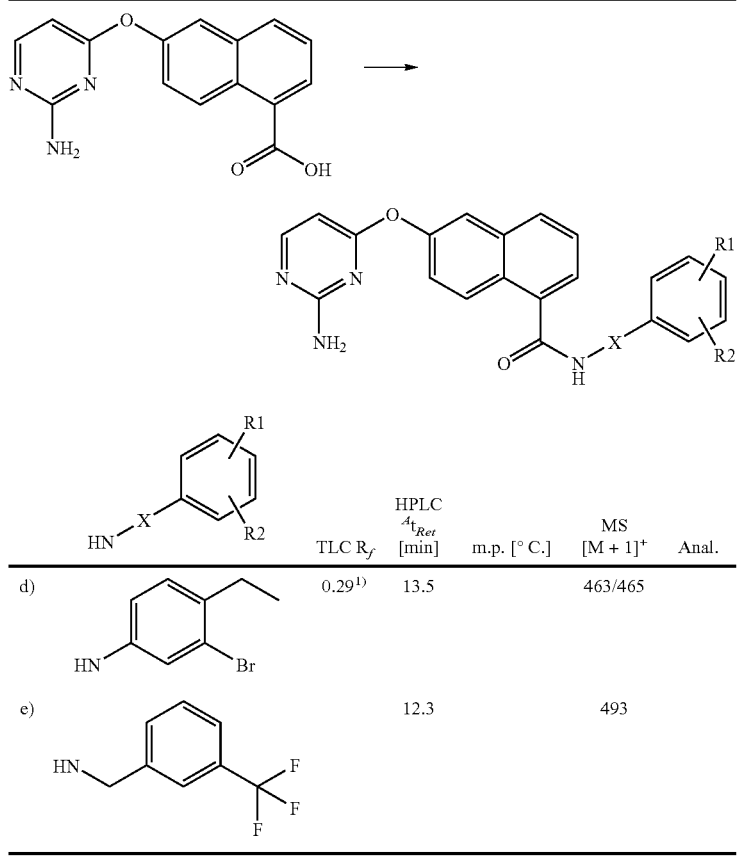

| | TLC R$_f$ | HPLC $^A$t$_{Ret}$ [min] | m.p. [° C.] | MS [M + 1]$^+$ | Anal. |
|---|---|---|---|---|---|
| d) | 0.29$^{1)}$ | 13.5 | | 463/465 | |
| e) | | 12.3 | | 493 | |

$^{1)}$TLC(EtOAc/hexane 2:1)

Example 18

6-(2-Acetylamino-pyrimidin-4-yloxy)-naphthalene-1-carboxylic acid (3-trifluoromethyl-phenyl)-amide A solution of 170 mg (0.40 mMol) 6-(2-amino-pyrimidin-4-yloxy)-naphthalene-1-carboxylic acid (3-trifluoromethyl-phenyl)-amide (Ex. 14) in 3 ml pyridine is diluted with 2 ml CH$_2$Cl$_2$. Then 0.20 ml of an acetylchloride solution (2.2 M in CH$_2$Cl$_2$; 0.44 mMol) are added dropwise, followed by another 0.10 ml after 40 min. After totally 75 min, the reaction mixture is diluted with EtOAc and H$_2$O. The aqueous layer is separated off and extracted twice with EtOAc. The organic layers are washed with water and brine, dried (Na$_2$SO$_4$) and concentrated. Chromatography (Combi Flash; hexane/EtOAc 1:1→EtOAc), partial concentration and crystallization by addition of DIPE gives the title compound: m.p.: 216-217° C.; MS: [M+1]$^+$=467; TLC(EtOAc): R$_f$=0.36; HPLC: $^A$t$_{Ret}$=13.1; Anal.: C,H,N,F.

Example 19

6-(2-Methoxycarbonylamino-pyrimidin-4-yloxy)-naphthalene-1-carboxylic acid (3-trifluoromethyl-phenyl)-amide A solution of 200 mg (0.47 mMol) 6-(2-amino-pyrimidin-4-yloxy)-naphthalene-1-carboxylic acid (3-trifluoromethyl-phenyl)-amide (Ex. 14) in 5 ml pyridine is diluted with 3 ml CH$_2$Cl$_2$. Then 7.1 ml of a methyl chloroformate solution (2.8 M in CH$_2$Cl$_2$; 20 mMol) are added portionwise during 7 h. The reaction mixture is diluted with EtOAc and H$_2$O. The aqueous layer is separated off and extracted twice with EtOAc. The organic layers are washed with water and brine, dried (Na$_2$SO$_4$) and concentrated. Stirring in DIPE gives the title compound: m.p.: 199-200° C.; MS: [M+1]$^+$=483; HPLC: $^A$t$_{Ret}$=13.6; Anal.: C,H,N,F.

Example 20

7-(2-Acetylamino-pyrimidin-4-yloxy)-2,3-dihydro-benzo[1,4]oxazine-4-carboxylic acid (4-methyl-3-trifluoromethyl-phenyl)-amide Prepared at 0° C. as described in Ex. 18 from 161 mg (0.36 mMol) 7-(2-amino-pyrimidin-4-yloxy)-2,3-dihydro-benzo[1,4]oxazine-4-carboxylic acid (4-methyl-3-trifluoromethyl-phenyl)-amide (Ex. 12f): MS: [M+1]$^+$=488; TLC(EtOAc): R$_f$=0.47; HPLC: $^A$t$_{Ret}$=12.9; Anal.: C,H,N,F.

Example 21

7-(2-Methoxycarbonylamino-pyrimidin-4-yloxy)-2,3-dihydro-benzo[1,4]oxazine-4-carboxylic acid (4-methyl-3-trifluoromethyl-phenyl)-amide Prepared as described in Ex. 19 from 150 mg (0.34 mMol) 7-(2-amino-pyrimidin-4-yloxy)-2,3-dihydro-benzo[1,4]oxazine-4-carboxylic acid (4-methyl-3-trifluoromethyl-phenyl)-amide (Ex. 12f): MS: [M+1]$^+$=504; TLC(EtOAc): R$_f$=0.52; HPLC: $^A$t$_{Ret}$=13.3; Anal.: C,H,N,F.

Example 22

7-(2-Amino-pyrimidin-4-yloxy)-2,3-dihydro-benzo[1,4]oxazine-4-carboxylic acid [4-(4-methyl-piperazin-1-yl methyl)-3-trifluoromethyl-phenyl]-amide A solution of 0.174 g (0.71 mMol) 4-(3,4-dihydro-2H-benzo[1,4]oxazin-7-yloxy)-pyrimidin-2-ylamine (Step 10.2) and 0.291 g (0.68 mMol) [4-(4-methyl-piperazin-1-ylmethyl)-3-trifluoromethyl-phenyl]-carbamic acid phenyl ester hydrochloride in 0.75 ml of DMSO is warmed to 60° C. After the addition of 0.133 ml (0.77 mMol) of N,N-diisopropyl-ethylamine the mixture is stirred at 60° C. for 1.5 h. A solution of 0.055 g potassium hydroxide in 0.1 ml of water is added at 50° C. and the mixture stirred rapidly for about 10 min. After cooling to rt the mixture is partitioned between EtOAc and water and the organic layer washed with brine. 2 g of silica gel are added and the solvent evaporated. The resulting powder is applied to a 40 g silica gel column on a Combi-Flash Companion™ (Isco Inc.) apparatus and eluted with EtOAc (A) and MeOH/NH3$^{aq}$ 10:3 (B) with a gradient of 0% B→10% B in 30 min then 10% B for 20 min. The title compound is obtained as a yellowish foam: MS: [M+1]$^+$=543.9; TLC (CH$_2$Cl$_2$/MeOH/NH$_3$$^{aq}$ 350:50:1): R$_f$=0.36; HPLC: $^C$t$_{Ret}$=1.30 min.

The starting material is prepared as follows:

Step 22.1: [4-(4-Methyl-piperazin-1-ylmethyl)-3-trifluoromethyl-phenyl]-carbamic acid phenyl ester hydrochloride As described in *Synth. Commun.* 30 (2000),1937 the title compound can be prepared by dropwise addition of a solution of [4-(4-methyl-piperazin-1-ylmethyl)-3-trifluoromethyl]-aniline (1.0 eq.) in THF to a solution of phenyl chloroformate (1.1 eq.) in THF at −25° C. and warming the mixture up to rt.

Example 23

6-(2-Amino-pyrimidin-4-yloxy)-naphthalene-1-carboxylic acid (4-morpholin-4-yl-3-trifluoromethyl-phenyl)-amide To a solution of 184 mg (0.65 mMol) 6-(2-amino-pyrimidin-4-yloxy)-naphthalene-1-carboxylic acid (Step 15.1) in 5 ml NMP, 214 µl (1.95 mMol) NMM and 247 mg (0.65 mMol) HATU are added. After 15 min stirring, 242 mg (0.98 mMol) 4-morpholin-4-yl-3-trifluoromethyl-aniline are added, followed by some DMAP. After 16 h, the mixture is poured into water and EtOAc, the aqueous phase separated off and extracted twice with EtOAc. The organic layers are washed with sat. Na$_2$CO$_3$/H$_2$O 1:1, water and brine, dried (Na$_2$SO$_4$) and concentrated. Chromatography (Combi Flash; hexane/EtOAc 4:1→1:9) and crystallization from EtOAc/hexane gives the title compound: MS: [M+1]$^+$=510; TLC(EtOAc/hexane 2:1): R$_f$=0.17; HPLC: $^A$t$_{Ret}$=12.5.

Example 24

6-(2-Amino-pyrimidin-4-yloxy)-naphthalene-1-carboxylic acid cis/trans-(4-isopropyl-cyclohexyl)-amide To an ice cooled solution of 180 mg (0.47 mMol) 6-(2-amino-pyrimidin-4-yloxy)-naphthalene-1-carboxylic acid (Step 15.1) in 5 ml DMF, 69 µl (0.63 mMol) NMM and 118 µl (0.79 mMol) DEPC are added, followed by 133 mg (0.94 mMol) cis/trans-(4-isopropyl-cyclohexyl)-amine [*Arzneim. Forsch.* 19 (1969), 140]. After 16 h stirring, the mixture is poured into water and EtOAc, the aqueous phase separated off and extracted twice with EtOAc. The organic layers are washed with water and brine, dried (Na$_2$SO$_4$) and concentrated. Chromatography (Combi Flash; CH$_2$Cl$_2$/EtOAc 9:1→3:2) gives the title compound as a cis/trans mixture: MS: [M+1]$^+$=405; TLC(CH$_2$Cl$_2$/EtOAc 1:1): R$_f$=0.18; HPLC: $^A$t$_{Ret}$=13.6.

Example 25

6-(6-Amino-pyrimidin-4-yloxy)-naphthalene-1-carboxylic acid (4-fluoro-3-trifluoromethyl-phenyl)-amide To an ice cooled solution of 120 mg (0.43 mMol) 6-(6-amino-pyrimidin-4-yloxy)-naphthalene-1-carboxylic acid (Step 25.3) in 3 ml DMF, 63 µl (0.57 mMol) NMM and 107 µl (0.72 mMol) DEPC are added, followed by 111 µl (0.86 mMol) 4-fluoro-3-trifluoromethyl-aniline. The solution is stirred for 1 h at 0° C. and 5 h at rt. Then it is poured into water and EtOAc, the aqueous phase separated off and extracted twice with EtOAc. The organic layers are washed with water and brine, dried (Na$_2$SO$_4$) and concentrated. Chromatography (Combi Flash; hexane/EtOAc 4:1→1:9) and crystallization from hexane gives the title compound: m.p.: 224-225° C.; MS: [M+1]$^+$=443; TLC(EtOAc): R$_f$=0.38; HPLC: $^A$t$_{Ret}$=12.5.

The starting material is prepared as follows:

Step 25.1: 6-(6-Chloro-pyrimidin-4-yloxy)-naphthalene-1-carboxylic acid 23.6 g (125 mMol) 6-hydroxy-1-naphthoic acid are dissolved in a solution of 10.7 g (265 mMol) NaOH in 125 ml water. Then 19.8 g (133 mMol) 4,6-dichloro-pyrimidine dissolved in 125 ml acetone are added dropwise during 30 min. The suspension is stirred for 20 h at rt and then partially concentrated in vacuo. The resulting residue is diluted with 600 ml EtOAc and 300 ml water and acidified to pH 3 with 4 N HCl. The aqueous layer is separated off and extracted 3 times with EtOAc. The organic phases are washed 3 times with water and brine, dried (Na$_2$SO$_4$), treated with char coal and partially concentrated. The resulting suspension is diluted with 400 ml ether, the crystals filtered off and washed with hexane, yielding the title compound: m.p.: 194-195° C.; MS: [M+1]$^+$=301.

Step 25.2: 6-(6-Azido-pyrimidin-4-yloxy)-naphthalene-1-carboxylic acid

To 1.00 g (3.3 mMol) 6-(6-chloro-pyrimidin-4-yloxy)-naphthalene-1-carboxylic acid in 11 ml DMF, 0.43 g (6.6 mMol) NaN$_3$ are added. After stirring for 2.5 h at 60° C., the reaction mixture is concentrated in vacuo (40° C.). The residue is dissolved in water and EtOAc, the aqueous phase separated off and extracted twice with EtOAc. The organic layers are washed with brine, dried (Na$_2$SO$_4$) and concentrated, giving the title compound: MS: [M+1]$^+$=308; HPLC: $^A$t$_{Ret}$=13.4. More product can be precipitated from the combined aqueous phases by acidifying them with citric acid to pH≈2.

Step 25.3: 6-(6-Amino-pyrimidin-4-yloxy)-naphthalene-1-carboxylic acid 0.49 g (1.6 mMol) 6-(6-azido-pyrimidin-4-yloxy)-naphthalene-1-carboxylic acid in 25 ml THF are hydrogenated in the presence of 0.2 g Pd/C (10%; Engelhard 4505). The partially crystallized product can be isolated by dissolving it in a mixture of MeOH/EtOAc/THF at 40° C., filtration, extensively washing with MeOH/CH$_2$Cl$_2$, and concentration of the filtrate: m.p.: 288-290° C.; MS: [M+1]$^+$=282; HPLC: $^A$t$_{Ret}$=8.6.

Alternative method for synthesis of 6-(6-amino-pyrimidin-4-yloxy)-naphthalene-1-carboxylic acid 1.00 g (3.3 mMol) 6-(6-Chloro-pyrimidin-4-yloxy)-naphthalene-1-carboxylic acid and 0.43 g (6.6 mMol) NaN$_3$ are stirred for 2 h at 65° C. in 11 ml DMF. The suspension is cooled to rt, 200 mg Pd/C (10%; Engelhard 4505) are added and the mixture is hydrogenated for 16 h. The catalyst is filtered off and the filtrate concentrated in vacuo. The residue is re-dissolved in 5 ml DMF and poured into 150 ml water and 3 ml 10% citric acid. Filtration and washing with water gives the title compound.

Example 26

6-(6-Amino-pyrimidin-4-yloxy)-naphthalene-1-carboxylic acid (3-trifluoromethyl-phenyl)-amide To a solution of 11.0 g (39.1 mMol) 6-(6-amino-pyrimidin-4-yloxy)-naphthalene-1-carboxylic acid, 5.9 ml (47 mMol) 3-trifluoromethyl-aniline, 54 ml (390 mMol) Et$_3$N and 2.4 g (19.6 mMol) DMAP in 200 ml DMF, 46 ml (78 mMol) propylphosphonic anhydride are added dropwise. After 2 h, the mixture is concentrated in vacuo and the residue diluted with water and EtOAc. The aqueous phase is separated off and extracted twice with EtOAc. The organic layers are washed with water and brine, dried (Na$_2$SO$_4$) and concentrated. Column chromatography (SiO$_2$; CH$_2$Cl$_2$/EtOAc 2:1→1:1→1:3) and crystallization from EtOAc gives the title compound: m.p.: 243-244° C.; MS: [M+1]$^+$=425; HPLC: $^A$t$_{Ret}$=12.6; Anal.: C,H,N,F

Example 27

6-(6-Chloro-pyrimidin-4-yloxy)-benzooxazole-3-carboxylic acid (3-trifluoromethyl-phenyl)-amide To a solution of 300 mg (0.92 mMol) 6-hydroxy-benzooxazole-3-carboxylic acid (3-trifluoromethyl-phenyl)-amide (Step 27.3) and 138 mg (0.92 mMol) 4,6-dichlorpyrimidine in 9 ml acetone, 0.92 ml NAOH$^{aq.}$ 1 N are added. Then the mixture is stirred for 120 min at 50° C. and concentrated in vacuo. The residue is dissolved in EtOAc and water, the aqueous phase separated off and extracted twice with EtOAc. The organic layers are washed with water and brine, dried (Na$_2$SO$_4$) and concentrated. Chromatography (Combi Flash; hexane/EtOAc 85:15→4:1) gives the title compound: MS: [M+1]$^+$=437; TLC(hexane/EtOAc 1:1): R$_f$=0.42; HPLC: $^A$t$_{Ret}$=15.9.

The starting material is prepared as follows:

Step 27.1: 1-(4-Benzyloxy-2-hydroxy-phenyl)-3-(3-trifluoromethyl-phenyl)-urea To a solution of 4.44 g (20.6 mMol) 2-amino-5-benzyloxy-phenol [preparation see: WO 03/045925; page 146] in 90 ml THF, a solution of 3.01 ml (21.9 mMol) 3-trifluoromethyl-phenylisocyanat in 90 ml THF is added dropwise. After 15 h at rt, the reaction mixture is concentrated partially in vacuo, the residue is re-dissolved in water and EtOAc, the aqueous phase separated off and extracted twice with EtOAc. The organic layers are washed with water and brine, dried (Na$_2$SO$_4$) and concentrated. The crude product is dissolved in 50 ml boiling EtOAc. Addition of 40 ml hexane and cooling to rt gives the crystalline title compound: m.p.: 184-185° C.; MS: [M+1]$^+$=403; HPLC: $^A$t$_{Ret}$=15.3.

Step 27.2: 6-Benzyloxy-benzooxazole-3-carboxylic acid (3-trifluoromethyl-phenyl)-amide To a solution of 6.80 g (16.9 mMol) of 1-(4-benzyloxy-2-hydroxy-phenyl)-3-(3-trifluoromethyl-phenyl)-urea in 100 ml DMF, 11.9 ml (0.17 Mol) dibromo-methane are added, followed by small portions of 19.3 g (59 mMol) of Cs$_2$CO$_3$. After 10 h at rt, the reaction mixture is concentrated in vacuo and the residue dissolved in EtOAc and a 10% citric acid solution. The separated aqueous phase is extracted twice with EtOAc. The organic layers are washed with water and brine, dried (Na$_2$SO$_4$) and concentrated. The dark brown oil is dissolved in CH$_2$Cl$_2$/MeOH, then 28 g of SiO$_2$ are added and the mixture is evaporated. The resulting powder is put on top of a chromatography column (SiO$_2$; hexane/EtOAc 3:1) and the title compound eluated with hexane/EtOAc 3:1 as an oil: MS: [M+1]$^+$=415; TLC(hexane/EtOAc 1:1): R$_f$=0.59; HPLC: $^A$t$_{Ret}$=17.2.

Step 27.3: 6-Hydroxy-benzooxazole-3-carboxylic acid (3-trifluoromethyl-phenyl)-amide As a solution in 60 ml THF, 1.67 g (4.0 mMol) 6-benzyloxy-benzooxazole-3-carboxylic acid (3-trifluoromethyl-phenyl)-amide are hydrogenated in the presence of 0.9 g Pd/C (10%; Engelhard 5125). The catalyst is filtered off, washed with THF and the filtrate diluted with hexane. Partial concentration leads to the crystalline title compound, which is filtered off and washed with hexane: m.p.: 173-174° C.; MS: [M+1]$^+$=325; HPLC: $^A$t$_{Ret}$=13.3.

Example 28

6-(6-Amino-pyrimidin-4-yloxy)-benzooxazole-3-carboxylic acid (3-trifluoromethyl-phenyl)-amide 150 mg (0.34 mMol) 6-(6-Chloro-pyrimidin-4-yloxy)-benzooxazole-3-carboxylic acid (3-trifluoromethyl-phenyl)-amide and 45 mg (0.69 mMol) NaN$_3$ in 2 ml DMF are stirred for 5 h at 60° C. giving 6-(6-azido-pyrimidin-4-yloxy)-benzooxazole-3-carboxylic acid (3-trifluoromethyl-phenyl)-amide (MS: [M+1]$^+$=444). After cooling to rt, 35 mg Pd/C (10%; Engelhard 4505) are added and the mixture is hydrogenated for 30 min. The catalyst is filtered off, washed with DMF and the filtrate concentrated in vacuo. Chromatography (Combi Flash; hexane/EtOAc 1:1→EtOAc) gives the title compound: MS: [M+1]$^+$=418; TLC(EtOAc: R$_f$=0.25; HPLC: $^A$t$_{Ret}$=12.0.

Example 29

6-(6-Methylamino-pyrimidin-4-yloxy)-benzooxazole-3-carboxylic acid (3-trifluoromethyl-phenyl)-amide In a sealed tube, 0.43 mMol of 6-(6-chloro-pyrimidin-4-yloxy)-benzooxazole-3-carboxylic acid (3-trifluoromethylphenyl)-amide in 2 ml THF and 2 ml methylamine (2 N in THF) are stirred for 16 h at rt. Concentration, chromatography (Combi Flash; $CH_2Cl_2$/MeOH 99:1→95:5) and crystallization from hexane gives the title compound: MS: $[M+1]^+$= 432; TLC($CH_2Cl_2$/MeOH 9:1: $R_f$=0.34; HPLC: $^At_{Ret}$=12.5.

Example 30

6-(2-Amino-6-chloro-pyrimidin-4-yloxy)-benzooxazole-3-carboxylic acid (3-trifluoromethyl-phenyl)-amide To an ice cooled solution of 300 mg (0.92 mMol) 6-hydroxy-benzooxazole-3-carboxylic acid (3-trifluoromethyl-phenyl)-amide (Step 27.3) and 151 mg (0.92 mMol) 2-amino-4,6-dichlorpyrimidine in 8 ml DMF, 600 mg (1.84 mMol) $Cs_2CO_3$ are added. Then the mixture is stirred for 4 h at rt and 1.5 h at 40° C. and finally concentrated in vacuo. The residue is dissolved in EtOAc and water/brine 1:1. The separated aqueous phase is extracted twice with EtOAc. The organic layers are washed with water/brine 1:1 and brine, dried ($Na_2SO_4$) and concentrated. Chromatography (Combi Flash; $CH_2Cl_2$/MeOH 99:1→95:5) gives the title compound: MS: $[M+1]^+$=452/454; TLC($CH_2Cl_2$/MeOH 9:1): $R_f$=0.51; HPLC: $^At_{Ret}$=15.3.

Example 31

6-(2-Amino-pyrimidin-4-yloxy)-benzooxazole-3-carboxylic acid (3-trifluoromethyl-phenyl)-amide Hydrogenation of 38 mg 6-(2-amino-6-chloro-pyrimidin-4-yloxy)-benzooxazole-3-carboxylic acid (3-trifluoromethyl-phenyl)-amide as described in Ex. 14 gives the title compound: MS: $[M+1]^+$=418; HPLC: $^At_{Ret}$=12.5.

Example 31A 6-(6-Chloro-pyrimidin-4-yloxy)-benzooxazole-3-carboxylic acid (4-fluoro-3-trifluoromethyl-phenyl)-amide To a solution of 650 mg (1.90 mMol) 6-hydroxy-benzooxazole-3-carboxylic acid (4-fluoro-3-trifluoromethyl-phenyl)-amide in 15 ml acetone, 2.5 ml 1 N $NAOH^{aq}$ are dropped in followed by a solution of 325 mg (2.18 mMol) 4,6-dichlorpyrimidine in 5 ml acetone. After 75 min the reaction mixture is concentrated in vacuo and the residue dissolved in EtOAc, water and brine. The aqueous phase is separated off and extracted twice with EtOAc. The organic layers are washed with 2 portions of water/brine 1:1 and brine, dried ($Na_2SO_4$) and concentrated. Chromatography (Combi Flash; $CH_2Cl_2$/EtOAc 97:3→9:1) gives the title compound: MS: $[M+1]^+$=455/457; TLC($CH_2Cl_2$/EtOAc 9:1): $R_f$=0.26; HPLC: $^At_{Ret}$=16.3.

The starting material is prepared as follows:

Step 31A.: 1-(4-Benzyloxy-2-hydroxy-phenyl)-3-(4-fluoro-3-trifluoromethyl-phenyl)-urea To a solution of 3.01 g (14 mMol) 2-amino-5-benzyloxy-phenol [preparation see: WO 03/045925; page 146] in 60 ml THF, a solution of 2.11 ml (14.8 mMol) 4-fluoro-3-trifluoromethyl-phenylisocyanate in 50 ml THF is added dropwise. After 1.5 h at rt, the reaction mixture is concentrated partially in vacuo, the residue is re-dissolved in water and EtOAc. The organic layers are separated off and washed with water and brine, dried ($Na_2SO_4$) and concentrated to a volume of ≈80 ml. Addition of 50 ml hexane gives the crystalline title compound: m.p.: 188-191° C.; MS: $[M+1]^+$=421; TLC(hexane/EtOAc 1:1): $R_f$=0.31.

Step 31A.2: 6-Benzyloxy-benzooxazole-3-carboxylic acid (4-fluoro-3-trifluoromethyl-phenyl)-amide 12.5 g (38.3 mMol) $Cs_2CO_3$ are added to a solution of 4.6 g (10.9 mMol) 1-(4-benzyloxy-2-hydroxy-phenyl)-3-(4-fluoro-3-trifluoromethyl-phenyl)-urea in 100 ml DMF, followed by 7.6 ml (109 mMol) $CH_2Br_2$. This dark green mixture is stirred for 13 h at rt and 70 min at 50° C. Then it is concentrated in vacuo and the residue re-dissolved in EtOAc and a 10% citric acid solution. The separated aqueous phase is extracted twice with EtOAc. The organic layers are washed with 2 portions of water and brine, dried ($Na_2SO_4$) and after addition of $SiO_2$ concentrated. The resulting powder is put on top of a chromatography column ($SiO_2$) and the title compound eluated with hexane/EtOAc 4:1: m.p.: 144-146° C.; MS: [M−1]=431; TLC(hexane/EtOAc 1:1): $R_f$=0.57.

Step 31A.3: 6-Hydroxy-benzooxazole-3-carboxylic acid (4-fluoro-3-trifluoromethyl-phenyl)-amide Hydrogenation of 1.69 g (3.91 mMol) 6-benzyloxy-benzooxazole-3-carboxylic acid (4-fluoro-3-trifluoromethyl-phenyl)-amide in 60 ml THF in the presence of 0.85 g Pd/C (10%; Engelhard 5125), filtration, partial concentration of the filtrate, dilution with ≈15 ml hexane and cooling to 0° C. gives the crystalline title compound: m.p.: 171-172° C.; MS: [M−1]=341; HPLC: $^At_{Ret}$=13.7.

Example 31B 6-(6-Amino-pyrimidin-4-yloxy)-benzooxazole-3-carboxylic acid (4-fluoro-3-trifluoromethyl-phenyl)-amide 50 mg (0.11 mMol) 6-(6-Chloro-pyrimidin-4-yloxy)-benzooxazole-3-carboxylic acid (4-fluoro-3-trifluoromethyl-phenyl)-amide and 14.3 mg (0.22 mMol) $NaN_3$ in 1.5 ml DMF are stirred for 5 h at 60° C. giving 6-(6-azido-pyrimidin-4-yloxy)-benzooxazole-3-carboxylic acid (4-fluoro3-trifluoromethyl-phenyl)-amide (MS: [M−1]=460). After cooling to rt, 13 mg Pd/C (10%; Engelhard 4505) are added and the mixture is hydrogenated over night. The catalyst is filtered off, washed with DMF and the filtrate concentrated in vacuo. Chromatography (Combi Flash; $CH_2Cl_2$/EtOAc 3:2→EtOAc) gives the title compound: MS: $[M+1]^+$=436; TLC(EtOAc: $R_f$=0.22; HPLC: $^At_{Ret}$=12.5.

Example 32

6-(2-Amino-6-chloro-pyrimidin-4-yloxy)-naphtha-lene-1-carboxylic acid (3-trifluoromethyl-4-chloro-phenyl)-amide To an ice cooled solution of 161 mg (0.51 mMol) 6-(2-amino-6-chloro-pyrimidin-4-yloxy)-naphthalene-1-carboxylic acid (Step 13.1) in 5 ml DMF, 75 μl (0.68 mMol) NMM and 127 μl (0.85 mMol) DEPC are added, followed by 0.30 g (1.5 mMol) of 2-chloro-5-amino-benzotrifluoride and a catalytic amount of DMAP. After 20 h stirring at rt, the solution is poured into water and EtOAc, the aqueous phase separated off and extracted twice with EtOAc. The organic layers are washed with water and brine, dried ($Na_2SO_4$) and concentrated. Column chromatography (SiO₂; EtOAc/hexane 2:8→3:7) and partial concentration of the product containing fractions leads to crystallization. Filtration and washing with hexane gives the title compound: MS: [M+1]⁺=493/495; HPLC: $^A t_{Ret}$=16.7.

Example 32A 6-(2-Amino-6-chloro-pyrimidin-4-yloxy)-benzooxazole-3-carboxylic acid (4-fluoro-3-trifluoromethyl-phenyl)-amide 231 mg (0.675 mMol) 6-hydroxy-benzooxazole-3-carboxylic acid (4-fluoro-3-trifluoromethyl-phenyl)-amide (Step 31A.3) and 122 mg (0.742 mMol) 2-amino-4,6-dichloropyrimidine are dissolved in 7 ml DMF. Then 440 mg (1.35 mMol) Cs₂CO₃ are added and the mixture is stirred for 24 h at rt. After concentration in vacuo, the residue is re-dissolved in EtOAc and water/brine 1:1. The aqueous layer is separated off and extracted twice with EtOAc. The organic phases are washed with water/brine 1:1 and brine, dried (Na₂SO₄) and concentrated. Chromatography (Combi Flash; CH₂Cl₂/THF 97:3→9:1) gives the title compound: MS: [M+1]⁺=470/472; TLC(CH₂Cl₂/THF 9:1: $R_f$=0.30; HPLC: $^A t_{Ret}$=15.7.

Example 32B 6-(2-Amino-pyrimidin-4-yloxy)-benzooxazole-3-carboxylic acid (4-fluoro-3-trifluoromethyl-phenyl)-amide A solution of 59 mg (0.126 mMol) 6-(2-amino-6-chloro-pyrimidin-4-yloxy)-benzooxazole-3-carboxylic acid (4-fluoro-3-trifluoromethyl-phenyl)-amide and 0.17 ml (1.2 mMol) Et₃N in 6 ml THF is hydrogenated in presence of 25 mg Pd/C (Engelhard 4505). The mixture is filtered, the filtrate concentrated and the residue re-dissolved in EtOAc and water. The aqueous layer is separated off and extracted twice with EtOAc. The organic phases are washed with water and brine, dried (Na₂SO₄) and partially concentrated. Addition of DIPE gives the crystalline title compound: MS: [M+1]⁺=436; HPLC: $^A t_{Ret}$=12.6.

Example 33

6-(2-Amino-pyrimidin-4-yloxy)-naphthalene-1-carboxylic acid (3-trifluoromethyl-4-chloro-phenyl)-amide A solution of 100 mg (0.20 mMol) 6-(2-amino-6-chloro-pyrimidin-4-yloxy)-naphthalene-1-carboxylic acid (3-trifluoromethyl-4-chloro-phenyl)-amide in 10 ml THF and 31 µl (0.22 mMol) Et₃N is hydrogenated in the presence of 40 mg Pd/C (10%; Engelhard 4505). The catalyst is filtered off, the filtrate concentrated and the residue diluted with EtOAc and H₂O. The aqueous layer is extracted twice with EtOAc. The organic layers are washed with water and brine, dried (Na₂SO₄) and concentrated. Reversed phase MPLC gives the title compound: MS: [M+1]⁺=459; HPLC: $^A t_{Ret}$=13.3.

Examples 34(a)-(b)

Via analogous routes (see Ex. 46-50) the following derivatives can be obtained:

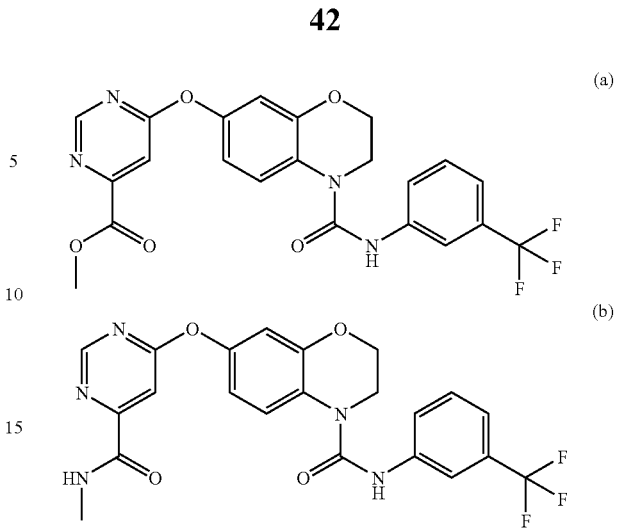

Example 35

6-(2-Amino-pyrimidin-4-yloxy)-naphthalene-1-carboxylic acid [4-(4-methyl-piperazin-1-yl-methyl)-3-trifluoromethyl-phenyl]-amide To a solution of 50 mg (0.178 mMol) 6-(2-amino-pyrimidin-4-yloxy)-naphthalene-1-carboxylic acid (Step 15.1) and 53 mg (0.19 mMol) 4-(4-methyl-piperazin-1-yl-methyl)-3-trifluoromethyl-aniline in 2 ml DMF, 198 µl (1.42 mMol) Et₃N, 156 µl (0.267 mMol) propylphosphonic anhydride and 10 mg DMAP are added. After 3 days, the mixture is poured into water and EtOAc, the aqueous phase separated off and extracted twice with EtOAc. The organic layers are washed with water and brine, dried (Na₂SO₄) and concentrated. Reversed phase chromatography and crystallization from DIPE/hexane gives the title compound: MS: [M+1]⁺=537; TLC(EtOAc/EtOH/NH₃$^{aq}$ 80:20:1): $R_f$=0.38; HPLC: $^A t_{Ret}$=9.2; Anal.: C,H,N,F.

Example 36

6-(2-Amino-pyrimidin-4-yloxy)-naphthalene-1-carboxylic acid [3,4-bis(trifluoromethyl)-phenyl]-amide To a solution of 100 mg (0.356 mMol) 6-(2-amino-pyrimidin-4-yloxy)-naphthalene-1-carboxylic acid (Step 15.1) and 89.6 mg (0.39 mMol) 3,4-bis(trifluoromethyl)-aniline in 4 ml DMF, 396 µl (2.75 mMol) Et₃N, 312 µl (0.53 mMol) propylphosphonic anhydride and 10 mg DMAP are added. After 16 h, the mixture is poured into water and EtOAc, the aqueous phase separated off and extracted twice with EtOAc. The organic layers are washed with water and brine, dried (Na₂SO₄) and concentrated. Chromatography (Combi Flash; EtOAc/hexane 1:1→EtOAc) gives the title compound: MS: [M+1]⁺=493; TLC(EtOAc): $R_f$=0.54; HPLC: $^A t_{Ret}$=12.6.

Example 37

The following compounds can be obtained analogously to Ex. 35 and 36.

Starting material: 2-amino-4-[(naphthalen-6-yl)oxy]pyrimidine-naphthalene-1-carboxylic acid → amide products with various anilines (R1, R2 substituents).

| | HN-Ar (R1/R2) | TLC $R_f$ | HPLC $^A t_{Ret}$ [min] | m.p. [°C] | MS [M + 1]$^+$ | Anal. |
|---|---|---|---|---|---|---|
| a) | 3-(SF$_5$)phenyl-NH– | 0.37[1] | 13.4 | | 483 | |
| b) | 2-methyl-2H-indazol-5-yl-NH– | | 10.2 | | 411 | |
| c) | 2-methyl-2H-indazol-6-yl-NH– | | 10.1 | | 411 | |
| d) | 1,1,3,3-tetrafluoro-1,3-dihydroisobenzofuran-5-yl-NH– | 0.35[1] | 13.6 | | 471 | |
| e) | 3-tert-butylphenyl-NH– | 0.20[2] | 13.8 | 182–184 | 413 | C, H, N |
| f) | 3-chloro-5-(trifluoromethyl)phenyl-NH– | 0.43[3] | 14.2 | 210 | 459/461 | |
| g)*) | 3-cyclopropylphenyl-NH– | 0.44[4] | 12.9 | 217 | 397 | C, H, N |

-continued
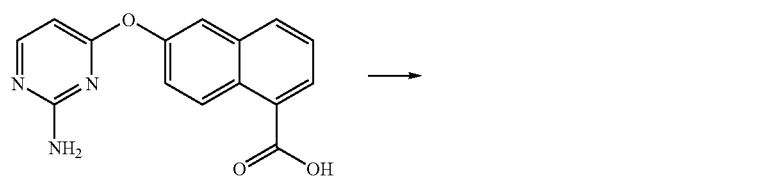
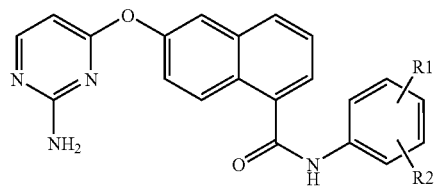
| | | TLC $R_f$ | HPLC $^A t_{Ret}$ [min] | m.p. [° C.] | MS [M + 1]$^+$ | Anal. |
|---|---|---|---|---|---|---|
| h) | HN—⟨phenyl⟩—ethyl | 0.23$^{5)}$ | 11.2 | 228 | 385 | C, H, N |
| i) **) | HN—⟨phenyl(F, cyclopropyl)⟩ | 0.13$^{5)}$ | 12.9 | 236-237 | 415 | |
| j) ***) | HN—⟨phenyl⟩—CF$_2$CH$_3$ | 0.28$^{5)}$ | 12.3 | 212 | 421 | C, H, N, F |
| k) | HN—⟨phenyl⟩—OCF$_3$ | 0.19$^{5)}$ | 12.9 | 212-213 | 441 | |
| l) | HN—⟨phenyl(OMe, OMe)⟩ | 0.17$^{5)}$ | 11.5 | 179 | 417 | |

US 8,026,247 B2

-continued

| | | TLC $R_f$ | HPLC $t_{Ret}$ [min] | m.p. [° C.] | MS [M + 1]$^+$ | Anal. |
|---|---|---|---|---|---|---|
| m) | | 0.16[5] | 12.9 | | 417 | C, H, N |
| n) | | 0.30[5] | 10.2 | 275-276 | 403 | |
| o) | | 0.43[6] | 9.2 | 171-172 | 309 | C, H, N |

[1] TLC(EtOAc);
[2] TLC(hexane/EtOAc 1:3);
[3] TLC(EtOAc/CH$_2$Cl$_2$ 9:1);
[4] TLC(EtOAc/CH$_2$Cl$_2$ 4:1);
[5] TLC(CH$_2$Cl$_2$/EtOH 19:1)
[6] TLC(CH$_2$Cl$_2$/EtOH 9:1)
*) 3-cyclopropyl-aniline see: Tet. Lett. 43 (2002), 6987;
**) 3-cyclopropyl-4-fluor-aniline prepared from 3-brom-2-fluor-aniline analogously to the procedure described in Tet. Lett. 43 (2002), 6987: TLC(hexane/EtOAc 4:1): $R_f$ = 0.15;
***) 3-(α,α-difluorethyl)-aniline see: DE2130452 Ex. 12b

Example 38

6-(6-Amino-pyrimidin-4-yloxy)-naphthalene-1-carboxylic acid (3-cyclopropyl-4-fluoro-phenyl)-amide To a solution of 267 mg (0.95 mMol) 6-(6-amino-pyrimidin-4-yloxy)-naphthalene-1-carboxylic acid (Step 25.3) and 172 mg (1.14 mMol) 3-cyclopropyl-4-fluor-aniline in 5 ml DMF, 1.32 ml (9.5 mMol) Et$_3$N, 1.11 ml (1.9 mMol) propylphosphonic anhydride and 51 mg DMAP are added. After 1 h, the mixture is poured into water and EtOAc, the aqueous phase separated off and extracted twice with EtOAc. The organic layers are washed with water and brine, dried (Na$_2$SO$_4$) and concentrated. Chromatography (Combi Flash; CH$_2$Cl$_2$/EtOH 99:1→ 19:1) gives the title compound: mp.: 256-257° C.; Anal.: C,H,N,F.

Example 39

The following compounds can be obtained analogously to Ex. 38 (eventually longer reaction times necessary).

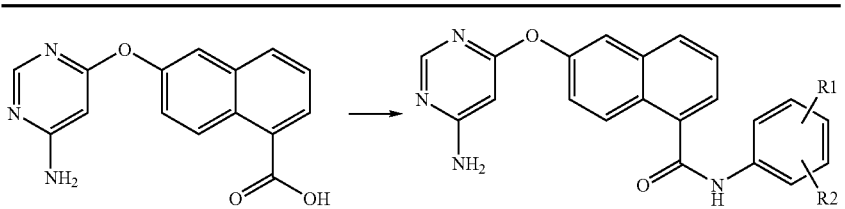
| | R1/R2 aniline | TLC $R_f$ | HPLC $^A t_{Ret}$ [min] | m.p. [°C.] | MS $[M+1]^+$ | Anal. |
|---|---|---|---|---|---|---|
| a) | 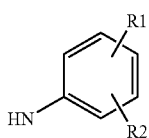 | 0.23[1] | 14.1 | | 493 | |
| b) | 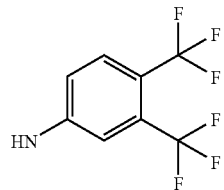 | 0.37[2] | 14.0 | 222-223 | 459/461 | |
| c) | 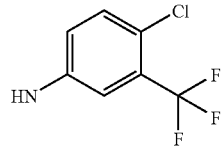 | 0.28[2] | 13.8 | 272 | 439 | |
| d) | 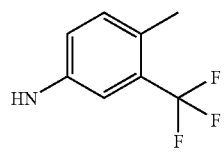 | 0.40[3] | 9.7 | | 551 | |
| e) | 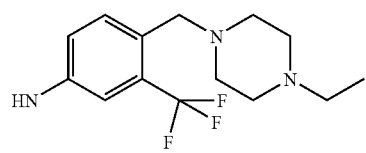 | 0.35[2] | 12.5 | 267 | 371 | C, H, N |
| f) | 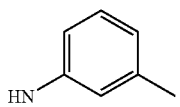 | 0.29[2] | 13.7 | 218-219 | 399 | C, H, N |
| g) | 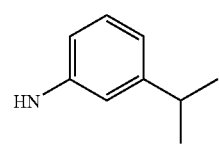 | 0.45[2] | 14.3 | 186-187 | 413 | C, H, N |

-continued
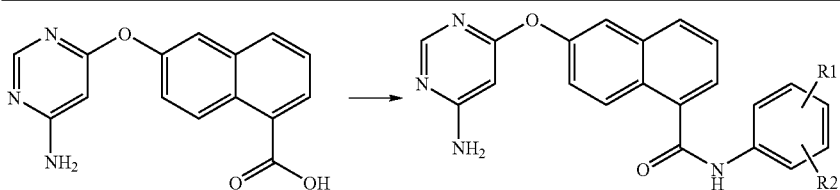
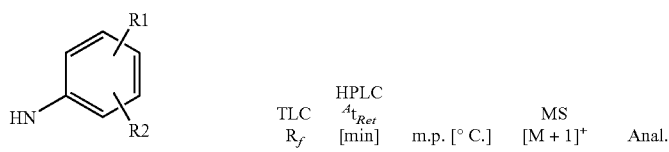
| | | TLC $R_f$ | HPLC $^At_{Ret}$ [min] | m.p. [° C.] | MS $[M + 1]^+$ | Anal. |
|---|---|---|---|---|---|---|
| h) | 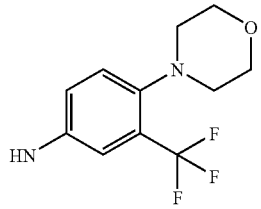 | $0.22^{3)}$ | 13.6 | | 510 | |
| i) | *) 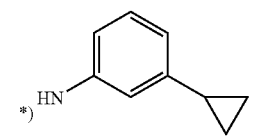 | $0.28^{4)}$ | 12.9 | 246 | 397 | C, H, N |
| j) | 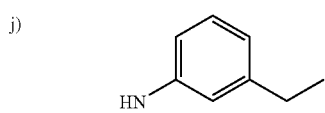 | $0.09^{5)}$ | 11.3 | 251-252 | 385 | C, H, N |
| k) | **) 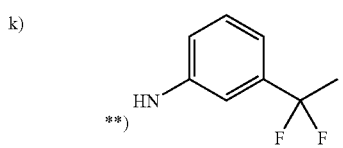 | $0.27^{4)}$ | 12.4 | 250-251 | 421 | C, H, N, F |
| l) | 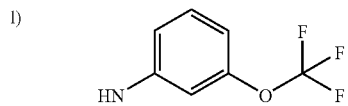 | $0.15^{5)}$ | 13.0 | 239-240 | 441 | C, H, N, F |
| m) | 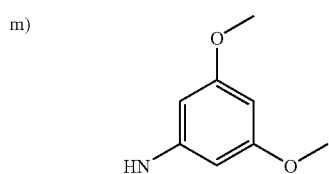 | $0.18^{5)}$ | 11.8 | 182-183 | 417 | C, H, N |

-continued

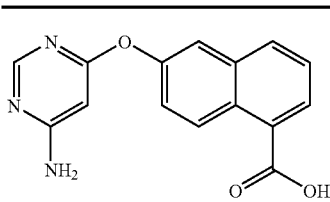

| | | TLC $R_f$ | HPLC $^At_{Ret}$ [min] | m.p. [° C.] | MS [M + 1]$^+$ | Anal. |
|---|---|---|---|---|---|---|
| n) | 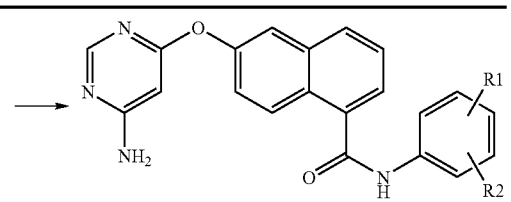 | 0.36$^{2)}$ | 13.6 | | 417 | |
| o) | 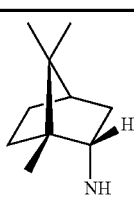 | | 10.6 | 217-219 | 403 | |
| p) | 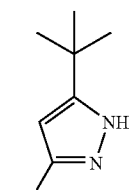 | | 10.6 | | 394 | C, H, N |

$^{1)}$TLC(EtOAc/CH$_2$Cl$_2$ 1:1);
$^{2)}$TLC(EtOAc/CH$_2$Cl$_2$ 9:1);
$^{3)}$TLC(EtOAc/EtOH/NH$_3^{aq}$ 80:20:1);
$^{4)}$TLC(EtOAc/CH$_2$Cl$_2$ 4:1);
$^{5)}$TLC(CH$_2$Cl$_2$/EtOH 19:1)
*) 3-cyclopropyl-aniline see: Tet. Lett. 43 (2002), 6987;
**) 3-(α,α-difluorethyl)-aniline see: DE2130452 Ex. 12b Example 40

6-(6-Methylamino-pyrimidin-4-yloxy)-naphthalene-1-carboxylic acid (4-morpholin-4-yl-3-trifluoromethyl-phenyl)-amide To a solution of 295.3 mg (1.00 mMol) 6-(6-methylamino-pyrimidin-4-yloxy)-naphthalene-1-carboxylic acid and 295 mg (1.2 mMol) 4-morpholin-4-yl-3-trifluoromethyl-aniline in 5 ml DMF, 1.39 ml (10 mMol) Et$_3$N, 1.17 ml (2.0 mMol) propylphosphonic anhydride and 50 mg (0.4 mMol) DMAP are added. After 30 min, the mixture is poured into water and EtOAc, the aqueous phase separated off and extracted 3 times with EtOAc. The organic layers are washed 3 times with water and brine, dried (Na$_2$SO$_4$) and concentrated. Column chromatography (SiO$_2$; CH$_2$Cl$_2$/EtOH 95:5) gives the title compound: mp.: 156-157° C.; MS: [M+1]$^+$=524.

The starting material is prepared as follows:

Step 40.1: 6-(6-Methylamino-pyrimidin-4-yloxy)-naphthalene-1-carboxylic acid

To a solution of 8.1 g (27 mMol) 6-(6-chloro-pyrimidin-4-yloxy)-naphthalene-1-carboxylic acid (Step 25.1) in 100 ml THF, 200 ml of a 2 M solution of methylamin in THF are added. After 3 days at rt, the suspension is concentrated partially in vacuo, the solid filtered off and washed with ether. The crude product dissolved in 300 ml water is treated with char coal and filtered. The filtrate is acidified to pH 1 with 1 N HCl and the formed precipitate filtered off, washed with water and dried. Repeated stirring in ether followed by filtration gives the title compound: m.p.: 267-268° C.; MS: [M+1]$^+$= 296.

Example 41

The following compounds can be obtained analogously to Ex. 40.

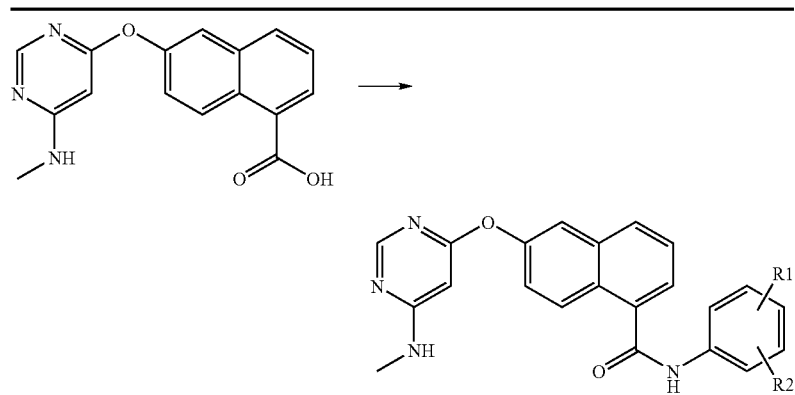
| | TLC $R_f$ | HPLC $A_{t_{Ret}}$ [min] | m.p. [° C.] | MS $[M + 1]^+$ | Anal. |
|---|---|---|---|---|---|
| a) 3-CF₃-phenyl | 0.29¹⁾ | 11.7 | 152-153 | 439 | |
| b) 4-F-3-CF₃-phenyl | 0.26¹⁾ | 11.9 | 154-155 | 457 | |
| c) 3-tBu-phenyl | 0.22¹⁾ | 12.5 | 102-104 | 427 | |
| d) 4-tBu-phenyl | 0.30¹⁾ | 12.6 | 141-142 | 427 | |
| e) 4-Cl-3-CF₃-phenyl | 0.22¹⁾ | 12.5 | 148-149 | 473/475 | |
| f) 4-Me-3-CF₃-phenyl | 0.22¹⁾ | 12.2 | 238-239 | 453 | |
| g) 4-(4-methylpiperazin-1-ylmethyl)-3-CF₃-phenyl | 0.23²⁾ | 8.5 | | 551 | |

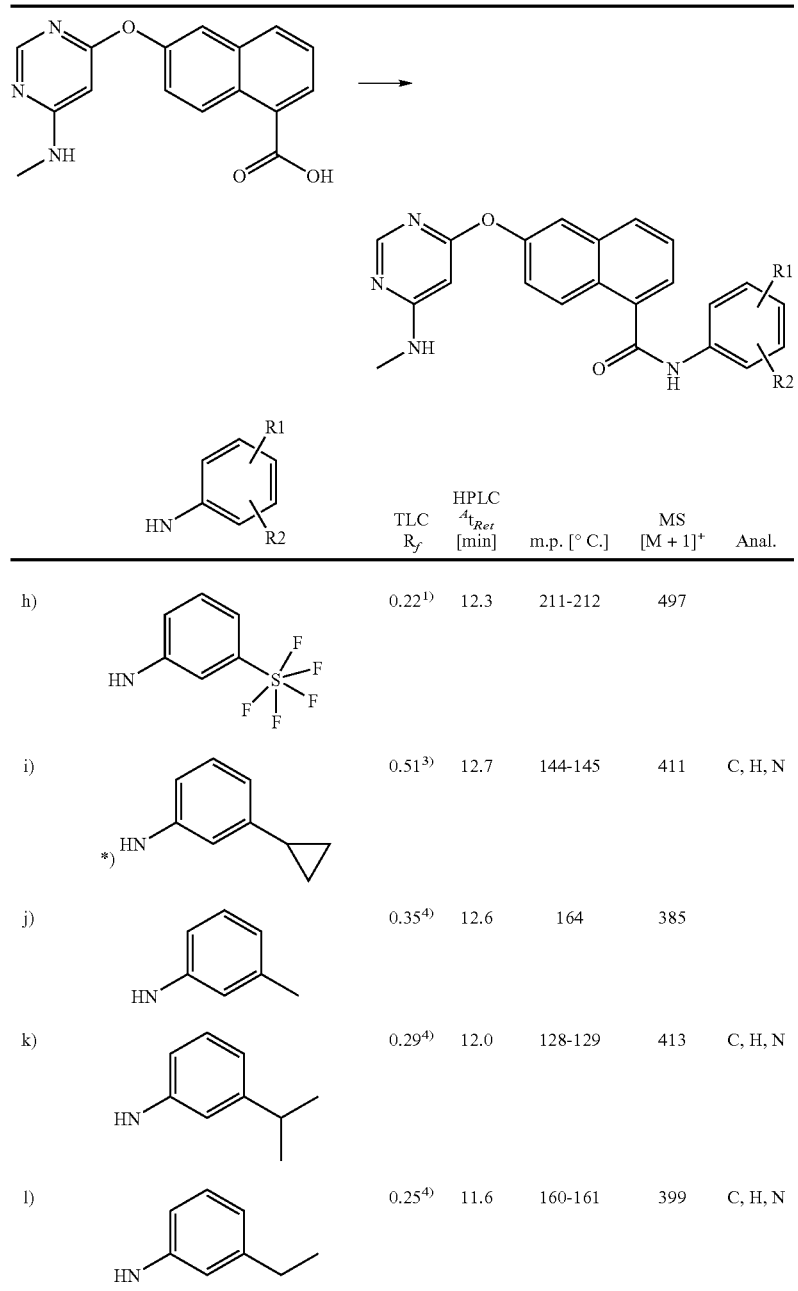

| | HN-R1/R2 | TLC $R_f$ | HPLC $^A t_{Ret}$ [min] | m.p. [° C.] | MS [M + 1]$^+$ | Anal. |
|---|---|---|---|---|---|---|
| h) | HN-C6H4-SF5 | 0.22[1)] | 12.3 | 211-212 | 497 | |
| i)*) | HN-C6H4-cyclopropyl | 0.51[3)] | 12.7 | 144-145 | 411 | C, H, N |
| j) | HN-C6H4-CH3 | 0.35[4)] | 12.6 | 164 | 385 | |
| k) | HN-C6H4-iPr | 0.29[4)] | 12.0 | 128-129 | 413 | C, H, N |
| l) | HN-C6H4-Et | 0.25[4)] | 11.6 | 160-161 | 399 | C, H, N |

[1)]TLC(CH$_2$Cl$_2$/MeOH 19:1);
[2)]TLC(CH$_2$Cl$_2$/MeOH/NH$_3^{aq}$ 90:10:1);
[3)]TLC(CH$_2$Cl$_2$/acetone 2:1);
[4)]TLC(CH$_2$Cl$_2$/EtOH 19:1)
*) 3-cyclopropyl-aniline see: Tet. Lett. 43 (2002), 6987

Example 42

6-(6-Chloro-pyrimidin-4-yloxy)-naphthalene-1-carboxylic acid (3-trifluoromethyl-phenyl)-amide To 8.38 g (27.9 mMol) 6-(6-chloro-pyrimidin-4-yloxy)-naphthalene-1-carboxylic acid (Step 25.1), 31 ml (223 mMol) Et$_3$N and 1 g (8 mMol) DMAP in 100 ml ice-cooled DMF, 24.4 ml (41.8 mMol) propylphosphonic anhydride in 25 ml DMF are added dropwise during 20 min, followed by a solution of 3.83 ml (30.6 mMol) 3-trifluormethyl-aniline in 25 ml DMF. After 90 min at rt, the mixture is concentrated partially in vacuo at 40° C. The resulting residue is diluted with water and EtOAc, the aqueous phase separated off and extracted twice with EtOAc. The organic layers are washed with water and brine, dried (Na$_2$SO$_4$) and concentrated. Column chromatography (SiO$_2$; CH$_2$Cl$_2$/THF 99:1→CH$_2$Cl$_2$/THF/Et$_3$N 98:1:1) gives the title compound: MS: [M+1]$^+$= 444; TLC(CH$_2$Cl$_2$/THF 99:1): R$_f$=0.17; HPLC: $^A t_{Ret}$=16.8.

Example 43

6-(6-Cyano-pyrimidin-4-yloxy)-naphthalene-1-carboxylic acid (3-trifluoromethyl-phenyl)-amide To a solution of 3.3 g (7.4 mMol) 6-(6-chloro-pyrimidin-4-yloxy)-naphthalene-1-carboxylic acid (3-trifluoromethyl-phenyl)-amide in 80 ml DMSO and 20 ml water, 0.42 g (3.7 mMol) 1,4-diazobicyclo[2,2,2]octan and 1.0 g (15 mMol) KCN are added. The mixture is stirred for 30 min at 55° C. and then diluted with water, brine and EtOAc. The aqueous phase is separated off and extracted twice with EtOAc. The organic layers are washed with water and brine, dried ($MgSO_4$) and concentrated. The residue is re-dissolved in $CH_2Cl_2$ and after addition of $SiO_2$ concentrated again. The resulting powder is put on top of a $SiO_2$-column. Eluation with $CH_2Cl_2$/EtOAc 98:2→93:7, partial concentration and crystallization by adding hexane gives the title compound: m.p.: 167° C.; MS: $[M+1]^+$=435; Anal.: C,H,N,F.

Example 44

6-(6-Aminomethyl-pyrimidin-4-yloxy)-naphthalene-1-carboxylic acid (3-trifluoromethyl-phenyl)-amide 830 mg (1.91 mMol) 6-(6-cyano-pyrimidin-4-yloxy)-naphthalene-1-carboxylic acid (3-trifluoromethyl-phenyl)-amide in 40 ml THF and 7.3 ml $NH_3^{aq}$ 25% are hydrogenated in presence of 0.7 g Raney-Nickel (Degussa B 113W). The aqueous layer is separated off from the reaction mixture and extracted with EtOAc. The organic phases are dried ($Na_2SO_4$) and concentrated. This residue is re-dissolved in EtOAc/acetone and after addition of $SiO_2$ concentrated again. The resulting powder is put on top of a $SiO_2$-column. Eluation with EtOAc/acetone/$Et_3N$ 80:20:0→80:20:1→60:40:1, partial concentration and crystallization by adding hexane gives the title compound: MS: $[M+1]^+$=439; TLC(EtOAc/acetone 2:1+$NH_3^{aq}$): $R_f$=0.35; HPLC: $^At_{Ret}$=12.5.

Example 45

{6-[5-(3-Trifluoromethyl-phenylcarbamoyl)-naphthalen-2-yloxy]-pyrimidin-4-ylmethyl}-carbamic acid methylester A mixture of 100 mg (0.23 mMol) 6-(6-aminomethyl-pyrimidin-4-yloxy)-naphthalene-1-carboxylic acid (3-trifluoromethyl-phenyl)-amide, 175 µl (1.2 mMol) $Et_3N$, 60 µl (0.77 mMol) methyl chloroformate and a trace of DMAP in 3 ml THF is stirred over night at rt. The mixture is poured into water and EtOAc, the aqueous phase separated off and extracted twice with EtOAc. The organic layers are washed with water and brine, dried ($Na_2SO_4$) and concentrated. Chromatography (Combi Flash; hexane/EtOAc 7:3→1:1) gives the title compound: MS: $[M+1]^+$=497; TLC(EtOAc/hexane 2:1): $R_f$=0.35; HPLC: $^At_{Ret}$=14.9.

Example 46

6-[5-(3-Trifluoromethyl-phenylcarbamoyl)-naphthalen-2-yloxy]-pyrimidine-4-carboxylic acid ethyl ester A mixture of 5.36 g (12.07 mMol) 6-(6-chloro-pyrimidin-4-yloxy)-naphthalene-1-carboxylic acid (3-trifluoromethyl-phenyl)-amide (Ex. 42), 3.4 ml (24 mMol) $Et_3N$ and 1.35 g $PdCl_2[P(C_6H_5)_3]_2$ in 80 ml ethanol is prepared under a CO-atmosphere of 120 bar in an autoclave. Then it is heated for 30 h at 110° C. After cooling to rt, the mixture is diluted with EtOH and filtered. The residue is washed vigorously with EtOH and the filtrate concentrated. Column chromatography ($SiO_2$; $CH_2Cl_2$/EtOAc 19:1→9:1) and partial concentration leads to the crystalline title compound: m.p.: 194° C.; Anal.: C,H,N,F.

Example 47

6-[5-(3-Trifluoromethyl-phenylcarbamoyl)-naphthalen-2-yloxy]-pyrimidine-4-carboxylic acid To 0.36 g (0.75 mMol) 6-[5-(3-trifluoromethyl-phenylcarbamoyl)-naphthalen-2-yloxy]-pyrimidine-4-carboxylic acid ethyl ester dissolved in 9 ml THF, 1.15 ml 1 M LiOH in water are added. After 2 h at rt, the mixture is concentrated in vacuo. The residue is dissolved in a mixture of EtOAc, water and 1 N NaOH-solution. The aqueous layer is separated off and extracted with EtOAc. The organic phases are washed with a diluted NaOH-solution and discarded. The combined aqueous layers are acidified with 2 N HCl and extracted twice with EtOAc. These organic phases are washed with brine, dried ($Na_2SO_4$) and concentrated. Crystallization from DIPE gives the title compound: MS: $[M+1]^+$=454.

Example 48

6-[5-(3-Trifluoromethyl-phenylcarbamoyl)-naphthalen-2-yloxy]-pyrimidine-4-carboxylic acid dimethylamide To 200 mg (0.435 mMol) of the lithium-salt of 6-[5-(3-trifluoromethyl-phenylcarbamoyl)-naphthalen-2-yloxy]-pyrimidine-4-carboxylic acid, 612 µl (4.4 mMol) $Et_3N$, 24 mg (0.2 mMol) DMAP and 24 mg (0.53 mMol) $Me_2NH$ in 7 ml DMF, 516 µl (0.88 mMol) propylphosphonic anhydride are added. After 2.5 h at rt, the mixture is diluted with water and EtOAc, the aqueous phase separated off and extracted twice with EtOAc. The organic layers are washed with water and brine, dried ($Na_2SO_4$) and concentrated. Chromatography (Combi Flash; hexane/EtOAc 3:2→2:3) gives the title compound: MS: $[M+1]^+$=481; TLC($CH_2Cl_2$/EtOAc 1:1): $R_f$=0.18; HPLC: $^At_{Ret}$=15.8.

Example 49

6-[5-(3-Trifluoromethyl-phenylcarbamoyl)-naphthalen-2-yloxy]-pyrimidine-4-carboxylic acid amide To a solution of 207 mg (0.43 mMol) 6-[5-(3-trifluoromethyl-phenylcarbamoyl)-naphthalen-2-yloxy]-pyrimidine-4-carboxylic acid ethyl ester (Ex. 46) in 12 ml $CH_3CN$ and 5 ml THF, 5 ml of $NH_3$ (25% in water) are added. This mixture is stirred in a sealed vessel for 7 h at rt, while a precipitation is formed. Filtration and washing with $CH_3CN$ yields the title compound: MS: $[M-1]$=451; HPLC: $^At_{Ret}$=15.2; Anal.: C,H,N,F.

Example 50

6-[5-(3-Trifluoromethyl-phenylcarbamoyl)-naphthalen-2-yloxy]-pyrimidine-4-carboxylic acid methylamide To 200 mg (0.435 mMol) of the lithium-salt of 6-[5-(3-trifluoromethyl-phenylcarbamoyl)-naphthalen-2-yloxy]-pyrimidine-4-carboxylic acid, 609 μl (4.35 mMol) Et₃N, 24 mg (0.2 mMol) DMAP and 260 μl (2 M in THF; 0.52 mMol) MeNH₂ in 7 ml DMF, 510 μl (0.87 mMol) propylphosphonic anhydride are added. After 1 h at rt, the mixture is diluted with water and EtOAc, the aqueous phase separated off and extracted twice with EtOAc. The organic layers are washed twice with water and brine, dried (Na₂SO₄) and concentrated. Chromatography (Combi Flash; CH₂Cl₂/EtOAc 4:1) gives the title compound: MS: [M+1]⁺=467; TLC(EtOAc): $R_f$=0.55; HPLC: $^At_{Ret}$=15.7.

Example 51

6-[5-(3-Trifluoromethyl-phenylcarbamoyl)-naphthalen-2-yloxy]-pyrimidine-4-carboxylic acid isopropylamide To a solution of 197 mg (0.41 mMol) 6-[5-(3-trifluoromethyl-phenylcarbamoyl)-naphthalen-2-yloxy]-pyrimidine-4-carboxylic acid ethyl ester (Ex. 46) in 10 ml THF, 7 μl (0.4 mMol) H₂O and 0.7 ml (8 mMol) isopropylamine are added. This mixture is stirred in a sealed vessel for 5 days at 45° C. Reversed phase chromatography gives the title compound: m.p.: 205-208° C.; MS: [M+1]⁺=495; Anal.: C,H,N,F.

Example 52

6-(6-Hydroxymethyl-pyrimidin-4-yloxy)-naphthalene-1-carboxylic acid (3-trifluoromethyl-phenyl)-amide To 1.16 g (2.41 mMol) 6-[5-(3-trifluoromethyl-phenylcarbamoyl)-naphthalen-2-yloxy]-pyrimidine-4-carboxylic acid ethyl ester (Ex. 46) in 40 ml tert-butanol, 218 mg (5.76 mMol) NaBH₄ are added and the mixture is stirred for 1 h at 70° C. Then additional 109 mg NaBH₄ are added and stirring is continued for another 1 h at 80° C. The reaction mixture is concentrated in vacuo and the residue re-dissolved in EtOAc and sat. NaHCO₃. The separated aqueous phase is extracted twice with EtOAc. The organic layers are washed with sat. NaHCO₃ and brine, dried (Na₂SO₄) and concentrated after addition of SiO₂. This powder is put on top of a SiO₂-column (CH₂Cl₂/EtOAc 2:1→1:1→EtOAc): At first the side product 6-(6-methyl-pyrimidin-4-yloxy)-naphthalene-1-carboxylic acid (3-trifluoromethyl-phenyl)-amide is eluated {MS: [M+1]⁺=424; TLC(CH₂Cl₂/EtOAc 1:1): $R_f$=0.33; HPLC: $^At_{Ret}$=15.1}, followed by the title compound: m.p.: 183-184° C.; MS: [M+1]⁺=440; TLC(CH₂Cl₂/EtOAc 1:1): $R_f$=0.13; HPLC: $^At_{Ret}$=14.3; Anal.: C,H,N,F.

Example 53

6-(6-Chloromethyl-pyrimidin-4-yloxy)-naphthalene-1-carboxylic acid (3-trifluoromethyl-phenyl)-amide 1.0 ml (13.9 mMol) SOCl₂ is added via syringe to a solution of 610 mg (1.39 mMol) 6-(6-hydroxymethyl-pyrimidin-4-yloxy)-naphthalene-1-carboxylic acid (3-trifluoromethyl-phenyl)-amide in 50 ml CH₃CN and 10 ml THF. After 15 min at rt, the solution is poured into 75 ml sat. NaHCO₃ and 75 ml water and then concentrated partially in vacuo. The formed precipitate is filtered off and washed with water, yielding the title compound: m.p.: 178-181° C.; MS: [M+1]⁺=458/460; Anal.: C,H,N,F.

Example 54

6-(6-Methylaminomethyl-pyrimidin-4-yloxy)-naphthalene-1-carboxylic acid (3-trifluoromethyl-phenyl)-amide In a sealed tube a mixture of 150 mg (0.328 mMol) 6-(6-chloromethyl-pyrimidin-4-yloxy)-naphthalene-1-carboxylic acid (3-trifluoromethyl-phenyl)-amide, 10 mg (0.067 mMol) NaI and 0.8 ml methylamine (2 M in THF) in 8 ml THF is stirred for 2.5 h at 80° C. The reaction mixture is concentrated in vacuo and the residue re-dissolved in EtOAc and sat. NaHCO3/H₂O 1:1. The separated aqueous phase is extracted twice with EtOAc. The organic layers are washed with sat. NaHCO₃/H₂O 1:1 and brine, dried (Na₂SO₄) and concentrated. Chromatography (Combi Flash; EtOAc/(THF+2% Et₃N) 19:1→1:1) gives the title compound: m.p.: 141-143° C.; MS: [M+1]⁺=453; Anal.: C,H,N.

Example 55

6-(6-Dimethylaminomethyl-pyrimidin-4-yloxy)-naphthalene-1-carboxylic acid (3-trifluoromethyl-phenyl)-amide In a sealed tube a mixture of 150 mg (0.328 mMol) 6-(6-chloromethyl-pyrimidin-4-yloxy)-naphthalene-1-carboxylic acid (3-trifluoromethyl-phenyl)-amide, 134 mg (1.64 mMol) dimethylamine hydrochloride, 10 mg (0.067 mMol) NaI, 687 gl (4.9 mMol) Et₃N and 8 ml THF is stirred for 4.25 h at 80° C. Work up analogously as described for Ex. 54 gives the title compound: m.p.: 180-181° C.; MS: [M+1]⁺=467; Anal.: C,H, N,F.

Example 56

{6-[5-(4-Fluoro-3-trifluoromethyl-phenylcarbamoyl)-naphthalen-2-ylsulfanyl]-pyrimidin-4-yl}-carbamic acid tert-butyl ester To an ice-cooled solution of 127 mg (0.32 mMol) 6-(6-tert-butoxycarbonylamino-pyrimidin-4-ylsulfanyl)-naphthalene-1-carboxylic acid and 86 mg (0.48 mMol) 4-fluoro-3-trifluoromethyl-aniline in 3 ml DMF, 446 μl (3.2 mMol) Et₃N, 0.37 ml (0.63 mMol) propylphosphonic anhydride and 4 mg DMAP are added. After 2 h at rt, the mixture is poured into water and EtOAc, the aqueous phase separated off and extracted twice with EtOAc. The organic layers are washed twice with water and brine, dried (Na₂SO₄) and concentrated. Re-crystallization from boiling CH₃CN gives the title compound: MS: [M+1]⁺=559; TLC(hexane/EtOAc 1:1): $R_f$=0.47; Anal.: C,H,N,F.

The starting material is prepared as follows:

Step 56.1: 6-(6-Chloro-pyrimidin-4-ylsulfanyl)-naphthalene-1-carboxylic acid 894 mg (6.0 mMol) 4,6-Dichloro-pyrimidine and 1021 mg (5.0 mMol) 6-mercapto-naphthalene-1-carboxylic acid [preparation described in *J. Med. Chem.* 32 (1989), 2493; purification by chromatography (Combi Flash; hexane/EtOAc 7:3→3:2): m.p.: 212-213° C.] are suspended in 16 ml acetone. Then 16 ml of 1 N NaOH in H₂O are added. After 5 min at rt, the resulting solution is poured into 200 ml of 1 N HCl in H₂O and extracted 3 times with EtOAc. The organic layers are washed with water and brine, dried (Na₂SO₄) and concentrated. Column chromatography (SiO₂; CH₂Cl₂/

EtOAc 1:2) and crystallization from EtOAc/hexane yields the title compound: m.p.: 209° C.; MS: [M+1]=317.

Step 56.2: 6-(6-tert-Butoxycarbonylamino-pyrimidin-4-ylsulfanyl)-naphthalene-1-carboxylic acid A suspension of 195 mg (0.61 mMol) 6-(6-chloro-pyrimidin-4-ylsulfanyl)-naphthalene-1-carboxylic acid and 495 mg (1.52 mMol) $Cs_2CO_3$ in 5 ml dioxane is degassed repeatedly by evaporation and flushing with $N_2$. Then 10.9 mg (0.019 mMol) 4,5-bis(diphenylphosphino)-9,9-dimethylxanthene, 5.6 mg (0.006 mMol) tris(dibenzylidenaceton)dipalladium (0) $CDCl_3$ adduct and 85.8 mg (0.73 mMol) carbamic acid tert-butyl ester are added successively. After 4 h stirring at 110° C., another 10.9 mg 4,5-bis(diphenylphosphino)-9,9-dimethylxanthene and 5.6 mg tris(dibenzylidenaceton)dipalladium(0) $CDCl_3$ adduct are added and stirring is continued for 5 h. Then the cooled mixture is poured into EtOAc and 5% citric acid in water, the aqueous layer separated off and extracted twice with EtOAc. The organic layers are washed with water and brine, dried ($Na_2SO_4$) and concentrated. Chromatography (Combi Flash; $CH_2Cl_2$/EtOAc 99:1→$CH_2Cl_2$/(EtOAc+1% HOAC) 4:1) gives the title compound: m.p.: 208-209° C.; MS: [M−1]=396.

Example 57

6-(6-Amino-pyrimidin-4-ylsulfanyl)-naphthalene-1-carboxylic acid (4-fluoro-3-trifluoromethyl-phenyl)-amide To a solution of 80 mg (0.14 mMol) {6-[5-(4-fluoro-3-trifluoromethyl-phenylcarbamoyl)-naphthalen-2-ylsulfanyl]-pyrimidin-4-yl}-carbamic acid tert-butyl ester in 2 ml dioxane are added 2 ml 2 M HCl in dioxane. After 9 h at rt, the solution is diluted with EtOAc and sat. NaHCO3/$H_2O$ 1:1. The aqueous phase is separated off and extracted twice with EtOAc. The organic layers are washed with $H_2O$ and brine, dried ($Na_2SO_4$) and concentrated. Chromatography (Combi Flash; $CH_2Cl_2$/EtOAc 4:1→1:4) and crystallization from EtOAc/hexane gives the title compound: m.p.: 221° C.; MS: [M+1]$^+$=459; TLC($CH_2Cl_2$/EtOAc 1:2): $R_f$=0.25.

Example 58

6-(6-Amino-pyrimidin-4-ylsulfanyl)-naphthalene-1-carboxylic acid (3-trifluoromethyl-phenyl)-amide To 1.65 g (5.55 mMol) 6-(6-amino-pyrimidin-4-ylsulfanyl)-naphthalene-1-carboxylic acid, 832 µl (6.66 mMol) 3-trifluoromethyl-aniline, 7.87 ml (56.5 mMol) $Et_3N$ and 291 mg (2.38 mMol) DMAP in 30 ml DMF, 6.8 ml (11.6 mMol) propylphosphonic anhydride are added dropwise. After 1 h at rt, the mixture is poured into water and EtOAc, the aqueous phase separated off and extracted twice with EtOAc. The organic layers are washed with water and brine, dried ($Na_2SO_4$) and concentrated after addition of $SiO_2$. The resulting powder is put on top of a $SiO_2$ column ($CH_2Cl_2$/EtOAc 9:1) and the title compound eluted with $CH_2Cl_2$/EtOAc 4:1→3:7: m.p.: 205° C.; MS: [M+1]$^+$=441; TLC($CH_2Cl_2$/EtOAc 1:1): $R_f$=0.16; HPLC: $^At_{Ret}$=13.0.

The starting material is prepared as follows:

Step 58.1: 6-(6-Amino-pyrimidin-4-ylsulfanyl)-naphthalene-1-carboxylic acid

A mixture of 1.00 g (7.72 mMol) 4-amino-6-chloro-pyrimidine, 1.74 g (8.5 mMol) 6-mercapto-naphthalene-1-carboxylic acid, 10.8 g $K_3PO_4$ and 35 mg (0.23 mMol) NaI in 50 ml NMP is stirred for 2.5 h at 110° C. Then the mixture is poured into 230 ml of a 5% solution of citric acid in water, the crude product filtered off and washed with water. Stirring in boiling isopropanol and filtration gives the title compound: m.p.: 264-266° C.; MS: [M+1]$^+$=298.

Example 59

6-(6-Amino-pyrimidine-4-sulfinyl)-naphthalene-1-carboxylic acid (3-trifluoromethyl-phenyl)-amide To a suspension of 100 mg (0.227 mMol) 6-(6-amino-pyrimidin-4-ylsulfanyl)-naphthalene-1-carboxylic acid (3-trifluoromethyl-phenyl)-amide in 3 ml $CH_3COOH$/$H_2O$ 1:1, 0.1 ml of a 35% solution of $H_2O_2$ are added. After 16 h at rt, another 80 µl of $H_2O_2$ are added and stirring is continued for 4 h at 60° C. Cooling to rt, filtration, washing and drying (HV, 100° C.) gives the title compound: MS: [M+1]$^+$=457; HPLC: $^At_{Ret}$=13.3; IR: 1042 cm$^{-1}$ (S=O).

Example 60

6-(6-Amino-pyrimidine-4-sulfonyl)-naphthalene-1-carboxylic acid (3-trifluoromethyl-phenyl)-amide To a solution of 110 mg (0.25 mMol) 6-(6-amino-pyrimidin-4-ylsulfanyl)-naphthalene-1-carboxylic acid (3-trifluoromethyl-phenyl)-amide in 5 ml $CH_3COOH$, a solution of 0.20 g (1.26 mMol) $KMnO_4$ in 7.5 ml $H_2O$ is added dropwise during 30 min. The mixture is poured into 200 ml of a 2.5% solution of $Na_2SO_3$ in water. The precipitated solid is filtered off, washed with water and dried. Chromatography (Combi Flash; EtOAc/$CH_2Cl_2$ 3:7→7:3) and crystallization from ether gives the title compound: m.p.: 229-231° C.; MS: [M+1]$^+$=473; IR:. 1156/1125 cm$^{-1}$ (O=S=O).

Example 61

6-(6-Amino-pyrimidin-4-ylsulfanyl)-naphthalene-1-carboxylic acid (3-trifluoromethoxy-phenyl)-amide To 95 mg (0.32 mMol) 6-(amino-pyrimidin-4-ylsulfanyl)-naphthalene-1-carboxylic acid, 85 mg (0.48 mMol) 3-trifluoromethoxy-aniline, 446 µl (3.2 mMol) $Et_3N$ and 4 mg (0.03 mMol) DMAP in 3 ml DMF, 0.37 ml (0.63 mMol) propylphosphonic anhydride are added. After 3 h at rt, the reaction mixture is worked up as described for Ex. 58, yielding the title compound: m.p.: 197-199° C.; MS: [M+1]$^+$=457.

Example 62

6-(Pyridin-4-yl-methyl)-naphthalene-1-carboxylic acid (4-fluoro-3-trifluoromethyl-phenyl)-amide A mixture of 22.4 mg (0.10 mMol) Pd($O_2CCH_3$)$_2$, 52.6 mg (0.20 mMol) triphenylphosphine, 151 mg (0.33 mMol) 6-(4,4,5,5-tetramethyl-[1,3,2]dioxaborolan-2-yl)-naphthalene-1-carboxylic acid (4-fluoro-3-trifluoromethyl-phenyl)-amide and 229.3 mg (1.08 mMol) $K_3PO_4$ in 3 ml toluene is degassed repeatedly by evaporation and flushing with $N_2$. Then 59 mg (0.36 mMol) 4-chloromethyl-pyridine hydrochloride are added and the mixture is stirred at 80° C. for 20 h, when additional 18.5 mg (0.082 mMol) Pd($O_2CCH_3$)$_2$ and 43.1 mg (0.164 mMol) triphenylphosphine are added. After 3 h at 110° C. the reaction mixture is poured into water and EtOAc. The aqueous phase is separated off and extracted twice with EtOAc. The organic layers are washed with water and brine, dried (Na$_2$SO$_4$) and concentrated. Chromatography [Combi Flash; CH$_2$Cl$_2$→CH$_2$Cl$_2$/(MeOH+10% NH$_3^{aq}$) 9:1] gives the title compound: MS: [M+1]$^+$=425; HPLC: $^A$t$_{Ret}$=12.7.

The starting material is prepared as follows:

Step 62.1: Trifluoro-methanesulfonic acid 5-(4-fluoro-3-trifluoromethyl-phenylcarbamoyl)-naphthalen-2-yl ester 0.94 g (5.0 mMol) 6-hydroxy-naphthalene-1-carboxylic acid in a mixture of 50 ml CH$_2$Cl$_2$, 25 ml dioxane and 2.4 ml (30 mMol) pyridine is cooled to −78° C. Then a solution of 1.98 ml (12 mMol) trifluoro-methanesulfonic acid anhydride in 5 ml CH$_2$Cl$_2$ is added dropwise and the mixture is warmed up to rt. After 5 h, 1.43 g (8.0 mMol) 4-fluoro-3-trifluoro-aniline dissolved in 5 ml CH$_2$Cl$_2$ are added and stirring is continued over night. A formed precipitate is filtered off and discarded and the filtrate diluted with EtOAc and sat. NaHCO$_3$/H$_2$O 1:1. The aqueous phase is separated and extracted twice with EtOAc. The organic layers are washed with water and brine, dried (Na$_2$SO$_4$) and concentrated. Column chromatography (SiO$_2$; toluene/EtOAc 199:1→9:1) and partial concentration leads to the crystalline title compound: m.p.: 171-172° C.; MS: [M−1]=480.

Step 62.2: 6-(4,4,5,5-Tetramethyl-[1,3,2]dioxaborolan-2-yl)-naphthalene-1-carboxylic acid (4-fluoro-3-trifluoromethyl-phenyl)-amide A mixture of 1.203 g (2.5 mMol) trifluoro-methanesulfonic acid 5-(4-fluoro-3-trifluoromethyl-phenylcarbamoyl)-naphthalen-2-yl ester, 762 mg (3.0 mMol) 4,4',5,5,4',4'',5',5'-octamethyl-[2,2']bi[[1,3,2]dioxaborolanyl] and 736 mg (7.5 mMol) potassium acetate in 12 ml DMF is degassed repeatedly by evaporation and flushing with N$_2$. Then 100 mg (0.12 mMol) of the dichloromethane complex of [1,1'-bis(diphenylphosphino)ferrocene]dichloropalladium(II) are added and the mixture is stirred for 3 h at 80° C. The mixture is diluted with EtOAc and H$_2$O, the aqueous phase separated off and extracted twice with EtOAc. The organic layers are washed twice with water and brine, dried (Na$_2$SO$_4$) and concentrated. Chromatography (Combi Flash: CH$_2$Cl$_2$/hexane 1:1; crude product added as solution in CH$_2$Cl$_2$ onto preconditioned column and rapidly eluated with CH$_2$Cl$_2$/hexane 1:1→CH$_2$Cl$_2$) gives the title compound: MS: [M+1]$^+$=460; TLC(CH$_2$Cl$_2$): R$_f$=0.30; HPLC: $^A$t$_{Ret}$=18.3.

Example 63

6-(2-Methyl-pyridin-4-yloxy)-naphthalene-1-carboxylic acid (3-trifluoromethyl-phenyl)-amide To a solution of 331 mg (1.0 mMol) 6-hydroxy-naphthalene-1-carboxylic acid (3-trifluoromethyl-phenyl)-amide in 0.375 ml DMF and 1.37 ml DMPU (dimethyl-propylene urea) is added 180 mg (1.1 mMol) 4-chloro-2-methyl-pyridine followed by 336 mg (3 mMol) potassium t-butoxide. The dark viscous mixture is stirred 3 days at 100° C. After cooling to rt the mixture is diluted with EtOAc, washed with brine, dried over sodium sulfate and evaporated. The remaining DMPU and DMF is distilled off in a Kugelrohr apparatus (100° C., under vacuum). The residue is purified by flash-chromatography on a silica gel column and eluting with EtOAc. Concentration of the pure samples leads to crystalline title compound: MS: [M+1]$^+$=423; TLC(EtOAc): R$_f$=0.5; HPLC: $^E$t$_{Ret}$=3.42.

The starting material is prepared as follows:

Step 63.1: 6-hydroxy-naphthalene-1-carboxylic acid (3-trifluoromethyl-phenyl)-amide To an ice-cooled solution of 17.2 g (65 mMol) 6-hydroxy-naphthalene-1-carboxylic acid and 9.9 g (65 mMol) HOBT in 260 ml of THF is added dropwise a solution of 14.4 g (70.2 mMol) DCC in 45 ml of THF over 20 minutes. The reaction mixture is stirred 15 minutes at 0° C. and then 1 hour at rt. The solid formed is removed by filtration and washed with a small amount of cold THF. The filtrate is evaporated and the residue triturated with EtOAc/hexanes 4:6. The crystalline activated ester was filtered off and dried. 9.15 g of this active ester (30 mMol) are dissolved in 80 ml of THF and treated with 3.5 ml (30 mMol) 3-trifluoromethyl-anilin. After refluxing for 24 h another 0.35 ml (3 mMol) 3-trifluoromethyl-anilin are added and the mixture is refluxed for another 24 h. The solvent is removed and the residue subjected to a flash-chromatography on silica gel using EtOAc/hexanes 4:6. Pure fractions are evaporated and the residue is triturated with petrol ether. The crystalline title compound is filtered and dried: MS: [M+1]$^+$=332; TLC(EtOAc/hexanes 4:6): R$_f$=0.53; HPLC: $^E$t$_{Ret}$=3.8.

Example 64

4-[5-(3-Trifluoromethyl-phenylcarbamoyl)-naphthalen-2-yloxy]-pyridine-2-carboxylic acid butyl ester A mixture of 993 mg (3.0 mMol) 6-hydroxy-naphthalene-1-carboxylic acid (3-trifluoromethyl-phenyl)-amide, 10 ml n-butanol, 1.286 g (7.5 mMol) 4-chloro-pyridine-2-carboxylic acid methyl ester, 0.5 ml (3.6 mMol) triethylamin and 10 mg 4-dimethylamino-pyridine is heated under reflux for 5 days. After cooling the mixture is evaporated, diluted with EtOAc and washed with diluted hydrochloric acid. The EtOAc phase is dried with sodium sulfate, concentrated and the residue is purified by flash-chromatography on a silica gel column eluting with EtOAc/hexanes 4:6. Evaporation of the pure samples leads to crystalline title compound: m.p.: 128-130° C.; MS: [M+1]$^+$=509; TLC(EtOAc): R$_f$=0.27; HPLC: $^E$t$_{Ret}$=4.57.

Example 65

4-[5-(3-Trifluoromethyl-phenylcarbamoyl)-naphthalen-2-yloxy]-pyridine-2-carboxylic acid methylamide 101 mg (0.2 mMol) 4-[5-(3-Trifluoromethyl-phenylcarbamoyl)-naphthalen-2-yloxy]-pyridine-2-carboxylic acid butyl ester and 1.0 ml of a 33% methylamine solution in ethanol are heated for 1 h under reflux. The mixture is cooled, concentrated and the residue is purified by flash-chromatography on a silica gel column eluting with EtOAc/hexanes 6:4. Evaporation of the pure samples leads to crystalline title compound: m.p.: 175-177° C.; MS: [M+1]$^+$=466; HPLC: $^E$t$_{Ret}$=4.18.

Using the same procedure as for the previous example the following compounds were synthesized:

Example 66

4-[5-(3-Trifluoromethyl-phenylcarbamoyl)-naphthalen-2-yloxy]-pyridine-2-carboxylic acid amide The title compound is obtained as a solid: m.p.: 117-120° C.; MS: [M+1]$^+$=452; TLC(EtOAc/hexanes 6:4): R$_f$=0.3; HPLC: $^E$t$_{Ret}$=3.91.

Example 67

4-[5-(3-Trifluoromethyl-phenylcarbamoyl)-naphthalen-2-yloxy]-pyridine-2-carboxylic acid (2-dimethylamino-ethyl)-amide The title compound is obtained as a solid: m.p.: 80-82° C.; MS: [M+1]$^+$=523; TLC (dichloromethane/ethanol 9:1 and 1% conc. ammonia): R$_f$=0.3; HPLC: $^E$t$_{Ret}$=3.46.

Example 68

6-(2-Amino-pyridin-4-yloxy)-naphthalene-1-carboxylic acid (3-trifluoromethyl-phenyl)-amide To a solution of 60 mg (0.11 mMol) {4-[5-(3-trifluoromethyl-phenylcarbamoyl)-naphthalen-2-yloxy]-pyridin-2-yl}-carbamic acid tert-butyl ester in 1 ml dioxane, 30 μl (0.12 mMol) of a 4 N hydrochloric acid solution in dioxane are added and the resulting solution is heated under reflux for 8 h. The dioxane is evaporated and the residue partitioned between EtOAc and saturated sodium bicarbonate solution. The aqueous phase was extracted twice with EtOAc. The combined EtOAc phases are washed with brine, dried with sodium sulfate and evaporated. The residue is purified by flash-chromatography on a silica gel column eluting with dichloromethane/ethanol 95:5 containing 1% conc. ammonia. Evaporation of the pure samples leads to crystalline title compound: m.p.: 222-224° C.; MS: $[M+1]^+=424$; TLC (dichloromethane/ethanol 95:5 and 1% conc. ammonia): $R_f=0.3$; HPLC: $^Et_{Ret}=3.46$.

The starting material is prepared as follows:

Step 68.1: 4-[5-(3-Trifluoromethyl-phenylcarbamoyl)-naphthalen-2-yloxy]-pyridine-2-carboxylic acid 165 mg (0.32 mMol) 4-[5-(3-Trifluoromethyl-phenylcarbamoyl)-naphthalen-2-yloxy]-pyridine-2-carboxylic acid butyl ester are dissolved in 6 ml of ethanol and treated with 0.34 ml 1 N sodium hydroxide solution. The suspension is heated for 2 h under reflux, cooled and the solvent evaporated. The residue is triturated with EtOAc and filtered. The solid is taken up in a small amount of water and acidified with 2 N hydrochloric acid (pH ~5). Extraction with EtOAc followed by drying of the EtOAc extracts with sodium sulfate and evaporation of the solvent gives pure title compound: MS: $[M+1]^+=453$; TLC (EtOAc/hexanes 4:6): $R_f=0.35$; HPLC: $^Et_{Ret}=3.29$.

Step 68.2: {4-[5-(3-Trifluoromethyl-phenylcarbamoyl)-naphthalen-2-yloxy]-pyridin-2-yl}-carbamic acid tert-butyl ester A mixture of 113 mg (0.25 mMol) 4-[5-(3-trifluoromethyl-phenylcarbamoyl)-naphthalen-2-yloxy]-pyridine-2-carboxylic acid, 1.5 ml tert-butanol, 0.07 ml (0.3 mMol) phosphorazidic acid diphenyl ester and 0.04 ml (0.03 mMol) triethylamine is heated under reflux for 4 h. The solvent is evaporated, the residue taken up in EtOAc and washed with saturated sodium bicarbonate solution and brine, dried with sodium sulfate and concentrated again. The residue is purified by flash-chromatography on a silica gel column eluting with EtOAc/hexanes 4:6. Evaporation of the pure samples leads to the title compound: MS: $[M+1]^+=524$; TLC (EtOAc/hexanes 4:6): $R_f=0.35$; HPLC: $^Et_{Ret}=4.07$.

Example 69

{4-[5-(3-Trifluoromethyl-phenylcarbamoyl)-naphthalen-2-yloxy]-pyridin-2-yl}-carbamic acid methyl ester To a mixture of 42 mg (0.1 mMol) 6-(2-amino-pyridin-4-yloxy)-naphthalene-1-carboxylic acid (3-trifluoromethyl-phenyl)-amide and 16 μl (0.12 mMol) triethylamine in 1 ml of THF are added 10 μl (0.12 mMol) of methyl chloroformate at rt. After stirring for 1 h at rt the mixture is diluted with EtOAc. This is then washed with saturated sodium bicarbonate solution and brine, dried with sodium sulfate and evaporated. The residue is purified by flash-chromatography on a silica gel column eluting with EtOAc/hexanes 1:1. After a second chromatography of the enriched fractions, the pure title compound is obtained as a solid: m.p.: 230-232° C.; MS: $[M+1]^+=482$; TLC (EtOAc/hexanes 1:1): $R_f=0.45$; HPLC: $^Et_{Ret}=3.69$.

Example 70

6-[2-(2-Amino-pyrimidin-4-yl)-ethyl]-naphthalene-1-carboxylic acid (3-trifluoromethyl-phenyl)-amide 0.069 g (0.148 mMol) 6-(2-Amino-6-chloro-pyrimidin-4-ylethynyl)-naphthalene-1-carboxylic acid (3-trifluoromethyl-phenyl)-amide is hydrogenated in the presence of 12 mg of magnesium oxide and 20 mg 10% palladium on carbon in 5 ml of THF at rt. After 48 h the catalyst was filtered off and the filtrate evaporated. The residue is chromatographed on a 4 g silica gel column on a Combi-Flash Companion™ (Isco Inc.) apparatus using a gradient of 20%→100% EtOAc in hexanes as solvent. The title compound is obtained as a colorless solid: m.p.: 225-227° C.; MS: $[M+1]^+=435$; TLC (EtOAc): $R_f=0.25$; HPLC: $^Et_{Ret}=3.43$.

The starting material is prepared as follows:

Step 70.1: Trifluoro-methanesulfonic acid 5-(3-trifluoromethyl-phenylcarbamoyl)-naphthalen-2-yl ester 1.324 g (4.0 mMol) 6-hydroxy-naphthalene-1-carboxylic acid (3-trifluoromethyl-phenyl)-amide are dissolved in 7.2 ml of pyridine and the solution is cooled to −10 to −15° C. 0.824 ml (5 mMol) Trifluorosulfonic acid anhydride are added dropwise at that temperature over 10 minutes. The mixture is then stirred at 0° C. for 10 minutes and then 2 h at rt. The reaction mixture is poured onto 25 ml of ice-water, stirred efficiently for a few minutes and then extracted with tert.-butyl-methylether. The organic phases are combined and washed with 1 N HCl and brine, dried with sodium sulfate and concentrated to about 15 to 20 ml. The suspension formed is cooled to 5° C. to complete he crystallization. The title compound is collected by filtration and dried: m.p.: 177-178° C.; MS: $[M+1]^+=464$; TLC (EtOAc/hexanes 3:7): $R_f=0.34$; HPLC: $^Et_{Ret}=4.90$.

Step 70.2: 6-Trimethylsilanylethynyl-naphthalene-1-carboxylic acid (3-trifluoromethyl-phenyl)-amide 0.695 g (1.5 mMol) Trifluoro-methanesulfonic acid 5-(3-trifluoromethyl-phenylcarbamoyl)-naphthalen-2-yl ester, 0.015 g (0.079 mMol) copper (I) iodide and 17.4 mg (0.0248 mMol) bis-(triphenylphosphine)-palladium dichloride are mixed in a Schlenk apparatus under nitrogen and treated at rt with a carefully degassed solution of 0.233 ml (1.65 mMol) ethinyl-trimethylsilane and 0.225 ml (1.62 mMol) triethylamine in 5.6 ml dry DMF. The clear dark solution is kept at rt for 16 h and then the DMF is evaporated under reduced pressure. The residue is chromatographed on a 40 g silica gel column on a Combi-Flash Companion™ (Isco Inc.) apparatus using a gradient of 0% →20% EtOAc in hexanes as solvent. The title compound is obtained as a tan solid: m.p.: 134-136° C.; MS: $[M+1]^+=412$; TLC (EtOAc/hexanes 1:4): $R_f=0.28$; HPLC: $^Et_{Ret}=5.40$.

Step 70.3: 6-Ethynyl-naphthalene-1-carboxylic acid (3-trifluoromethyl-phenyl)-amide 0.194 g (0.47 mMol) 6-Trimethylsilanylethynyl-naphthalene-1-carboxylic acid (3-trifluoromethyl-phenyl)-amide is dissolved in 3.8 ml of methanol at rt. After the addition of 0.1 g (0.724 mMol) potassium carbonate the mixture is stirred for 16 at rt. The solvent was removed and the residue partitioned between 10 ml of EtOAc and 5 ml of water. The organic phase is washed with brine, dried with sodium sulfate and evaporated. The title compound is obtained as a brown resin: MS: [M+1]$^+$=340; HPLC: $^E$t$_{Ret}$=4.58.

Step 70.4: 6-(2-Amino-6-chloro-pyrimidin-4-ylethynyl)-naphthalene-1-carboxylic acid (3-trifluoromethyl-phenyl)-amide Nitrogen is passed through a solution of 130 mg (0.383 mMol) 6-ethynyl-naphthalene-1-carboxylic acid (3-trifluoromethyl-phenyl)-amide and 57 mg (0.348 mMol) 2-amino-4,6-dichloro-pyrimidine in 1.3 ml DMF. After 10 to 15 minutes, 3.5 mg (0.0184 mMol) copper (I) iodide, 17.4 mg (0.0248 mMol) bis-(triphenylphosphine)-palladium dichloride and 52.2 µl (0.375 mMol) triethylamine are added and the mixture is stirred at rt and under a nitrogen atmosphere for 16 h. The DMF is removed under reduced pressure and the residue is chromatographed on a 12 g silica gel column on a Combi-Flash Companion™ (Isco Inc.) apparatus using a gradient of 0%→50% EtOAc in hexanes as solvent. The title compound is obtained as a colorless solid: m.p.: 171-175° C.; MS: [M+1]$^+$=465,467; TLC (EtOAc/hexanes 1:1): R$_f$=0.31; HPLC: $^E$t$_{Ret}$=4.74.

Example 71

6-(6-Amino-pyrimidin-4-ylethynyl)-naphthalene-1-carboxylic acid (3-trifluoromethyl-phenyl)-amide In a three-necked flask equipped with a reflux condenser, nitrogen inlet and magnetic stirrer are placed 12.8 ml of dimethoxy-ethane and 2.2 ml of water. Nitrogen is bubbled through the solution for 5 minutes and then 33.3 mg (0.184 mMol) palladium chloride, 51.1 mg (0.263 mMol) copper (I) iodide and 191 mg (0.693 mMol) triphenylphosphine are added and the mixture is heated to 40° C. Next, 0.412 g (1 mMol) 6-trimethylsilanylethynyl-naphthalene-1-carboxylic acid (3-trifluoromethyl-phenyl)-amide, 165 mg (1.25 mMol) 4-amino-6-chloropyrimidine and 629 mg (4.5 mMol) potassium carbonate are added and the mixture stirred at 75° C. for 15 h. After cooling the organic layer is separated and treated with 2.5 g of silica gel. The solvent is removed and the crude product coated on silica gel chromatographed on a 40 g silica gel column on a Combi-Flash Companion™ (Isco Inc.) apparatus using a gradient of 30%→100% EtOAc in hexanes as solvent. The title compound is obtained as a tan solid: m.p.: 217-220° C.; MS: [M+1]$^+$=433; TLC (EtOAc/hexanes 1:4): R$_f$=0.19; HPLC: $^E$t$_{Ret}$=3.36.

Example 71A

6-[(Z)-2-(6-Amino-pyrimidin-4-yl)-vinyl]-naphthalene-1-carboxylic acid (3-trifluoromethyl-phenyl)-amide 50 mg (0.116 mMol) 6-(6-Amino-pyrimidin-4-ylethynyl)-naphthalene-1-carboxylic acid (3-trifluoromethyl-phenyl)-amide are hydrogenated in 1 ml DMF containing 9.45 µl (0.14 mMol) ethylenediamine using 10 mg Lindlar catalyst and under normal pressure. After 72 h at r.t. the catalyst is removed and the solvent evaporated. The residue is chromatographed on a 4 g silica gel column on a Combi-Flash Companion™ (Isco Inc.) apparatus using a gradient of 60%→100% EtOAc in hexanes as solvent. The title compound is obtained as a colorless resin: MS: [M+1]$^+$=435; HPLC: $^F$t$_{Ret}$=3.23.

Example 71B

6-[(E)-2-(6-Amino-pyrimidin-4-yl)-vinyl]-naphthalene-1-carboxylic acid (3-trifluoromethyl-phenyl)-amide Preparation of the CrSO$_4$ solution: Under a nitrogen atmosphere 5 g (12.7 mMol) chromium(III)sulfate hydrate are dissolved in 32 ml of water and treated with 1.3 g of Zink powder. The mixture is stirred over night at r.t. and yields a blue-green solution. 21.6 mg (0.05 mMol) 6-(6-Amino-pyrimidin-4-ylethynyl)-naphthalene-1-carboxylic acid (3-trifluoromethyl-phenyl)-amide are dissolved in 2 ml of DMF and treated under nitrogen with 180 µl of the previously described solution of CrSO$_4$. The mixture is stirred at r.t. for 40 h and then treated with 0.5 ml of a 2 N sodium carbonate solution. The resulting suspension is filtered and the filtrate evaporated. The crude product is coated on silica gel and chromatographed on a 4 g silica gel column on a Combi-Flash Companion™ (Isco Inc.) apparatus using a gradient of 30%→100% EtOAc in hexanes as solvent. The title compound is obtained as a colorless material containing about 20% of the Z-isomer: MS: [M+1]$^+$=435; TLC (EtOAc): R$_f$=0.17; HPLC: $^E$t$_{Ret}$=3.34.

Example 72

6-(6-Amino-pyrimidin-4-yloxy)-1H-indole-3-carboxylic acid (3-trifluoromethyl-phenyl)-amide (Method A)

In a sealed tube, a solution of 50 mg (0.19 mMol) 6-(6-amino-pyrimidin-4-yloxy)-1H-indole-3-carboxylic acid, 69.1 µl (0.56 mMol) 3-aminobenzotrifluoride and 128.9 µl (0.93 mMol) Et$_3$N in 1 ml DMF was treated with 131 µl (0.22 mMol) of propylphosphonic anhydride (ca. 50% in DMF) and stirred at rt overnight. The reaction mixture was directly purified by reversed phase prep-HPLC (Waters system) to give the title compound as its TFA salt: MS: [M+1]$^+$=414; HPLC: $^F$t$_{Ret}$=1.78.

The starting material is prepared as follows:

Step 72.1: 6-Hydroxy-1H-indole-3-carboxylic acid methyl ester

In a sealed flask, a mixture of 10.0 g (35.6 mMol) 6-benzyloxy-1H-indole-3-carboxylic acid methyl ester (synthesized according to a literature procedure: M. Fedouloff and al. *Bioorg. Med. Chem.* 9, 2001, 2119-2128), 2.26 g (35.6 mMol) ammonium formate and 3.78 g Pd/C 10% in 200 ml EtOH was stirred at rt for 1 h. The catalyst was filtered and washed with hot MeOH. The filtrate was evaporated to give the title compound: MS: [M+1]$^+$=192; HPLC: $^F$t$_{Ret}$=1.13.

Step 72.2: 6-(6-Chloro-pyrimidin-4-yloxy)-1H-indole-3-carboxylic acid methyl ester To a solution of 6.2 g (32.4 mMol) 6-hydroxy-1H-indole-3-carboxylic acid methyl ester in 50 ml acetone, 35.7 ml (35.7 mMol) 1 N NaOH and 4.8 g (32.4 mMol) 4,6-dichloropyrimidine were added. The reaction mixture was stirred at rt for 1 h during which time the product precipitate. The reaction mixture was filtered and the solid washed with cold acetone/ water 1:1 then Et$_2$O to give the title compound which was used without further purification: MS: [M+1]$^+$=304; HPLC: $^F$t$_{Ret}$=1.94.

Step 72.3: 6-(6-Azido-pyrimidin-4-yloxy)-1H-indole-3-carboxylic acid methyl ester A mixture of 7.0 g (23.0 mMol) 6-(6-chloro-pyrimidin-4-yloxy)-1H-indole-3-carboxylic acid methyl ester and 3.0 g (46.1 mMol) NaN$_3$ in 75 ml DMF was stirred at 60° C. for 2.5 h. The reaction mixture was diluted in EtOAc then washed with water and brine. The organic layer was dried over Na$_2$SO$_4$, filtered, and evaporated. Combi-Flash Companion™ (Isco Inc.) column chromatography (SiO$_2$; gradient elution, hexane/EtOAc 8:2→4:6) yielded the title compound: MS: [M+1]$^+$=311; HPLC: $^F$t$_{Ret}$=2.07.

Step 72.4: 6-(6-Amino-pyrimidin-4-yloxy)-1H-indole-3-carboxylic acid methyl ester In a sealed flask, a suspension of 3.4 g (11.0 mMol) 6-(6-azido-pyrimidin-4-yloxy)-1H-indole-3-carboxylic acid methyl ester, 1.4 g (22.1 mMol) ammonium formate and 1.2 g Pd/C 10% in 65 ml EtOH was stirred at rt for 1 h. The catalyst was filtered through a Celite pad and washed with MeOH. The filtrate was evaporated to give the title compound which was used without further purification: MS: [M+1]$^+$=285; HPLC: $^F$t$_{Ret}$=1.08.

Step 72.5: 6-(6-Amino-pyrimidin-4-yloxy)-1H-indole-3-carboxylic acid

A suspension of 3.38 g (11.9 mMol) 6-(6-amino-pyrimidin-4-yloxy)-1H-indole-3-carboxylic acid methyl ester and 5.04 g (118.9 mMol) LiOH.H$_2$O in 136 ml MeOH/H$_2$O 5:3 was stirred at 80° C. for 4 h. The clear solution was cooled to rt, acidified by the addition of 6.7 ml (178.0 mMol) formic acid, and concentrated under reduced pressure. The residue was diluted in water and the formed solid was filtered and washed with water to yield the title compound: MS: [M+1]$^+$=271; HPLC: $^F$t$_{Ret}$=0.69.

Example 73

6-(6-Amino-pyrimidin-4-yloxy)-1H-indole-3-carboxylic acid (3-methoxy-phenyl)-amide (Method B)

A solution of 50 mg (0.19 mMol) 6-(6-amino-pyrimidin-4-yloxy)-1H-indole-3-carboxylic acid, 68.0 mg (0.56 mMol) 3-methoxyphenylamine, 102.0 μl (0.93 mMol) NMM and 106 mg (0.22 mMol) HATU in 1 ml DMF was stirred at rt overnight. The reaction mixture was directly purified by reversed phase prep-HPLC (Waters system) to give the title compound as its TFA salt: MS: [M+1]$^+$=376; HPLC: $^F$t$_{Ret}$=1.40.

Example 74

6-(6-Amino-pyrimidin-4-yloxy)-1H-indole-3-carboxylic acid (4-fluoro-3-trifluoro-methyl-phenyl)-amide (Method C)

A suspension of 50 mg (0.19 mMol) 6-(6-amino-pyrimidin-4-yloxy)-1H-indole-3-carboxylic acid in 2 ml dioxane was treated with 134.6 μl (1.85 mMol) SOCl$_2$ and stirred under reflux for 2 h. The reaction mixture was evaporated under reduced pressure leading to the crude acid chloride. To a solution of the crude acid chloride in 2 ml NMP, 35.6 μl (0.278 mMol) 4-fluoro-3-(trifluoromethyl)aniline and 306 μl (2.78 mMol) NMM were added. The reaction mixture was stirred at rt for 2 h then directly purified reversed phase prep-HPLC (Waters system). After lyophilization, the title compound was obtained as its TFA salt: MS: [M+1]$^+$=432; HPLC: $^G$t$_{Ret}$=2.83.

Example 75

The following compounds can be obtained analogously to Ex. 72, Ex. 73 or Ex. 74.

| | R | Methode | HPLC $^F$t$_{Ret}$ [min] | MS [M + 1]$^+$ |
|---|---|---|---|---|
| a) | 3-chlorophenyl-NH-* | A | 1.61 | 380 |
| b) | 4-trifluoromethylphenyl-NH-* | A | 1.76 | 414 |
| c) | 4-chlorophenyl-NH-* | A | 1.58 | 380 |
| d) | 1-phenyl-3-tert-butyl-pyrazol-5-yl-NH-* | A | 1.71 | 468 |
| e) | 4-fluorophenyl-NH-* | B | 1.40 | 364 |

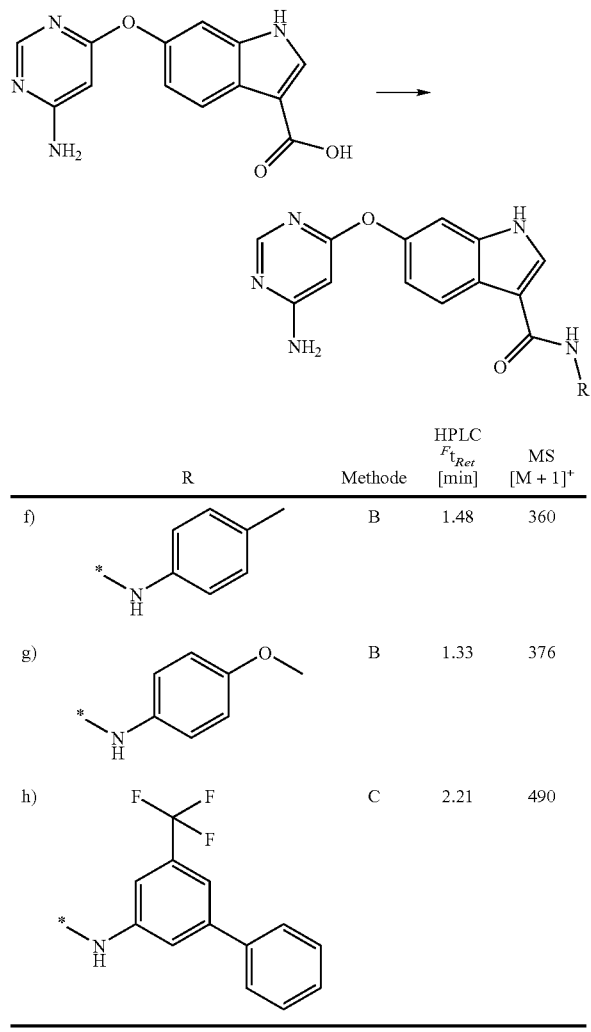

| R | Methode | HPLC $^F t_{Ret}$ [min] | MS [M + 1]$^+$ |
|---|---|---|---|
| f) ![structure] | B | 1.48 | 360 |
| g) ![structure] | B | 1.33 | 376 |
| h) ![structure] | C | 2.21 | 490 |

Example 76

6-(6-Amino-pyrimidin-4-yloxy)-1-methyl-1H-indole-3-carboxylic acid (3-trifluoro-methyl-phenyl)-amide In a sealed flask, a solution of 16 mg (0.038 mMol) 6-(6-chloro-pyrimidin-4-yloxy)-1-methyl-1H-indole-3-carboxylic acid (3-trifluoromethyl-phenyl)-amide in 1 ml NMP and 1 ml NH$_4$OH 25% was stirred at 120° C. for 2 h. The reaction mixture was concentrated under reduced pressure and the residue purified by prep-HPLC to give the title compound as its TFA salt: MS: [M+1]$^+$=428; HPLC: $^F t_{Ret}$=1.87.

The starting material is prepared as follows:

Step 76.1:
6-Benzyloxy-1-methyl-1H-indole-3-carboxylic acid methyl ester

To a solution of 2.33 g (8.28 mMol) 6-benzyloxy-1H-indole-3-carboxylic acid methyl ester in 20 ml DMF, 4.05 g (12.42 mMol) Cs$_2$CO$_3$ and 1.03 ml (16.57 mMol) MeI were added and the mixture was stirred at 60° C. for 3 h. The reaction middle was diluted in EtOAc and water, and the aqueous phase was extracted with EtOAc (3 times). The combined organic fractions were washed with brine, then dried over Na$_2$SO$_4$, filtered, and evaporated. Purification via silica gel Combiflash chromatography (gradient elution, hexane/tert-butyl-methylether 8:2 to 4:6) led to the title compound as a brownish solid: MS: [M+1]$^+$=296; HPLC: $^F t_{Ret}$=2.58; TLC (tert-butyl-methylether/hexane 1:1): R$_f$=0.34.

Step 76.2:
6-Benzyloxy-1-methyl-1H-indole-3-carboxylic acid

A suspension of 2.06 g (6.98 mMol) 6-benzyloxy-1-methyl-1H-indole-3-carboxylic acid methyl ester and 2.63 g (62.78 mMol) LiOH-H$_2$O in 75 ml MeOH/H$_2$O 2:1 was stirred at 60° C. overnight. The clear solution was cooled to rt and concentrated. The residue was diluted in water and acidified by the addition of 2 M HCl. The formed white precipitate was collected by filtration, washed with water and dried at 40° C. under high vacuum to give the title compound as an off-white solid: MS: [M+1]$^+$=282; HPLC: $^F t_{Ret}$=2.12.

Step 76.3:
6-Hydroxy-1-methyl-1H-indole-3-carboxylic acid

In a sealed flask, a suspension of 1.57 g (5.58 mMol) 6-benzyloxy-1-methyl-1H-indole-3-carboxylic acid, 528 mg (8.37 mMol) ammonium formate and 594 mg Pd/C 10% in 25 ml EtOH was stirred at rt for 2 h. The catalyst was filtered and washed with hot MeOH. The filtrate was evaporated to give the title compound as an off-white solid: MS: [M+i]$^+$=192; HPLC: $^F t_{Ret}$=0.85.

Step 76.4: 6-(6-Chloro-pyrimidin-4-yloxy)-1-methyl-1H-indole-3-carboxylic acid To a solution of 800 mg (4.18 mMol) 6-hydroxy-1-methyl-1H-indole-3-carboxylic acid in 20 ml acetone, 10 ml (10 mMol) 1 N NaOH and 935 mg (6.28 mMol) 4,6-dichloropyrimidine were added. The reaction mixture was stirred at rt for 2 h, then concentrated under reduced pressure. The residue was diluted in water and extracted with CH$_2$Cl$_2$ (2 times). The aqueous phase was acidified by the addition of 2 N HCl (→pH 3-4) and the resulting slurry was extracted with EtOAc (3 times). The combined organic fractions were dried over Na$_2$SO$_4$, filtered and evaporated to yield the title compound as a brown solid which was used in the next step without further purification: MS: [M+1]$^+$=304; HPLC: $^F t_{Ret}$=1.68.

Step 76.5: 6-(6-Chloro-pyrimidin-4-yloxy)-1-methyl-1H-indole-3-carboxylic acid (3-trifluoro-methyl-phenyl)-amide A suspension of 60 mg (0.20 mMol) 6-(6-chloro-pyrimidin-4-yloxy)-1-methyl-1H-indole-3-carboxylic acid in 2 ml dioxane was treated with 143.8 µl (1.98 mMol) SOCl$_2$ and stirred under reflux for 2 h. The reaction mixture was evaporated under reduced pressure leading to the crude acid chloride. To the crude acid chloride in 2 ml NMP, 36.9 µl (0.30 mMol) 3-(trifluoromethyl)aniline and 326.5 µl (2.96 mMol) NMM were added. The reaction mixture was stirred at rt for 2 h then directly purified by injection in prep-HPLC (Waters system). After lyophilization, the title compound was obtained: MS: [M+1]$^+$=447; HPLC: $^F t_{Ret}$=2.76.

Example 77

The following compounds can be obtained analogously to Ex. 76.

| | R | HPLC $^F t_{Ret}$ [min] | MS [M + 1]$^+$ |
|---|---|---|---|
| a) | 4-fluoro-3-trifluoromethyl-phenylamino | 1.90 | 446 |
| b) | 3-trifluoromethyl-5-phenyl-phenylamino | 3.42 ($^G t_{Ret}$) | 504 |

Example 78

6-(6-Amino-pyrimidin-4-yloxy)-1-ethyl-1H-indole-3-carboxylic acid (3-trifluoro-methyl-phenyl)-amide Prepared as described in Ex. 74 from 50 mg (0.17 mMol) 6-(6-amino-pyrimidin-4-yloxy)-1-ethyl-1H-indole-3-carboxylic acid and 31.3 μl (0.25 mMol) 3-aminobenzotrifluoride: [M+1]$^+$=442; HPLC: $^F t_{Ret}$=1.93.

The starting material is prepared as follows:

Step 78.1:
6-Benzyloxy-1-ethyl-1H-indole-3-carboxylic acid methyl ester

Prepared as described in Ex. 76, Step 76.1 from 2.0 g (7.11 mMol) 6-benzyloxy-1H-indole-3-carboxylic acid methyl ester and 1.06 ml (14.22 mMol) ethyl bromide: [M+1]$^+$=310; HPLC: $^G t_{Ret}$=3.61.

Step 78.2:
6-Benzyloxy-1-ethyl-1H-indole-3-carboxylic acid

Prepared as described in Ex. 76, Step 76.2 from 1.8 g (7.76 mMol) 6-benzyloxy-1-ethyl-1H-indole-3-carboxylic acid methyl ester: [M+1]$^+$=296; HPLC: $^F t_{Ret}$=2.27.

Step 78.3:
6-Hydroxy-1-ethyl-1H-indole-3-carboxylic acid

Prepared as described in Ex. 76, Step 76.3 from 1.64 g (5.55 mMol) 6-benzyloxy-1-ethyl-1H-indole-3-carboxylic acid: [M+1]$^+$=206; HPLC: $^F t_{Ret}$=1.05.

Step 78.4: 6-(6-Chloro-pyrimidin-4-yloxy)-1-ethyl-1H-indole-3-carboxylic acid Prepared as described in Ex. 76, Step 76.4 from 1.21 g (6.33 mMol) 6-hydroxy-1-ethyl-1H-indole-3-carboxylic acid and 1.89 g (12.66 mMol) 4,6-dichloropyrimidine: [M+1]$^+$=318; HPLC: $^F t_{Ret}$=1.85.

Step 78.5: 6-(6-Azido-pyrimidin-4-yloxy)-1-ethyl-1H-indole-3-carboxylic acid A mixture of 1.5 g (4.72 mMol) 6-(6-chloro-pyrimidin-4-yloxy)-1-ethyl-1H-indole-3-carboxylic acid and 1.23 g (18.88 mMol) NaN$_3$ in 15 ml DMF was stirred at 60° C. for 2.5 h. The reaction mixture was diluted in EtOAc then washed with 2 M HCl and brine. The organic layer was dried over Na$_2$SO$_4$, filtered, and evaporated. Combi-Flash Companion™ (Isco Inc.) column chromatography (SiO$_2$; hexane with 2% AcOH/EtOAc 8:2→2:8) yielded the title compound: MS: [M+1]$^+$=325; HPLC: $^F t_{Ret}$=1.97.

Step 78.6: 6-(6-Amino-pyrimidin-4-yloxy)-1-ethyl-1H-indole-3-carboxylic acid Prepared as described in Ex. 72, Step 72.4 from 1.06 g (3.28 mMol) 6-(6-azido-pyrimidin-4-yloxy)-1-ethyl-1H-indole-3-carboxylic acid, 418.0 mg (6.56 mMol) ammonium formate and 349.2 mg Pd/C 10%: [M+1]$^+$=299; HPLC: $^F t_{Ret}$=1.00.

Example 79

6-(6-Amino-pyrimidin-4-yloxy)-1-ethyl-1H-indole-3-carboxylic acid (4-fluoro-3-trifluoromethyl-phenyl)-amide Prepared as described in Ex. 78 from 50 mg (0.17 mMol) 6-(6-amino-pyrimidin-4-yloxy)-1-ethyl-1H-indole-3-carboxylic acid and 32.3 μl (0.25 mMol) 4-fluoro-3-(trifluoromethyl)aniline: [M+1]$^+$=460; HPLC: $^F t_{Ret}$=2.00.

Example 80

6-(6-Amino-pyrimidin-4-yloxy)-1-iso-propyl-1H-indole-3-carboxylic acid (3-trifluoromethyl-phenyl)-amide Prepared as described in Ex. 76 from 18 mg (0.038 mMol) 6-(6-chloro-pyrimidin-4-yloxy)-1-iso-propyl-1H-indole-3-carboxylic acid (3-trifluoromethyl-phenyl)-amide: [M+1]$^+$=456; HPLC: $^G t_{Ret}$=3.14.

The starting material is prepared as follows:

Step 80.1:
6-Benzyloxy-1-iso-propyl-1H-indole-3-carboxylic acid methyl ester Prepared as described in Ex. 76, Step 76.1 from 1.0 g (3.56 mMol) 6-benzyloxy-1H-indole-3-carboxylic acid methyl ester and 667 μl (7.10 mMol) 2-bromopropane: [M+1]$^+$=324; HPLC: $^G t_{Ret}$=3.72.

Step 80.2:
6-Benzyloxy-1-iso-propyl-1H-indole-3-carboxylic acid

Prepared as described in Ex. 76, Step 76.2 from 1.04 g (3.22 mMol) 6-benzyloxy-1-iso-propyl-1H-indole-3-carboxylic acid methyl ester: [M+1]$^+$=310; HPLC: $^Ft_{Ret}$=2.38.

Step 80.3: 6-Benzyloxy-1-iso-propyl-1H-indole-3-carboxylic acid (3-trifluoromethyl-phenyl)-amide A suspension of 100 mg (0.32 mMol) 6-benzyloxy-1-iso-propyl-1H-indole-3-carboxylic acid in 2 ml dioxane was treated with 235.2 µl (3.23 mMol) SOCl$_2$ and stirred under reflux for 2 h. The reaction mixture was evaporated under reduced pressure leading to the crude acid chloride. To the crude acid chloride in 2 ml NMP, 60.3 µl (0.48 mMol) 3-(trifluoromethyl)aniline and 534.2 µl (4.85 mMol) NMM were added. The reaction mixture was stirred at rt for 2 h then diluted in water and extracted with tert-butyl-methylether. The organic fraction was successively washed with 2 M HCl, 2 M Na$_2$CO$_3$, and brine, then dried over Na$_2$SO$_4$, filtered and evaporated. Combi-Flash Companion™ (Isco Inc.) column chromatography (SiO$_2$; hexane/EtOAc 95:5→6:4) yielded the title compound: MS: [M+1]$^+$=453; HPLC: $^Ft_{Ret}$=3.25.

Step 80.4: 6-Hydroxy-1-iso-propyl-1H-indole-3-carboxylic acid (3-trifluoromethyl-phenyl)-amide Prepared as described in Ex. 76, Step 76.3 from 44 mg (0.097 mMol) 6-benzyloxy-1-iso-propyl-1H-indole-3-carboxylic acid (3-trifluoromethyl-phenyl)-amide: [M+1]$^+$=363; HPLC: $^Ft_{Ret}$=2.43.

Step 80.5: 6-(6-Chloro-pyrimidin-4-yloxy)-1-iso-propyl-1H-indole-3-carboxylic acid (3-trifluoromethyl-phenyl)-amide Prepared as described in Ex. 76, Step 76.4 from 34 mg (0.094 mMol) 6-hydroxy-1-iso-propyl-1H-indole-3-carboxylic acid (3-trifluoromethyl-phenyl)-amide and 14.0 mg (0.094 mMol) 4,6-dichloropyrimidine: [M+1]$^+$=475; HPLC: $^Ft_{Ret}$=3.00.

Example 81

6-(6-Acetylaminopyrimidin-4-yloxy)-naphthalene-1-carboxylic acid (4-piperazin-1-ylmethyl-3-trifluoromethylphenyl)amide 4.5 ml of 4 M solution of HCl in dioxane are added to a stirred solution of 520 mg (0.727 mMol) 4-(4-{[6-(6-acetylamino-pyrimidin-4-yloxy)-naphthalene-1-carbonyl]-amino}-2-trifluoromethyl-benzyl)-piperazine-1-carboxylic acid tert-butyl ester in 4.5 ml dioxane. After 2 hours, the mixture is neutralized with aqueous 2 M NaOH. The precipitated product is filtered, washed with water and dried. The solid is then dissolved in CH$_2$Cl$_2$/MeOH 5:1 and the CH$_2$Cl$_2$ is evaporated off under reduced pressure to afford a suspension which is filtered to give the title compound as a beige solid: m.p.: 194-197° C.

The starting material is prepared as follows:

Step 81.1: 6-(6-Chloropyrimidin-4-yloxy)-naphthalene-1-carbonyl chloride

A solution of 571 µl (6.66 mMol) oxalyl chloride in 15 ml CH$_2$Cl$_2$ is added to an ice-cooled solution of 1 g (step 25.1; 3.33 mMol) 6-(6-chloro-pyrimidin-4-yloxy)-naphthalene-1-carboxylic acid and 10 µl DMF in 30 ml CH$_2$Cl$_2$. The reaction mixture is stirred at room temperature for 1 h. The solvent is then evaporated off under reduced pressure to afford the title compound as a brown solid, which is used directly without further purification.

Step 81.2: 4-(4-{[6-(6-Chloro-pyrimidin-4-yloxy)-naphthalene-1-carbonyl]-amino}-2-trifluoromethyl-benzyl)-piperazine-1-carboxylic acid tert-butyl ester A solution of 1.15 g (2.89 mMol) 6-(6-chloropyrimidin-4-yloxy)-naphthalene-1-carbonyl chloride in 20 ml CH$_2$Cl$_2$ is added to a stirred solution of 922 mg (2.51 mMol) 4-(4-amino-2-trifluoromethyl-benzyl)-piperazine-1-carboxylic acid tert-butyl ester and 878 µl (5.03 mMol) diisopropylethylamine in 20 ml CH$_2$Cl$_2$. After 30 min, the reaction mixture is poured into a mixture of water and CH$_2$Cl$_2$. The aqueous phase is separated off and extracted with CH$_2$Cl$_2$. The combined organic layers are washed with water and brine, dried (Na$_2$SO$_4$) and concentrated. Column chromatography (SiO$_2$; CH$_2$Cl$_2$/EtOAc 1:1) gives the title compound as a brown solid.

Step 81.3: 4-(4-{[6-(6-Acetylamino-pyrimidin-4-yloxy)-naphthalene-1-carbonyl]-amino}-2-trifluoromethyl-benzyl)-piperazine-1-carboxylic acid tert-butyl ester A mixture of 637 mg (0.97 mMol) 4-(4-{[6-(6-chloro-pyrimidin-4-yloxy)-naphthalene-1-carbonyl]-amino}-2-trifluoromethyl-benzyl)-piperazine-1-carboxylic acid tert-butyl ester, 86 mg (1.46 mMol) acetamide, 34 mg (0.058 mMol) (9,9-dimethyl-9H-xanthene-4,5-diyl)bis[diphenylphosphine], 18 mg (0.019 mMol) tris(dibenzylideneacetone)dipalladium, 448 mg (1.36 mMol) cesium carbonate in 5 ml dry dioxane is heated under an argon atmosphere at 70° C. for 3 h. The cooled suspension is diluted with water, filtered (hyflo) and the residue is dissolved in EtOAc. The solvent is evaporated off under reduced pressure to afford the crude product which is used in the next step without further purification.

Example 82

6-(6-Amino-pyrimidin-4-yloxy)-naphthalene-1-carboxylic acid (4-piperazin-1-ylmethyl-3-trifluoromethylphenyl)amide A solution of 260 mg (0.39 mMol) 6-(6-acetylamino-pyrimidin-4-yloxy)-naphthalene-1-carboxylic acid (4-piperazin-1-ylmethyl-3-trifluoromethylphenyl)amide in 2 ml HCl 4 M and 2 ml MeOH is heated at 50° C. for 16 hours. After cooling, the solution is neutralized with 4 ml NaOH 2 M and the resulting suspension is filtered and washed with H$_2$O. The solid is then dried under high vacuum. Column chromatography (SiO$_2$; CH$_2$Cl$_2$/EtOH/NH$_3$ 90:9:1) gives the title compound as colourless solid: mp.: 123-128° C.

Example 83

{6-[5-(4-Piperazin-1-ylmethyl-3-trifluoromethylphenylcarbamoyl)naphthalene-2-yloxy]pyrimidin-4-yl}carbamic acid methyl ester This compound can be obtained analogously to example 81, utilising methylcarbamate in lieu of acetamide in the step 81.3. Beige solid: m.p.: 138-148° C.

Example 84

6-(6-Acetylamino-pyrimidin-4-yloxy)-naphthalene-1-carboxylic acid [4-(4-methyl-piperazin-1-ylmethyl)-3-trifluoromethyl-phenyl]-amide This compound can be obtained analogously to example 81, utilising 4(4-methylpiperazin-1-ylmethyl)-3-trifluoromethylphenylamine in lieu of 4-(4-amino-2-trifluoromethyl-benzyl)-piperazine-1-carboxylic acid tert-butyl ester in the step 81.2. Beige powder:
$^1$H-NMR(DMSO-d$_6$): δ ppm 2.11 (3H, s) 2.15 (3H, s) 2.26-2.44 (8 H, m) 3.57 (2 H, s) 7.45 (1 H, dd, J=9.2, 2.4 Hz) 7.61 (1H, s) 7.64 (1H, dd, J=8.0, 7.2 Hz) 7.70 (1H, d, J=8.6 Hz) 7.78 (1H, d, J=7.0 Hz) 7.85 (1H, d, J=2.4 Hz) 7.99 (1H, d, J=8.8 Hz) 8.07 (1H, d, J=8.5 Hz) 8.25 (1H, s) 8.25 (1H, dd, J=5.1, 4.1 Hz) 8.48 (1H, s) 10.86 (1H, s) 10.96 (1H, s).

Example 85

6-(6-Aminopyrimidin-4-yloxy)-naphthalene-1-carboxylic acid [4-(4-methyl-piperazin-1-ylmethyl)-3-trifluoromethyl-phenyl]-amide This compound can be obtained analogously to example 82, utilising 6-(6-acetylamino-pyrimidin-4-yloxy)-naphthalene-1-carboxylic acid [4-(4-methyl-piperazin-1-ylmethyl)-3-trifluoromethyl-phenyl]-amide in lieu of 6-(6-acetylamino-pyrimidin-4-yloxy)naphthalene-1-carboxylic acid (4-piperazin-1-ylmethyl-3-trifluoromethylphenyl)amide. Colourless powder: $^1$H-NMR(DMSO-d$_6$): δ ppm 2.15 (3 H, s) 2.29-2.35 (4 H, m) 2.36-2.43 (4 H, m) 3.57 (2 H, s) 5.79 (1H, d, J=1.0 Hz) 6.86 (2 H, s) 7.39 (1H, dd, J=9.2, 2.5 Hz) 7.62 (1H, dd, J=8.1, 7.1 Hz) 7.70 (1H, d, J=8.3 Hz) 7.76 (1H, dd, J=7.3, 1.3 Hz) 7.77 (1H, d, J=2.5 Hz) 7.99 (1H, dd, J=8.6, 1.2 Hz) 8.06 (1H, d, J=8.1 Hz) 8.06 (1H, d, J=1.0 Hz) 8.23 (1H, d, J=8.1 Hz) 8.24 (1H, s) 10.83 (1H, s)

Example 86

(6-{5-[4-(4-Methyl-piperazin-1-ylmethyl)-3-trifluoromethyl-phenylcarbamoyl]-naphthalen-2-yloxy}-pyrimidin-4-yl)-carbamic acid methyl ester This compound can be obtained analogously to example 81, utilising 4(4-methylpiperazin-1-ylmethyl)-3-trifluoromethyl-phenylamine in lieu of 4-(4-amino-2-trifluoromethyl-benzyl)-piperazine-1-carboxylic acid tert-butyl ester in the step 81.2. and employing methylcarbamate in lieu of acetamide in the step 81.3. Colourless powder: $^1$H-NMR(DMSO-d$_6$): δ ppm 2.15 (3 H, s) 2.24-2.47 (8 H, m) 3.57 (2 H, s) 3.68 (3 H, s) 7.38 (1H, s) 7.47 (1H, dd, J=9.2, 2.3 Hz,) 7.66 (1H, dd, J=8.2, 7.3 Hz) 7.72 (1H, d, J=8.6 Hz) 7.80 (1H, d, J=7.0 Hz) 7.88 (1H, d, J=2.3 Hz) 8.01 (1H, d, J=8.21 Hz) 8.09 (1H, d, J=8.2 Hz) 8.22-8.31 (m, 2 H) 8.46 (1H, s) 10.86 (1H, s) 10.90(1H, s)

Example 87

6-(6-Acetylamino-pyrimidin-4-yloxy)naphthalene-1-carboxylic acid [4-(4-isopropylpiperazin-1-ylmethyl)-3-trifluoromethylphenyl]amide This compound can be obtained analogously to example 81, utilising 4-(4-isopropylpiperazin-1-ylmethyl)-3-trifluoromethylphenylamine in lieu of 4-(4-amino-2-trifluoromethyl-benzyl)-piperazine-1-carboxylic acid tert-butyl ester in step 81.2. pale yellow crystalline solid: m.p.: 210-213° C.

Example 88

6-(6-Aminopyrimidin-4-yloxy)-naphthalene-1-carboxylic acid [4-(4-isopropyl-piperazin-1-ylmethyl)-3-trifluoromethylphenyl]amide This compound can be obtained analogously to example 82, utilising 6-(6-acetylaminopyrimidin-4-yloxy)-naphthalene-1-carboxylic acid [4-(4-isopropylpiperazin-1-ylmethyl)-3-trifluoromethylphenyl]amide in lieu of 6-(6-acetylamino-pyrimidin-4-yloxy)-naphthalene-1-carboxylic acid (4-piperazin-1-ylmethyl-3-trifluoromethylphenyl)amide. Colourless powder: m.p.: 185-189° C.

Example 89

(6-{5-[4-(4-Isopropyl-piperazin-1-ylmethyl)-3-trifluoromethyl-phenylcarbamoyl]-naphthalen-2-yloxy}-pyrimidin-4-yl)-carbamic acid methyl ester This compound can be obtained analogously to example 81, utilising 4-(4-isopropylpiperazin-1-ylmethyl)-3-trifluoromethylphenylamine in lieu of 4-(4-amino-2-trifluoromethyl-benzyl)-piperazine-1-carboxylic acid tert-butyl ester in step 81.2. and employing methylcarbamate in lieu of acetamide in the step 81.3. Colourless powder: m.p.:=175-178° C.

Example 90

7-(6-Acetylamino-pyrimidin-4-yloxy)-isoquinoline-4-carboxylic acid [4-(4-methyl-piperazin-1-ylmethyl)-3-trifluoromethyl-phenyl]-amide A mixture of 300 mg (0.54 mMol) 7-(6-chloro-pyrimidin-4-yloxy)-isoquinoline-4-carboxylic acid [4-(4-methyl-piperazin-1-ylmethyl)-3-trifluoromethyl-phenyl]-amide, 47.7 mg (0.81 mMol) acetamide, 18.7 mg (0.032 mMol) (9,9-dimethyl-9H-xanthene-4,5-diyl)bis[ diphenylphosphine], 10 mg (0.0108 mMol) tris(dibenzylideneacetone)dipalladium, 248 mg (0.75 mMol) cesium carbonate in 3 ml dry dioxane is heated under an argon atmosphere at 70° C. for 3 h. The cooled suspension is diluted with water, filtered (hyflo) and the residue is dissolved in EtOAc. The solvent is evaporated off under reduced pressure to afford the crude product which is chromatographed by reversed phase MPLC (Büchi system), yielding, after neutralisation with saturated aqueous NaHCO$_3$, the title compound as a beige solid: $^1$H-NMR (DMSO-d$_6$): δ ppm 2.13 (3 H, s) 2.15 (3 H, s) 2.33 (4 H, s) 2.36-2.42 (4 H, m) 3.43 (1H, ddd, J=13.93, 6.98, 5.05 Hz) 3.57 (2 H, s) 7.67 (1H, d, J=0.76 Hz) 7.72 (1H, d, J=9.16 Hz) 7.75 (1H, dd, J=9.09, 2.27 Hz) 7.99 (1H, dd, J=8.21, 1.52 Hz) 8.08 (1 H, d, J=2.46 Hz) 8.24 (1H, d, J=1.71 Hz) 8.33 (1H, d, J=9.16 Hz) 8.49 (2 H, d, J=0.82 Hz) 8.80 (1H, s) 9.43 (1H, s) 10.99 (1H, s) 11.00 (1H, s).

The starting material is prepared as follows:

Step 90.1: 7-(6-Chloro-pyrimidin-4-yloxy)-isoquinoline-4-carboxylic acid [4-(4-methyl-piperazin-1-ylmethyl)-3-trifluoromethyl-phenyl]-amide A mixture of 1.95 g (5.5 mMol) 7-(6-chloro-pyrimidin-4-yloxy)-isoquinoline-4-carboxylic acid (Step 93.2), 1.5 g (5.49 mMol) 4-(4-methyl-piperazin-1-ylmethyl)-3-trifluoromethyl-phenylamine and 6.42 ml (46.2 mMol) triethylamine in 50 ml dry DMF is heated under an argon atmosphere at 50° C. A solution of 5.4 ml (8.2 mMol) propylphosphonic anhydride is then added. After 2 h, the reaction mixture is poured onto an aqueous solution of NaHCO$_3$ and stirred at 0° C. for 1 h. The suspension is then filtered (hyflo) and the solid residue is dissolved in CH$_2$Cl$_2$/

MeOH 5:1. The solvent is evaporated off under reduced pressure to afford a crude product which is purified by reversed phase MPLC (Büchi system), yielding, after neutralisation with saturated aqueous $NaHCO_3$, the title compound as a orange solid.

Example 91

(6-{4-[4-(4-Methyl-piperazin-1-ylmethyl)-3-trifluoromethyl-phenylcarbamoyl]-isoquinolin-7-yloxy}-pyrimidin-4-yl)-carbamic acid methyl ester This compound can be obtained analogously to example 90, utilising methylcarbamate in lieu of acetamide. Beige solid: $^1$H-NMR(DMSO-$d_6$): δ ppm 2.15 (3 H, s) 2.29-2.35 (4 H, m) 2.36-2.43 (4 H, m) 3.57 (2 H, s) 3.69 (3 H, s) 7.43 (1H, d, J=1.0 Hz) 7.72 (1H, d, J=8.5 Hz) 7.75 (1H, dd, J=9.1, 2.4 Hz) 7.99 (1H, dd, J=8.6, 1.1 Hz) 8.09 (1H, d, J=2.5 Hz) 8.24 (1H, d, J=2.1 Hz) 8.34 (1H, d, J=9.2 Hz) 8.45 (1H, d, J=1Hz) 8.80 (1H, s) 9.43 (1H, d, J=0.5 Hz) 10.86 (1H, s) 10.99 (1H, s).

Example 92

7-(6-Amino-pyrimidin-4-yloxy)-isoquinoline-4-carboxylic acid [4-(4-methyl-piperazin-1-ylmethyl)-3-trifluoromethyl-phenyl]-amide This compound can be obtained analogously to example 82, utilising 7-(6-acetylamino-pyrimidin-4-yloxy)-isoquinoline-4-carboxylic acid [4-(4-methyl-piperazin-1-ylmethyl)-3-trifluoromethyl-phenyl]-amide (example 90) in lieu of 6-(6-acetylamino-pyrimidin-4-yloxy)-naphthalene-1-carboxylic acid (4-piperazin-1-ylmethyl-3-trifluoromethylphenyl)amide (example 81). Pale yellow powder: m.p.: 119-122° C.; 1H-NMR(DMSO-d6): δ ppm 2.15 (s, 3 H) 2.23-2.46 (m, 8 H) 3.57 (s, 2 H) 5.90 (s, 1H) 6.95 (s, 2 H) 7.67-7.77 (m, 2 H) 7.97-8.11 (m, 3 H) 8.26 (s, 1H) 8.33 (d, J=9.4 Hz, 1H) 8.80 (s, 1H) 9.44 (s, 1H) 11.01 (s, 1H).

Example 93

7-(6-Amino-pyrimidin-4-yloxy)-isoquinoline-4-carboxylic acid [5-tert-butyl-2-(4-isopropyl-phenyl)-2H-pyrazol-3-yl]-amide 49.0 mg (0.089 mMol) 7-(6-Azido-pyrimidine-4-yloxy)-isoquinoline-4-carboxylic acid [5-tert-butyl-2-(4-isopropyl-phenyl)-2H-pyrazol-3-yl]-amide is dissolved in 5 ml MeOH and submitted to hydrogenation over 12 mg Raney-Nickel at atmospheric pressure at rt for 4 h. After completion the reaction mixture is filtered over a pad of celite and concentrated to give the title compound: m.p.: 131-133° C.; MS: $[M+1]^+$= 522.

The starting material is prepared as follows:

Step 93.1: 7-Hydroxy-isoquinoline-4-carboxylic acid 2.5 g (12.3 mMol) 7-Methoxy-isoquinoline-4-carboxylic acid are dissolved in 10 ml HBr/HOAc (33% wt) and 0.5 ml $H_2O$ is added. The reaction mixture is warmed to 130° C. in a sealed tube. After 3 h it is allowed to cool to ambient temperature. All volatiles are removed under reduced pressure and the remaining crude product is used without further purification for the next step.

Step 93.2: 7-(6-Chloro-pyrimidin-4-yloxy)-isoquinoline-4-carboxylic acid 2.3 g (12.3 mMol) 7-Hydroxy-isoquinoline-4-carboxylic acid are dissolved in 60 ml acetone and 27 ml of an 1 M aqueous solution of NaOH are added, followed by 1.9 g (13.2 mMol) 4,6-dichloropyrimidine. The reaction is stirred at ambient temperature for 12 h and acetone is removed under reduced pressure. The remaining aqueous solution is acidified with 1 M aqueous HCl. The resulting yellow precipitate of the product is isolated by filtration, washed repeatedly with cold water and dried under high vacuum at 60° C.

Step 93.3: 7-(6-Chloro-pyrimidine-4-yloxy)-isoquinoline-4-carboxyl chloride 1.6 g (5.5 mMol) 7-(6-Chloro-pyrimidine-4-yloxy)-isoquinoline-4-carboxylic acid are suspended in $CH_2Cl_2$ and 0.57 ml (6.6 mMol) oxalylchloride are added. The reaction is then stirred under reflux for 2 h, cooled to ambient temperature and concentrated under reduced pressure. The remaining crude product is used without further purification for the next step.

Step 93.4: 7-(6-Chloro-pyrimidine-4-yloxy)-isoquinoline-4-carboxylic acid [5-tert-butyl-2-(4-isopropyl-phenyl)-2H-pyrazol-3-yl]-amide 0.5 g (1.5 mMol) 7-(6-Chloro-pyrimidine-4-yloxy)-isoquinoline-4-carboxyl chloride are dissolved in 4 ml $CH_2Cl_2$ and a solution of 0.4 g 5-tert-butyl-2-(4-isopropyl-phenyl)-2-H-pyrazol-3-ylamine (described for example in GB 0500435.3; 1.5 mMol) and 76 μl (1.7 mMol) pyridine dissolved in 4 ml $CH_2Cl_2$ are added dropwise at rt. The reaction is stirred for 1.5 h at rt and then concentrated under reduced pressure. The residual crude product is purified by flash chromatography ($SiO_2$, $CH_2Cl_2$/MeOH, gradient 0-8% MeOH) to give the title compound as a yellow solid.

Step 93.5: 7-(6-Azido-pyrimidine-4-yloxy)-isoquinoline-4-carboxylic acid [5-tert-butyl-2-(4-isopropyl-phenyl)-2H-pyrazol-3-yl]-amide 128.0 mg (0.24 mMol) 7-(6-Chloro-pyrimidine-4-yloxy)-isoquinoline-4-carboxylic acid [5-tert-butyl-2-(4-isopropyl-phenyl)-2H-pyrazol-3-yl]-amide are dissolved in 5 ml DMF and 31.0 mg (0.47 Mmol) $NaN_3$ are added in one portion at rt. The reaction mixture is stirred for 1.5 h at 70° C. and then concentrated under reduced pressure. The residual crude product is submitted to flash chromatography ($SiO_2$; $CH_2Cl_2$/MeOH; gradient 0-5% MeOH) to give the title compound as a yellow solid.

Example 94

7-(6-Amino-pyrimidin-4-yloxy)-isoquinoline-4-carboxylic acid [5-tert-butyl-2-(4-fluoro-phenyl)-2H-pyrazol-3-yl]-amide The title compound is prepared in analogy to Ex. 93 using 5-tert-butyl-2-(4-fluoro-phenyl)-2H-pyrazol-3-ylamine: m.p.: 124-126° C.; MS: $[M+1]^+$=498.

Example 95

7-(6-Methylamino-pyrimidin-4-yloxy)-isoquinoline-4-carboxylic acid (4-fluoro-3-trifluoromethyl-phenyl)-amide 490 mg (1.0 mMol) 7-(6-Chloro-pyrimidin-4-yloxy)-isoquinoline-4-carboxylic acid (4-fluoro-3-trifluoromethyl-phenyl)-amide are treated with a solution of methylamine in EtOH (33% wt) at rt. The reaction mixture is stirred for 1.5 h at ambient temperature. It is then concentrated under reduced pressure and the remaining crude product submitted to flash chromatography (SiO$_2$, CH$_2$Cl$_2$/MeOH; gradient 1-8% MeOH) to give the title compound as a yellow solid: m.p.: 255-257° C.; MS: [M+1]$^+$=458.

The starting material is prepared as follows:

Step 95.1: 7-(6-Chloro-pyrimidin-4-yloxy)-isoquinoline-4-carboxylic acid (4-fluoro-3-trifluoromethyl-phenyl)-amide The title compound is prepared in analogy to Step 93.4. from 7-(6-chloro-pyrimidine-4-yloxy)-isoquinoline-4-carboxyl chloride and 4-fluoro-3-trifluoromethyl-phenylamine.

Example 96

7-(6-Methylamino-pyrimidin-4-yloxy)-isoquinoline-4-carboxylic acid (3-trifluoromethyl-phenyl)-amide The title compound is prepared in analogy to Ex. 95 from 3-trifluoromethyl-phenylamine: m.p.: 205-208° C.; MS: [M+1]$^+$=440.

Example 97

The following compounds can be obtained in analogy to Example 93 (Q=H) or Example 95 (Q=CH$_3$) starting from 6-(6-chloropyrimidin-4-yloxy)-naphthalene-1-carbonyl chloride (step 81.1) and appropriate 2-amino pyrazoles (described for example in GB 0500435.3).

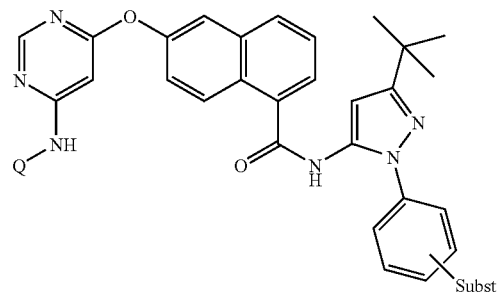

| | Q / Subst | m.p. [° C.] MS [M + 1]$^+$ | Name |
|---|---|---|---|
| a) | CH$_3$ / 4- H$_2$C-N(CH$_3$)$_2$ | 130-135 550 | 6-(6-Methylamino-pyrimidin-4-yloxy)-naphthalene-1-carboxylic acid [5-tert-butyl-2-(4-dimethylaminomethyl-phenyl)-2H-pyrazole-3-yl]-amide |
| b) | CH$_3$ / 4- H$_2$C-(4-methylpiperazinyl) | — 605 | 6-(6-Methylamino-pyrimidin-4-yloxy)-naphthalene-1-carboxylic acid {5-tert-butyl-2-[4-(4-methyl-piperazin-1-ylmethyl)-phenyl]-2H-pyrazol-3-yl}-amide |
| c) | H / 4- H$_2$C-morpholinyl | — 578 | 6-(6-Amino-pyrimidin-4-yloxy)-naphthalene-1-carboxylic acid {5-tert-butyl-2-[4-(morpholin-4-ylmethyl)-phenyl]-2H-pyrazol-3-yl}-amide |
| d) | CH$_3$ / 4- H$_2$C-morpholinyl | 125-128 592 | 6-(6-Methylamino-pyrimidin-4-yloxy)-naphthalene-1-carboxylic acid {5-tert-butyl-2-[4-(morpholin-4-ylmethyl)-phenyl]-2H-pyrazol-3-yl}-amide |
| e) | CH$_3$ / 3- CH$_3$ | 105-110 507 | 6-(6-Methylamino-pyrimidin-4-yloxy)-naphthalene-1-carboxylic acid [5-tert-butyl-2-(3-methyl-phenyl)-2H-pyrazol-3-yl]-amide |
| f) | CH$_3$ / 3- H$_2$C-morpholinyl | 105-110 592 | 6-(6-Methylamino-pyrimidin-4-yloxy)-naphthalene-1-carboxylic acid {5-tert-butyl-2-[3-(morpholin-4-ylmethyl)-phenyl]-2H-pyrazol-3-yl}-amide |

-continued

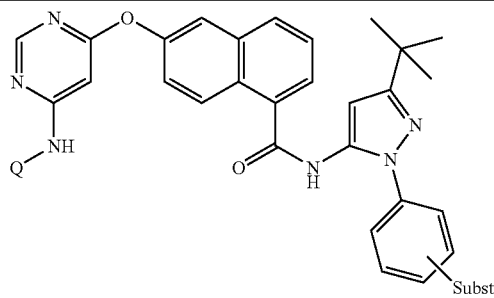

| | Q<br>↘<br>　　Subst | m.p. [° C.]<br>MS<br>[M + 1]⁺ | Name |
|---|---|---|---|
| g) | H<br>3- H₂C\N/ | 140-145<br>536 | 6-(6-Amino-pyrimidin-4-yloxy)-naphthalene-1-carboxylic acid [5-tert-butyl-2-(3-dimethylaminometyl-phenyl)-2H-pyrazol-3-yl]-amide |
| h) | CH₃<br>3- H₂C\N/ | 114-116<br>550 | 6-(6-Methylamino-pyrimidin-4-yloxy)-naphthalene-1-carboxylic acid [5-tert-butyl-2-(3-dimethylaminometyl-phenyl)-2H-pyrazol-3-yl]-amide |
| i) | H<br>3- O=C\N/ | 290-291<br>550 | 6-(6-Amino-pyrimidin-4-yloxy)-naphthalene-1-carboxylic acid [5-tert-butyl-2-(3-dimethylcarbamoyl-phenyl)-2H-pyrazol-3-yl]-amide |
| j) | CH₃<br>3- O=C\N/ | 247-249<br>564 | 6-(6-Methylamino-pyrimidin-4-yloxy)-naphthalene-1-carboxylic acid [5-tert-butyl-2-(3-dimethylcarbamoyl-phenyl)-2H-pyrazol-3-yl]-amide |

Example 98

6-(2-Chloro-pyrimidin-4-ylsulfanyl)-naphthalene-1-carboxylic acid (3-trifluoromethyl-phenyl)-amide To 0.92 g (2.90 mMol) 6-(2-chloro-pyrimidin-4-ylsulfanyl)-naphthalene-1-carboxylic acid, 436 μl (3.49 mMol) 3-trifluoromethyl-aniline, 4.12 ml (29.6 mMol) Et₃N and 153 mg (1.25 mMol) DMAP in 15 ml DMF, 3.56 ml (6.1 mMol) propylphosphonic anhydride are added dropwise. After 1 h at rt, the mixture is poured into water and EtOAc, the aqueous phase separated off and extracted twice with EtOAc. The organic layers are washed with water and brine, dried (Na₂SO₄) and concentrated after addition of SiO₂. The resulting powder is put on top of a SiO₂ column (hexane/EtOAc 9:1). The title compound is eluted with hexane/EtOAc 9:1→2:1 and crystallized from hexane: MS: [M+1]⁺=460/462; TLC(hexane/EtOAc 2:1): $R_f$=0.21; HPLC: $^A t_{Ret}$=17.3.

The starting material is prepared as follows:

Step 98.1: 6-(2-Chloro-pyrimidin-4-ylsulfanyl)-naphthalene-1-carboxylic acid

A mixture of 1.5 g (10 mMol) 2,4-dichloro-pyrimidine, 1.72 g (8.4 mMol) 6-mercapto-naphthalene-1-carboxylic acid [preparation described in *J. Med. Chem.* 32 (1989), 2493] are suspended in 27 ml acetone. Then 20 ml of 1 N NaOH in H₂O are added. After 1 h at rt, the resulting solution is poured into 300 ml of 1 N HCl in H₂O and extracted 3 times with EtOAc. The organic layers are washed with water and brine, dried (Na₂SO₄) and concentrated partially to yield the crystalline title compound: MS: [M+1]=317; HPLC: $^A t_{Ret}$=14.0.

Example 99

{4-[5-(3-Trifluoromethyl-phenylcarbamoyl)-naphthalen-2-ylsulfanyl]-pyrimidin-2-yl}-carbamic acid tert-butyl ester A solution of 770 mg (1.67 mMol) 6-(2-chloro-pyrimidin-4-ylsulfanyl)-naphthalene-1-carboxylic acid (3-trifluoromethyl-phenyl)-amide in 10 ml dioxane is degassed repeatedly by evaporation and flushing with N₂. Then 818 mg (2.5 mMol) Cs₂CO3, 60 mg (0.10 mMol) 4,5-bis(diphenylphosphino)-9,9-dimethylxanthene, 31 mg (0.034 mMol) tris(dibenzylidenaceton)dipalladium(0) and 235 mg (2.0 mMol) carbamic acid tert-butyl ester are added successively. After 2.5 h stirring at 110° C., the mixture is cooled to rt and another 30 mg 4,5-bis(diphenylphosphino)-9,9-dimethylxanthene, 16 mg tris(dibenzylidenaceton)dipalladium(0) and 235 mg carbamic acid tert-butyl ester are added and stirring is continued for 90 min. Then the cooled mixture is poured into EtOAc and water, the aqueous layer separated off and extracted twice with EtOAc. The organic layers are washed with water and brine, dried (Na₂SO₄) and concentrated together with 10 g SiO$_2$. The resulting powder is put on top of a chromatography column (SiO$_2$; hexane/EtOAc 9:1) and the title compound eluated with hexane/EtOAc 9:1-3:2: MS: [M+1]=541; HPLC: $^At_{Ret}$=15.5.

Example 100

6-(2-Amino-pyrimidin-4-ylsulfanyl)-naphthalene-1-carboxylic acid (3-trifluoromethyl-phenyl)-amide A mixture of 117 (0.217 mMol) {4-[5-(3-trifluoromethyl-phenylcarbamoyl)-naphthalen-2-ylsulfanyl]-pyrimidin-2-yl}-carbamic acid tert-butyl ester in 6 ml dioxane and 3.5 ml HCl 4 N in dioxane is stirred for 18 h at rt. The resulting solution is poured into EtOAc and sat. NaHCO$_3$, the aqueous layer separated off and extracted twice with EtOAc. The organic layers are washed with water and brine, dried (Na$_2$SO$_4$) and concentrated. Chromatography (Combi Flash; CH$_2$Cl$_2$/EtOAc 4:1→1:4) and crystallization from hexane gives the title compound: MS: [M+1]$^+$=441; TLC(CH$_2$Cl$_2$/EtOAc 1:2): R$_f$=0.34; HPLC: $^At_{Ret}$=12.8.

Example 101

6-(6-Amino-pyrimidin-4-yloxy)-naphthalene-1-carboxylic acid (2,4-dichloro-3,5-dimethoxy-phenyl)-amide (A) and 6-(6-amino-pyrimidin-4-yloxy)-naphthalene-1-carboxylic acid (2,6-dichloro-3,5-dimethoxy-phenyl)-amide (B)

A suspension of 113 mg (0.27 mMol) 6-(6-amino-pyrimidin-4-yloxy)-naphthalene-1-carboxylic acid (3,5-dimethoxy-phenyl)-amide (Ex. 39m) in 3 ml acetonitrile is cooled to 0° C. Then 3.1 ml of a 0.2 M solution of SO$_2$Cl$_2$ in CH$_2$Cl$_2$ is added dropwise during 10 min. Then the mixture is poured into sat. Na$_2$CO$_3$/H$_2$O 1:3 and EtOAc, the aqueous layer separated off and extracted twice with EtOAc. The organic layers are washed with water and brine, dried (Na$_2$SO$_4$) and concentrated. Chromatography (Combi Flash; ether→EtOAc) gives first A [MS: [M+1]$^+$=485/487; TLC (EtOAc): R$_f$=0.42; $^1$H-NMR(DMSO-d$_6$): 7.43 ppm (s, HC$^6$)], followed by B [MS: [M+1]$^+$=485/487; TLC(EtOAc): R$_f$=0.35; $^1$H-NMR(DMSO-d$_6$): 7.00 ppm (s, HC$^4$)].

Example 102

6-(2-Amino-pyrimidin-4-yloxy)-naphthalene-1-carboxylic acid (2,4-dichloro-3,5-dimethoxy-phenyl)-amide (A) and 6-(2-amino-pyrimidin-4-yloxy)-naphthalene-1-carboxylic acid (2,6-dichloro-3,5-dimethoxy-phenyl)-amide (B)

As described in Ex. 101, 500 mg (1.2 mMol) 6-(2-amino-pyrimidin-4-yloxy)-naphthalene-1-carboxylic acid (3,5-dimethoxy-phenyl)-amide (Ex. 371) in 13 ml acetonitrile are chlorinated with 12 ml of a 0.2 M solution of SO$_2$Cl$_2$ giving A [MS: [M+1]$^+$=485/487; TLC(CH$_2$Cl$_2$/EtOAc 1:9): R$_f$=0.37; $^1$H-NMR(DMSO-d$_6$): 7.40 ppm (s, HC$^6$)] and B [MS: [M+1]$^+$=485/487; TLC(CH$_2$Cl$_2$/EtOAc 1:9): R$_f$=0.25; $^1$H-NMR(DMSO-d$_6$): 6.98 ppm (s, HC$^4$)].

Example 103

6-(6-Acetylamino-pyrimidin-4-yloxy)-isoquinoline-1-carboxylic acid (4-fluoro-3-trifluoromethyl-phenyl)-amide 200 mg (0.43 mMol) 6-(6-Chloro-pyrimidin-4-yloxy)-isoquinoline-1-carboxylic acid (4-fluoro-3-trifluoromethyl-phenyl)-amide, 38 mg (0.64 mMol) acetamide, 15 mg (0.026 mMol) (9,9-dimethyl-9H-xanthene-4,5-diyl)bis[diphenylphosphine], 8 mg (0.008 mMol) tris(dibenzylideneacetone)dipalladium and 199 mg (0.6 mMol) cesium carbonate in 5 ml dry dioxane are heated under an argon atmosphere at 70° C. for 5 h. The cooled suspension is diluted with water, filtered (hyflo) and the residue is dissolved in EtOAc. The solvent is evaporated off under reduced pressure to afford the crude product which is purified by column chromatography (SiO$_2$; CH$_2$Cl$_2$ pure) to give the title compound as a yellow solid: $^1$H-NMR (DMSO-d$_6$): δ ppm 2.13 (s, 3 H) 7.57 (t, J=9.8 Hz, 1H) 7.65 (dd, J=9.38, 2.35 Hz, 1H) 7.70 (s, 1H) 7.96 (d, J=2.3 Hz, 1H) 8.10 (d, J=5.5 Hz, 1H) 8.16-8.23 (m, 1H) 8.45 (dd, J=6.4, 2.5 Hz, 1H) 8.53 (s, 1H) 8.66 (d, J=5.9 Hz, 1H) 9.01 (d, J=9.4 Hz, 1H) 11.06 (s, 1 H) 11.26 (s, 1H).

The starting material is prepared as follows:

Step 103.1: 6-(6-Chloro-pyrimidin-4-yloxy)-isoquinoline-1-carboxylic acid 40 ml (20 mMol) of a 0.5 M solution of sodium methylate in MeOH are added to a suspension of 1.9 g (10 mMol) 6-hydroxy-isoquinoline-1-carboxylic acid (CAS 174299-07-1) in 50 ml MeOH and sonicated until a solution is obtained. The solvent is then evaporated off. The residue is dried in high vacuum for 4 h and 100 ml DMF are added. The suspension is cooled to 10° C. and a solution of 1.55 g (10 mMol) 4,6-dichloropyrimidine in 25 ml DMF is added. The reaction mixture is stirred at room temperature for 14 h. The solvent is evaporated off and the mixture is partitioned between H$_2$O/EtOAc. After extraction, the aqueous phase is neutralized with a 1 N solution of HCl. The suspension is extracted with EtOAc, washed with H$_2$O and brine, dried (MgSO$_4$) and concentrated to give a beige powder:
$^1$H-NMR(DMSO-d$_6$): δ ppm 7.60 (s, 1H) 7.68 (dd, J=9.4, 2.3 Hz, 1H) 7.98 (d, J=2.3 Hz, 1H) 8.04 (d, J=5.5 Hz, 1H) 8.59 (d, J=5.9 Hz, 1H) 8.66 (s, 1H) 8.68 (s, 1H).

Step 103.2: 6-(6-Chloro-pyrimidin-4-yloxy)-isoquinoline-1-carbonyl chloride

A solution of 870 µl (10.2 mMol) oxalyl chloride in 10 ml CH$_2$Cl$_2$ is added to an ice-cooled solution of 1.54 g (5.1 mMol) 6-(6-chloro-pyrimidin-4-yloxy)-isoquinoline-1-carboxylic acid and 10 µl DMF in 75 ml CH$_2$Cl$_2$. The reaction mixture is stirred at room temperature for 1 h. The solvent is then evaporated off under reduced pressure to afford the title compound as a brown solid, which is used directly without further purification.

Step 103.3: 6-(6-Chloro-pyrimidin-4-yloxy)-isoquinoline-1-carboxylic acid (4-fluoro-3-trifluoromethyl-phenyl)-amide A solution of 319 mg (1 mMol) 6-(6-chloro-pyrimidin-4-yloxy)-isoquinoline-1-carbonyl chloride in 20 ml CH$_2$Cl$_2$ is added to a stirred solution of 127 µl (1 mMol) 4-fluoro-3-trifluoromethylaniline and 316 µl (1.81 mMol) diisopropylethylamine in 5 ml CH$_2$Cl$_2$. After 30 min, the reaction mixture is poured into a mixture of water and CH$_2$Cl$_2$. The aqueous phase is separated off and extracted with CH$_2$Cl$_2$. The combined organic layers are washed with water and brine, dried (Na$_2$SO$_4$) and concentrated. Column chromatography (SiO$_2$; CH$_2$Cl$_2$/EtOAc 9:1) gives the title compound as a pale yellow solid: $^1$H-NMR(DMSO-d$_6$): δ ppm 7.53-7.60 (m, 1H) 7.61 (d, J=0.8 Hz, 1H) 7.69 (dd, J=9.4, 2.3 Hz, 1H)

8.01 (d, J=2.3 Hz, 1H) 8.11 (d, J=5.9 Hz, 1H) 8.17-8.24 (m, 1H) 8.45 (dd, J=6.6, 2.3 Hz, 1H) 8.66-8.71 (m, 2 H) 9.03 (d, J=9.38 Hz, 1H) 11.27 (s, 1H).

Example 104

6-(6-Amino-pyrimidin-4-yloxy)-isoquinoline-1-carboxylic acid (4-fluoro-3-trifluoromethyl-phenyl)-amide This compound can be obtained analogously to example 82, utilising 6-(6-acetylamino-pyrimidin-4-yloxy)-isoquinoline-1-carboxylic acid (4-fluoro-3-trifluoromethyl-phenyl)-amide in lieu of 6-(6-acetylamino-pyrimidin-4-yloxy)-naphthalene-1-carboxylic acid (4-piperazin-1-ylmethyl-3-trifluoromethylphenyl)amide (example 81). Colourless powder: m.p.: 219-222° C.;
$^1$H-NMR(DMSO-d$_6$): δ ppm 5.92 (d, J=1.0 Hz, 1H) 6.96 (s, 2 H) 7.50-7.60 (m, 2 H) 7.83 (d, J=2.4 Hz, 1H) 8.07 (d, J=5.4 Hz, 1H) 8.1 (d, J=0.82 Hz, 1H) 8.12-8.22 (m, 1H) 8.42 (dd, J=6.5, 2.5 Hz, 1H) 8.61 (d, J=5.56 Hz, 1H) 8.96 (d, J=9.3 Hz, 1H) 11.21 (s, 1H).

Example 105

6-(6-Amino-pyrimidin-4-yloxy)-isoquinoline-1-carboxylic acid (3-trifluoromethyl-phenyl)-amide This compound can be obtained analogously to example 104, utilising 6-(6-acetylamino-pyrimidin-4-yloxy)-isoquinoline-1-carboxylic acid (3-trifluoromethyl-phenyl)-amide in lieu of 6-(6-acetylamino-pyrimidin-4-yloxy)-isoquinoline-1-carboxylic acid (4-fluoro-3-trifluoromethylphenyl)-amide and employing 3-aminobenzotrifluoride in lieu of 4-fluoro-3-trifluoromethylaniline in the step 103.3. Colourless powder: m.p.: 197-200° C.; 1H-NMR (DMSO-d6): δ ppm 5.92 (d, J=0.8 Hz, 1H) 6.96 (s, 2 H) 7.48 (d, J=7.7 Hz, 1 H) 7.56 (dd, J=9.3, 2.5 Hz, 1H) 7.62 (t, J=8.0 Hz, 1H) 7.83 (d, J=2.4 Hz, 1H) 8.03-8.14 (m, 3 H) 8.40 (s, 1H) 8.61 (d, J=5.6 Hz, 1H) 8.93 (d, J=9.3 Hz, 1H) 11.16 (s, 1H).

Example 106

6-(6-Acetylamino-pyrimidin-4-yloxy)-isoquinoline-1-carboxylic acid [4-(4-methyl-piperazin-1-ylmethyl)-3-trifluoromethyl-phenyl]-amide This compound can be obtained analogously to example 103, utilising 6-(6-chloro-pyrimidin-4-yloxy)-isoquinoline-1-carboxylic acid [4-(4-methyl-piperazin-1-ylmethyl)-3-trifluoromethyl-phenyl]-amide in lieu of 6-(6-chloro-pyrimidin-4-yloxy)-isoquinoline-1-carboxylic acid (4-fluoro-3-trifluoromethyl-phenyl)-amide and employing 4(-4-methylpiperazin-1-ylmethyl)-3-trifluoromethyl-phenylamine in lieu of 4-fluoro-3-trifluoromethylaniline in the step 103.3. Yellow powder: $^1$H-NMR(DMSO-d$_6$): δ ppm 2.13 (s, 3 H) 2.16 (s, 3 H) 2.25-2.45 (m, 8 H) 3.58 (s, 2 H) 7.62 (dd, J=9.3, 2.4 Hz, 1H) 7.68 (d, J=0.7 Hz, 1H) 7.72 (d, J=8.5 Hz, 1H) 7.93 (d, J=2.3 Hz, 1H) 8.03-8.14 (m, 2 H) 8.35 (d, J=1.9 Hz, 1H) 8.51 (s, 1H) 8.63 (d, J=5.6 Hz, 1H) 8.95 (d, J=9.3 Hz, 1H) 11.02 (s, 1H) 11.12 (s, 1H).

Example 107

(6-{1-[4-(4-Methyl-piperazin-1-ylmethyl)-3-trifluoromethyl-phenylcarbamoyl]isoquinolin-6-yloxy}-pyrimidin-4-yl)-carbamic acid methyl ester This compound can be obtained analogously to example 106, utilising methylcarbamate in lieu of acetamide. Beige powder: m.p.: 203-205° C.; 1H-NMR(DMSO-d6): δ ppm 2.17 (s, 3 H) 2.27-2.47 (m, 8 H) 3.58 (s, 2 H) 3.70 (s, 3 H) 7.44 (d, J=0.8 Hz, 1H) 7.63 (dd, J=9.3, 2.5 Hz, 1H) 7.72 (d, J=8.5 Hz, 1H) 7.93 (d, J=2.4 Hz, 1H) 8.03-8.13 (m, 2 H) 8.35 (d, J=1.9 Hz, 1H) 8.46 (d, J=0.9 Hz, 1H) 8.63 (d, J=5.6 Hz, 1H) 8.95 (d, J=9.3 Hz, 1H) 11.02 (s, 1 H) 11.12 (s, 1H).

Example 108

6-(6-Acetylamino-pyrimidin-4-yloxy)-isoquinoline-1-carboxylic acid [4-(4-isopropyl-piperazin-1-ylmethyl)-3-trifluoromethyl-phenyl]-amide This compound can be obtained analogously to example 103, utilising 6-(6-chloro-pyrimidin-4-yloxy)-isoquinoline-1-carboxylic acid [4-(4-isopropyl-piperazin-1-ylmethyl)-3-trifluoromethyl-phenyl]-amide in lieu of 6-(6-chloro-pyrimidin-4-yloxy)-isoquinoline-1-carboxylic acid (4-fluoro-3-trifluoromethyl-phenyl)-amide and employing 4(-4-isopropylpiperazin-1-ylmethyl)-3-trifluoromethyl-phenylamine in lieu of 4-fluoro-3-trifluoromethylaniline in the step 103.3. Beige powder: 1H-NMR(DMSO-d6): δ ppm 0.96 (d, J=6.5 Hz, 6 H) 2.13 (s, 3 H) 2.34-2.48 (m, 8 H) 2.60 (sept., J=6.5 Hz, 1H) 3.56 (s, 2 H) 7.62 (dd, J=9.3, 2.5 Hz, 1H) 7.68 (d, J=0.9 Hz, 1H) 7.73 (d, J=8.5 Hz, 1H) 7.93 (d, J=2.5 Hz, 1H) 8.03-8.13 (m, 2 H) 8.35 (d, J=2.1 Hz, 1H) 8.51 (d, J=1.0 Hz, 1H) 8.63 (d, J=5.6 Hz, 1H) 8.95 (d, J=9.3 Hz, 1H) 11.02 (s, 1 H) 11.12 (s, 1H).

Example 109

(6-{1-[4-(4-Isopropyl-piperazin-1-ylmethyl)-3-trifluoromethyl-phenylcarbamoyl]isoquinolin-6-yloxy}-pyrimidin-4-yl)-carbamic acid methyl ester This compound can be obtained analogously to example 108, utilising methylcarbamate in lieu of acetamide. Beige powder: 1H-NMR(DMSO-d6): δ ppm 0.96 (d, J=6.5 Hz, 6 H) 2.35-2.48 (m, 8 H) 2.60 (sept., J=6.5 Hz, 1H) 3.56 (s, 2 H) 3.70 (s, 3 H) 7.44 (d, J=0.9 Hz, 1H) 7.63 (dd, J=9.3, 2.5 Hz, 1H) 7.73 (d, J=8.3 Hz, 1H) 7.93 (d, J=2.4 Hz, 1H) 8.03-8.13 (m, 2 H) 8.35 (d, J=2.1 Hz, 1H) 8.46 (d, J=0.9 Hz, 1H) 8.63 (d, J=5.6 Hz, 1H) 8.95 (d, J=9.2 Hz, 1H) 10.88 (s, 1H) 11.12 (s, 1H).

Example 110

6-(2-Amino-pyrimidin-4-yloxy)-isoquinoline-1-carboxylic acid (4-fluoro-3-trifluoromethyl-phenyl)-amide A solution of 27 mg (0.042 mMol) 6-(2-amino-6-chloro-pyrimidin-4-yloxy)-isoquinoline-1-carboxylic acid(4-fluoro-3-trifluoromethyl-phenyl)-amide in 3 ml THF and 60 µl (0.42 mMol) Et$_3$N is hydrogenated in presence of 15 mg Pd/C (10%; Engelhard 4505). The catalyst is filtered off, the filtrate concentrated and re-dissolved in EtOAc and water. The separated aqueous layer is extracted twice with EtOAc. The organic phases are washed with water and brine, dried (Na$_2$SO$_4$) and concentrated. Reversed phase chromatography gives the title compound: MS: [M+1]$^+$=444; HPLC: $^A$t$_{Ret}$=13.6.

The starting material is prepared as follows:

Step 110.1: 6-(2-Amino-6-chloro-pyrimidin-4-yloxy)-isoquinoline-1-carboxylic acid(4-fluoro-3-trifluoromethyl-phenyl)-amide To a suspension of 80 mg (0.423mMol) 6-hydroxy-isoquinoline-1-carboxylic acid in 1 ml methanol, 157 µl (0.85 mMol) of a 5.4 M solution of NaOCH₃ in methanol are added. Treatment under ultrasound produces a clear solution which is concentrated in vacuo and finally dried for 3 h at 50° C. Then 4 ml of DMEU followed by a solution of 154 mg (0.94 mMol) of 2-amino-4,6-dichloro-pyrimidine are added to the residue. Stirring for 3 d at rt leads to 6-(2-amino-6-chloro-pyrimidin-4-yloxy)-isoquinoline-1-carboxylic acid {MS: [M−1]= 315}. Then 590 μl(4.24 mMol) Et₃N, 23 mg (0.19 mMol) DMAP, 70 μl (0.544 mMol) 4-fluoro-3-trifluorom-ethyl-aniline and finally 490 μl (0.85 mMol) propylphosphonic anhydride are added successively. After 16 h at rt, the mixture is diluted with EtOAc and water. The separated aqueous layer is extracted twice with EtOAc. The organic phases are washed with water and brine, dried (Na₂SO₄) and concentrated. Chromatography [Combi Flash; hexane/EtOAc 4:1→1:1] gives the title compound: MS: [M+1]⁺=478; TLC (hexane/EtOAc 1:1): $R_f$=0.37; HPLC: $^At_{Ret}$=17.8.

Example 111

The following isoquinoline carboxamides can be prepared analogously:

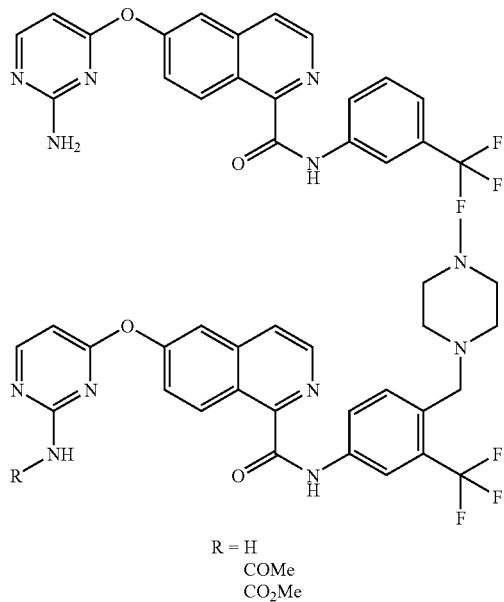

R = H
COMe
CO₂Me

Example 112

6-[(6-Aminopyrimidin-4-yl)oxy]-N-[4-(4-morpholin-4-ylcyclohexyl)phenyl]-1-naphthamide

Step 112.1: 4,6-Dimethoxy-1,3,5-triazin-2-yl 6-hydroxy-1-naphthoate

Add 21.4 g (0.11 mol) of 6-hydroxy-1-naphthoic acid in to 450 mL of acetonitrile, then added 33.2 g (0.12 mol) of 4-(4,6-Dimethoxy-[1,3,5]triazin-2-yl)-4-methyl-morpholin-4-ium chloride, and stir at room temperature overnight. Add 165 mL of water, stir for 5 min, filter, and rinse the cake with 150 mL of water. Dry at room temperature in a vacuum oven to obtain 4,6-dimethoxy-1,3,5-triazin-2-yl 6-hydroxy-1-naphthoate 27.22 g (72.9%).

Step 112.2: 4-(4-Morpholin-4-yl-cyclohexyl)-phenylamine a) Dimethyl 1-(4-nitrophenyl)-4-oxo-1,3-cyclohexanedicarboxylate Charge a 2000-mL reactor with 156.9 g of ethyl 4-nitrophenylacetate. Add 443 g of tetrahydrofuran. Stir the solution and cool it to −10° C. Add in one portion 15.58 g of Triton B [40% (w/w) solution of trimethylbenzylammonium hydroxide in methanol] and then add a solution of 161.4 g of methyl acrylate in 221.5 g of tetrahydrofuran in 45 min keeping the reaction temperature below −10° C. Warm the mixture to 5° C. over 15 min. Stir the mixture at 5° C. until ethyl 4-nitrophenylacetate is completely consumed. Continue stirring and add slowly from a dropping funnel 540.6 g of 30% (w/w) of sodium methoxide in methanol in 90 min. Stir the reaction at 5° C. for 1 h then warm the mixture to 22° C. over 1 h and stir the mixture for 16 h. Cool the reaction to 0-5° C. Charge a separate flask with 1500 g of deionized water. Cool the contents to 0-5° C. Add the cold reaction mixture to the cold water with vigorous stirring. Complete the addition in 30-60 min keeping the batch at 5-10° C. Rinse the reactor with 136 g of methanol. Keep the mixture cold (<10° C.) and acidify to pH 1-2 by controlled addition of 577.2 g of 6 N HCl. Stir the mixture at 5-10° C. for 2 h. Filter the solids. Wash the cake with water (3×600 mL). Dry the product at 45-50° C./≈30 mbar (18 h). Yield 235.6 g.

b) 4-(4-Nitrophenyl)-cyclohexanone

Charge a 2000-mL reactor with 80.48 g of dimethyl 1-(4-nitrophenyl)-4-oxo-1,3-cyclohexanedicarboxylate, 98.0 g of sodium acetate, trihydrate and 440.4 g of dimethyl sulfoxide. Stir the mixture and add 27.0 g of deionized water. Warm the mixture to 130° C. Hold the reaction at 130° C. for 2 h. Warm the reaction to 150° C. Hold the batch at 150-155° C. for 2.5 h. Cool the reaction to 22° C. Stir the reaction mixture and add from a dropping funnel a solution of 80.6 g of sodium bicarbonate dissolved in 1320 mL of deionized water at a rate to keep the reaction temperature at 25-30° C. Stir the resulting dark slurry for 2 h. Filter the solids and wash the cake with 160 g of deionized water then with 2×120 g of deionized water. Dry the product at 45-50° C./≈30 mbar (18 h). Yield 41.9 g. Purity: 76.4%. This material is carried into the next ste as such.

c) trans-4-[4-(4-Nitrophenyl)cyclohexyl]morpholine hydrochloride

Charge a nitrogen flushed 1-L, 4-necked round-bottomed flask equipped with a mechanical stirrer, a thermometer a reflux condenser and an addition funnel, with 50.0 g (0.228 mol) of 4-(4-Nitrophenyl)-cyclohexanone and 541 g (600 mL) of ethyl acetate. Stir and heat the suspension to reflux. Hold the reaction at reflux for 30 min. Cool the mixture to 50° C. and filter the solids. Wash the flask and filter cake with 45 g (50 mL) of ethyl acetate. Combine the wash with the filtrate and transfer to a clean 2-L reactor equipped with a mechanical stirrer, a thermometer a reflux condenser and an addition funnel. Stir the mixture at 25° C. Add 19.9 g (0.228 mol) of morpholine and 6.8 g (6.5 mL) of glacial acetic acid. Add 67.7 g (0.319 mol) of sodium triacetoxyborohydride in 5 portions over 15 minutes maintaining the reaction temperature at 22° C. throughout the addition. Stir the mixture at 25° C. until 4-(4-Nitrophenyl)-cyclohexanone is consumed (3 h). Carefully add 500 mL of water over 30 min. Transfer to a nitrogen-flushed 3-L, 4-necked round-bottomed flask equipped with overhead stirrer, nitrogen inlet and outlet, thermocouple and pH probe. Adjust the pH to 1.5-2.0 with 12 N hydrochloric acid (≈50 mL) while maintaining a reaction temperature at 20-25° C. Stir for 15 min and separate the phases. Extract the organic phase with 2×125 mL of 2 N hydrochloric acid solution. Separate the phases and combine the aqueous extracts (pH=0.8). Add to the combined aqueous extracts 350 mL of ethyl acetate. Stir and adjust the pH to 8.5 with the addition of 50% sodium hydroxide (≈82 mL). Stir for 15 min and separate the phases. Clarify the organic phase by filtering through glass-fiber filter paper.

Distil the solvent under vacuum (30° C./40 mbar). Add to the residue 500 mL of 200 proof ethanol. Distil the solvent under vacuum (30° C./40 mbar). Add to the residue 650 mL of 200 proof ethanol. Stir and add 115.0 mL of sodium methoxide, (25% w/w solution in methanol) over 2-3 min. Heat the mixture to reflux and hold it at reflux for 6 h. Cool the mixture to 22° C. Stir and add 6 N hydrochloric acid solution (~145 mL) over 15 min until pH is <2.5. Add 180 g of water and stir for 15 min. Filter through a 9 cm×1 cm pad of Filter Cel. Wash the filter cake with a solution of 60 mL of ethanol in 30 mL of water and combine the wash with the filtrate. The product thus obtained as a solution in ethanol/water was used directly in the next step.

d) 4-(4-Morpholin-4-yl-cyclohexyl)-phenylamine

Purge the Mettler-Toledo RC1 reaction calorimeter by pressurizing with nitrogen to 50 psig (4.5 bar abs), and depressurizing to 0 psig. Repeat the pressurization/depressurization cycle four times. Add 6.71 g of 10% palladium on carbon (50% water wet). Purge with nitrogen five times as described above. Add the aqueous ethanol solution of trans-4-[4-(4-nitrophenyl)cyclohexyl] morpholine hydrochloride from the previous step. With the reaction mixture under 1 atm of nitrogen, stir the vessel at an agitation rate of 500 rpm and heat the batch temperature to 50° C. over a 30 min period. Let the batch temperature equilibrate at 50° C. at an agitation rate of 550 rpm and turn off the agitator. Purge the headspace of N2, and replace with H2 by pressurizing with H2 to 50 psig (4.5 bar abs), depressurizing to 0 psig, and repeating the pressurization/depressurization cycle 4 times. After the final depressurization, set the reactor pressure to 50 psig (4.5 bar abs), agitate at 550 rpm to start the reaction. The reaction is exothermic. Continue hydrogenation until the uptake of hydrogen gas levels off. Cool the reaction to 25° C. Purge five times with nitrogen. Remove the reaction mixture from the RC1. Wash the reactor with 250 mL of water and combine the wash with the batch. Filter the batch and distil (35±5° C., 35 mbar) to remove ethanol. Add to the residue 500 mL of ethyl acetate. Stir and adjust the pH to 9.5±0.5 with the addition of sodium hydroxide, 50% in water (≈35 g, 22 mL). Separate the phases. Extract the aqueous phase once with 250 mL of ethyl acetate and combine the organic extracts. Wash the organic phase with 150 mL of water, once with 150 mL of brine and concentrate to a solid residue. Chromatograph the crude product on silica gel using ethyl acetate/triethylamine (100:1) as the mobile phase to afford product (31 g, 68% overall corrected yield from ketone) as a yellow solid. Mp. 161-163° C.

Step 112.3: 6-Hydroxy-N-[4-(4-morpholin-4-ylcyclohexyl)phenyl]-1-naphthamide

Mix 4,6-Dimethoxy-1,3,5-triazin-2-yl 6-hydroxy-1-naphthoate (3.44 g 10.5 mmol), 4-(4-Morpholin-4-yl-cyclohexyl)-phenylamine (2.74 g, 10.5 mmol), and 50 mL of N-methylpyrrolidone, stir, and hold at 55° C. for 5.5 h. Cool to room temperature, quench with 150 mL of water and 50 mL of ethyl acetate. Filter and dry at 65° C. in a vacuum oven to obtain 6-hydroxy-N-[4-(4-morpholin-4-ylcyclohexyl)phenyl]-1-naphthamide 2.34 g (52%).

Step 112.4: 6-[(6-Aminopyrimidin-4-yl)oxy]-N-[4-(4-morpholin-4-ylcyclohexyl)phenyl]-1-naphthamide To a 100-mL flask, charge 6-hydroxy-N-[4-(4-morpholin-4-ylcyclohexyl)phenyl]-1-naphthamide (2.34 g, 5.9 mmol), 4-amino-6-chloropyrimidine (0.80 g, 6.2 mmol), potassium hydroxide (0.418 g, 7.45 mmol), potassium iodide (0.979 g, 5.9 mmol), and N-methylpyrrolidone (45 mL). Hold at 135° C. for 13 h. Cool to 50° and slowly add water (90 mL), and hold at 50° C. for 30 min. Cool to room temperature filter and rinse with water. Dry at 65° C. in a vacuum oven to obtain crude 6-[(6-aminopyrimidin-4-yl)oxy]-N-[4-(4-morpholin-4-ylcyclohexyl)phenyl]-1-naphthamide 2.19 g (Y. 71%, purity. 88.5%). The crude product was purified by chromatography on silica gel using $CH_2Cl_2$/MeOH/$Et_3$N=95/5/1. MS. $[M+1]^+=524$ Example 113

6-[(2-Aminopyrimidin-4-yl)oxy]-N-[4-(4-morpholin-4-ylcyclohexyl)phenyl]-1-naphthamide In a nitrogen flushed 50 mL 4-neck round-bottom flask equipped with a magnetic stirrer, thermocouple and cooling bath, suspend 1.0 g (3.55 mmol) of 6-(2-Amino-pyrimidin-4-yloxy)-naphthalene-1-carboxylic acid and 0.97 g (3.73 mmol) of 4-(4-Morpholin-4-yl-cyclohexyl)-phenylamine in 10 mL of N,N-dimethylformamide (DMF). Stir the suspension and add 1.5 mL (10.65 mmol) of triethylamine to obtain a brown solution (21° C.). Add 0.52 g (4.26 mmol) of N,N-dimethylaminopyridine and cool to 4° C. Add by drops, 2.72 g (4.26 mmol) of 1-propanephosphonic acid cyclic anhydride (50 wt. % solution in ethyl acetate) while maintaining a batch temperature of ≦10° C. throughout the addition. Remove the cooling bath and allow the reaction mixture to warm to 20° C. over 15 min. Stir the reaction mixture at 20° C. for 30 min. and monitor the reaction for the disappearance of 6-(2-Amino-pyrimidin-4-yloxy)-naphthalene-1-carboxylic acid by HPLC. Pour the reaction mixture into a rapidly stirring solution of 20 mL water and 20 mL brine (a thick precipitate forms). Stir the resulting suspension of 15 min. Filter the solids through polypropylene filter paper, wash the filter cake with 50 mL of ice water and dry the solids at 50° C., 50 mbar for 16 h. Grind the solids transfer them to a nitrogen flushed 50 mL. 4-neck round-bottom flask equipped with a magnetic stirrer, thermocouple and heating mantle. Add 35 mL of methanol. Stir the suspension and heat to 65° C. Hold the suspension at this temperature for 1 h, cool to 25° C. over 30 min and hold for 30 min. Filter the solids through polypropylene filter paper, wash the filter cake with 5 mL of cold (4° C.) methanol and dry the solids at 50° C., 50 mbar to afford 1.6 g of 6-[(2-Aminopyrimidin-4-yl)oxy]-N-[4-(4-morpholin-4-ylcyclohexyl)phenyl]-1-naphthamide (86% yield).

Example 114

Dry-Filled Capsules 500 capsules, each comprising as active ingredient 0.25 g of one of the compounds of formula I mentioned in the preceding Examples, are prepared as follows:

Composition

| active ingredient | 1250 g |
|---|---|
| talcum | 180 g |
| wheat starch | 120 g |
| magnesium stearate | 80 g |
| lactose | 20 g |

Preparation process: The mentioned substances are pulverised and forced through a sieve of 0.6 mm mesh size. 0.33 g portions of the mixture are introduced into gelatin capsules using a capsule-filling machine.

Example 115

Soft Capsules 5000 soft gelatin capsules, each comprising as active ingredient 0.05 g of one of the compounds of formula I mentioned in the preceding Examples, are prepared as follows:
Composition

| active ingredient | 250 g |
|---|---|
| PEG 400 | 1 liter |
| Tween 80 | 1 liter |

Preparation process: The active ingredient is pulverised and suspended in PEG 400 (polyethylene glycol having an Mr of from approx. 380 to approx. 420, Fluka, Switzerland) and Tween®80 (polyoxyethylene sorbitan monolaurate, Atlas Chem. Ind. Inc., USA, supplied by Fluka, Switzerland) and ground in a wet pulveriser to a particle size of approx. from 1 to 3 μm. 0.43 g portions of the mixture are then introduced into soft gelatin capsules using a capsule-filling machine.

What is claimed is:

1. 6-(6-Hydroxymethyl-pyrimidin-4-yloxy)-naphthalene-1-carboxylic acid (3-trifluoromethyl-phenyl)-amide, or a tautomer thereof, or a salt thereof.

2. A pharmaceutical composition comprising a compound or salt thereof according to claim 1, and a pharmaceutically acceptable carrier.

3. A method of treating a patient with a protein kinase dependent disease, the method comprising the step of administering a therapeutically effective amount of the compound of claim 1 or a tautomer or salt thereof to the patient, wherein the protein kinase dependent disease is selected from ocular neovascularisation, diabetic retinopathy, age-related macular degeneration, psoriasis, Von Hippel Lindau disease, hemangioblastoma, angioma, diabetic nephropathy, malignant nephrosclerosis, thrombotic microangiopathy syndrome, transplant rejection, glomerulonephritis, mesangioproliferative glomerulonephritis, haemolytic-uraemic syndrome, hypertensive nephrosclerosis, atheroma, arterial restenosis, hepatic cirrhosis, diabetes, endometriosis, chronic asthma, arterial or post-transplantational atherosclerosis, breast cancer, adenocarcinoma, colorectal cancer, lung cancer, renal cancer, liver cancer, pancreatic cancer, ovarian cancer, cancer of the prostate, myeloma, multiple myeloma, myelodysplastic syndrome, acute myeloid leukemia, agnogenic myeloid metaplasia, mesothelioma, glioma and/or glioblastoma.

* * * * *